US 6,673,355 B1

(12) United States Patent
Estes et al.

(10) Patent No.: US 6,673,355 B1
(45) Date of Patent: *Jan. 6, 2004

(54) ROTAVIRUS ENTEROTOXIN NSP4 AND METHODS OF USING SAME

(75) Inventors: Mary K. Estes, Friendswood, TX (US); Judith M. Ball, Conroe, TX (US); Peng Tian, Congers, NY (US)

(73) Assignee: Baylor College of Medicine, Houston, TX (US)

( * ) Notice: Subject to any disclaimer, the term of this patent is extended or adjusted under 35 U.S.C. 154(b) by 34 days.

This patent is subject to a terminal disclaimer.

(21) Appl. No.: 09/705,621

(22) Filed: Nov. 3, 2000

Related U.S. Application Data

(63) Continuation-in-part of application No. 08/973,961, filed as application No. PCT/US96/10523 on Jun. 14, 1996, now Pat. No. 6,210,682.
(60) Provisional application No. 60/000,220, filed on Jun. 14, 1995.

(51) Int. Cl.$^7$ .................. A61K 39/15; A61K 39/42; A61K 39/12; C07K 7/00; C12N 7/04
(52) U.S. Cl. .................. 424/215.1; 424/139.1; 424/147.1; 424/159.1; 424/204.1; 530/300; 530/324; 435/236
(58) Field of Search .................. 424/139.1, 147.1, 424/159.1, 184.1, 185.1, 186.1, 215.1, 204.1; 435/69.1, 69.3, 235.1, 236; 530/300, 350, 326, 324, 325; 536/23.72

(56) References Cited

U.S. PATENT DOCUMENTS

| 4,341,763 A | 7/1982 | Zygraich .................. 424/89 |
| 4,344,935 A | 8/1982 | Leclerc et al. .................. 424/89 |
| 4,636,385 A | 1/1987 | Plotkin et al. .................. 424/89 |
| 4,686,281 A | 8/1987 | Dodin et al. .................. 530/327 |
| 4,704,275 A | 11/1987 | Wyatt et al. .................. 424/89 |
| 4,745,051 A | 5/1988 | Smith et al. .................. 435/68 |
| 4,853,333 A | 8/1989 | Hsiao et al. .................. 435/256 |
| 4,861,864 A | 8/1989 | Atkinson et al. .................. 530/324 |
| 4,898,815 A | 2/1990 | Dodin et al. .................. 435/7 |
| 5,147,639 A | 9/1992 | Welter et al. .................. 424/89 |
| 5,186,933 A | 2/1993 | Estes .................. 424/89 |
| 5,474,773 A | 12/1995 | Ward |
| 5,891,676 A | 4/1999 | Estes .................. 435/69.3 |
| 6,210,682 B1 * | 4/2001 | Estes et al. .................. 424/215.1 |

FOREIGN PATENT DOCUMENTS

| EP | 0251467 | 1/1988 |
| FR | 2551088 | 3/1985 |
| WO | WO9201784 | 2/1992 |
| WO | WO9401134 | 1/1994 |
| WO | WO 97/00088 | 1/1997 |

OTHER PUBLICATIONS

Copy of PCT Search Report.
Estes, M., "Cloning and nucleotide sequence of the simian rotavirus gene 6..,"*Nucleic Acids Research*, 12(4):1875–1887 (1984).
Miller, L., "Insect Baculoviruses: Powerful Gene Expression Vectors," *BioEssays*, 11:91–95 (Oct. 1989).
Estes, M., et al., Antigenic structures of rotaviruses, *Immunochemistry of Viruses. The Basis for Serodiagnosis and Vaccines.*, 21:389–405 (1985).
Miller, L., "A Virus Vector for Genetic Engineering in Invertebrates." Genetic Engineering in the Plant Sciences, 14:203–224 (1981).
Estes, M., et al., *Immunobiology of Proteins and Peptides—III*, 201–214 (1985).
Kapikian,m A., et al., "Rotaviruses," *Virology*, 37:863–906 (1985).
Mason, B., "Biochemical Mapping of the Simian Rotavirus SA11 Genome," *Journal of Virology*, 46:413–423 (May 1983).
Chan, W., et al., "Two Glycoproteins Are Produced from the Rotavirus Neutralization Gene," *Virology* 151:243–252 (1986).
Bican, P., et al. "Purification and Characterization of Bovine Rotavirus Cores," *Journal of Virology*, 43(3): 1113–1117 (Sep. 1982).
Gorziglia, M., et al., "Biochemical Evidence for the Oligomeric (Possible Trimeric) Structure . . . ," *J. Gen. Virol.*, 66:189–1900(1985).
Beards, G., et al., "Enzyme Linked Immunosobent Assays Based on Polyclonal . . . ," *Journal of Clinical Microbiology*, 19(2):2480254 (Feb. 1984).
Nakata, S., et al., "Antigenic Characterization and Elisa Detection of Adult Diarrhea Rotaviruses,"*The Journal of Infectious Disease*, 154:448–455 (Sep. 1996).
Estes, M., et al., "Simian rotavirus SA11 Replication in Cell Cultures," *Journal of Virology*, 31(3):810–815 (Sep. 1979).
Smith, G., et al., "Molecular Engineering of the *Autographa californica* nuclear Polyhedrosis Virus Genome: . . . ," *Journal of Virology*, 46:584–593 (May 1983).
Both, G., et al, "Coding Assignment and Nucleotide Sequence of Simian Rotavirus SA11 Gene Segment," *Journal of Virology*, 48:335–339 (Nov. 1983).

(List continued on next page.)

*Primary Examiner*—James Housel
*Assistant Examiner*—Shanon Foley
(74) *Attorney, Agent, or Firm*—Fulbright & Jaworski, LLP

(57) ABSTRACT

The rotavirus nonstructural glycoprotein, NSP4, performs multiple functions in the virus replication cycle, especially during viral morphogenesis. Specifically, NSP4 is an intracellular receptor that mediates the acquisition of a transient membrane envelope during the budding of newly formed subviral particles into the endoplasmic reticulum (ER). The present invention relates to NSP4 and methods of use. More particulary, it relates to the use of NSP4 and fragments thereof (NSP4 114–135, NSP4 120–147, NSP4 112–174, or NSP4 112–150) as a prevention and/or treatment of rotaviral disease.

9 Claims, 17 Drawing Sheets

OTHER PUBLICATIONS

Figure 1:
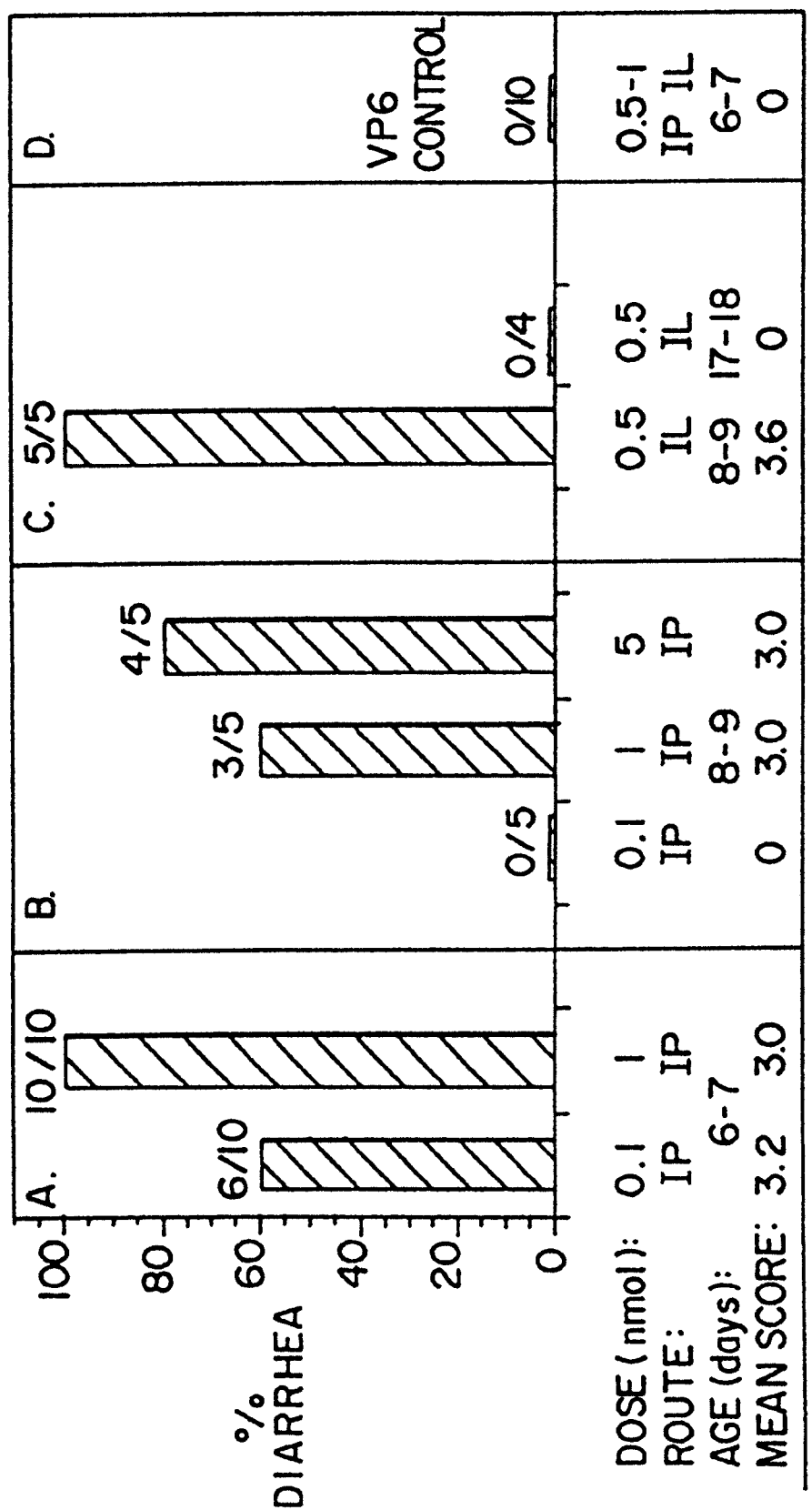

Au, k., et al., "A Subviral Particle Binding Domain on the Rotavirus Nonstructural Glycoprotein NS28," *Virology* 194:665–673 (1993).

Richardson, S., et al. "Analysis of Homotypic and Heterotypic Serum Immune Responses to Toravirus . . . ," J. of Clin. Microbiology, 31(2):3337–385, (1993).

Cohen, et al., "Molecular Cloning of the Simian Rotavirus SA11,"Double–Stranded RNA Viruses, International Symposium on Double Stranded RNA Viruses, held Oct. 5–10, 1982, St. Thomas, U.S. Virgin Islands.

Summers and Smith, "Manual of Methods for Baculovirus Vectors and Insect Cell Ceulture Procedures," *Texas Agricultural Experiment Station*, Bulletin 1555, first prinint (1987), second printing (1988).

Ball, J., et al., "Age–dependent Diarrhea Induced by a Rotaviral Nonstructural glycoprotein," Science 272(5258):101–4 (1996).

Mason, H., et al., "Expression of Norwalk virus capsid protein in transgenic tobacco and potato and its immunogenicity in mice," *Proceedings of the National Academy of Sciences of USA*, 93:5335–5340.

Tian, T. et al., "The Rotavirus Nonstructural Glycoprotein NSP4 Possesses Membrane Destablization Activity," *Journal of Virology*, 69(9):5763–5772 (1995).

Hermann, J., et al., "Monoclonal Antibodies for Detection of Norwalk Virus Antigen in Stools," *Journal of Clinical Microbiology*, 33(9):2511–2513 (1995).

Matson, D., et al., "Assessment of epitope–blocking assays for measuring antibody to rotavirus" Journal of Virological Methods, 48:293–300 (1994).

O'Ryan, M., et al., "Anti–Rotavirus G Type–Specific and Isotype–specific Antibodies in Children with Natural Rotavirus Infections" *The Journal of Infectious Diseases*, 169:504–511 (1994).

Offit, P., et al., "Noninfectious Rotavirus (Strain RRV) Induces an Immune Response in Mice Which Portects against Rotavirus Challenge," *Journal of Clinical Microbiology*, 27(5):885–888 (1989).

Both, G., et al., "Serotype–specific glycoprotein of simian 11 rotavirus Coding assignment and gene sequence," *Proc. Natl. Acad. Sci. USA*, 80:3091–3095 (1993).

Miyamota, C., et al., "Production of Human c–myc Protein in Insect Cells Infected with a Baculovirus Expression Vector," *Molecular and Cellular Biology*, 5(10):2860–2865 (1985).

Mason, B., et al., "Biochemical Mapping of the Simian Rotavirus SA11 Genome," *Journal of Virology*, 46(2):413–423 (1983).

Boyle, J., et al., "RNA–Binding Proteins of Bovine Rotavirus," *Journal of Virology*, 58(2): 561–568 (1986).

Imai, M., et al., Molecular cloning of double–stranded RNA virus genomes, *Proc. Natl. Acad. Sci. USA*, 80:373–377 (1983).

Lin., M., et al., "Diagnosis of Toravirus Infection with Cloned cDNA Copies of Viral Genome Segments," *Journal of Virology*, 55(2):509–512(1985).

Sabara, M., et al., "Identirfiction of a Bovine Rotavirus Gene and Gene Product Influencingt Cellular Attachment," *Journal of Virology*, 51(2): 489–496 (1984).

Tian, P., et al, "The Nonstructural Glycoprotein of Toravirus Affects Intracellular Calcium Levels," *Journal of Virology*, 68(1):251–257 (1994).

Both, G., et al., "Coding Assignment and Nucleotide Sequence of Simian Rotavirus SA11 Gene Segment 10: Location of Glycosylation . . . ," *Journal of Virology*, 48(2):335–339 (1983).

Lima, A., et al., :Effects of Clostridium Difficile Toxins A and B in Rabbit Small . . . , Infection and Immunity 56(3): 582–588 (1988).

Bastardo, J.W., "Preparation and Characterization of Antisera to Electrophoretically Purified SA11 Virus Polypeptides," *Infectious Immunology*, 34(3):641–647 (1981).

Smith, G.E., et al., Production of Human Beta Interferon in Insect Cells Infected with a Baculovirus Expression Vector, *Mol. Cell. Biol.*, 3(12):2156–2165(1983).

Ijaz, et al., "Effect of different routes of immunization . . . "Antiviral Research, 8(5–6):283–298 (1987).

Flores, J., et al., "Comparison of reactogenicity and antigenicity of M37 rotavirus vaccine and rhesus–rotavirus–based quadrivalent vaccine," Lancet 2:330–334, (1990).

Midthum, et al., Reassortant rotaviruses as potential live rotavirus vaccine candidates: *J. of Virology*, 53(3):949–954, (1985).

Dimitrov, D.H., et al., "Detection of Rotaviruses by Nucleic Acid Hybridization . . . ,"*J. of Infectious Diseases*, 152(2):293–300 (1985).

Flores, J., et al., "A DOT Hybridisation Assay for Detection of Rotavirus," *The Lancet*, 555–559 (1983).

McNeal, M., et al., "Active Protection against Rotavirus Infection fo Mice . . . ," *Virology*, 191:150–157 (1992).

Ball, J., et al., "Immune Responses to Mucosal Pathogens and Novel Mucosal Vaccines," *Journal of Cellular Biochemistry*, Abstract J1–200:254.

Matson, D., et al., "Fecal Antibody Responses to Syptomatic and Asymptomatic Rotavirus Infections," *J. of Infectious Diseases*, 167:577–83 (1993).

Michelangeli, F., et al., "Selective Depletion of Stored Calcium by Thapsigargin Blocks . . . ," J. of Virology, 3838–3847 (1995).

Sattar, D.A., et al., "Rotavirus inactivation by chemical disinfectants and antiseptics used in hospitals", *Can. J. Microbiol.* 29:1464–1469 (1983).

Vaughn, J.M., et al., "Inactivation fo Human and Simian Rotaviruses by Ozone," *Appl. Env. Microbiol.* 53(a):2218–2721 (1987).

Estes, M., et al., "Rotavirus Stability and Inactivation," *J.gem.Virol.*, 43:403–409 (1979).

Berman, D., et al., "Inactivation of Simian Rotaviruses by SA11 by Chlorine Dioxide, and Monochloramine," Applied and Environmental Microbiology, 317–323 (1984).

Tan, J., et al., "Inactivation of a Rotavirus By Disinfectants," Med. J. Aust, 1:19–23 (1981).

Chen, Y., et al, "Inactivation of Human and Simian Rotaviruses by Chlorine Dioxide," *Applied and Environmental Microbiology*, 1363–1366 (1990).

Matsui, S., et al., "Passive Protection against rotavirus–Induced Diarrhea by Monoclonal . . . ," J. of Clin. Microbilogy, 780–782 (1989).

Zissis, G., et al., "Protection Studies in Colostrum–Deprived Piglets of a Bovine Rotavirus . . . ,"*J. of Infectious Diseases*, 148(6):1061–1068 (1983).

Andrews, et al., "Vaccinia—rotavirus VP7 recombinants protect mice against rotavirus–induced diarrhea," *Vaccine*, 10(3):137–200 (1992).

Estes, Mary K., et al., *Journal of Virology*, 61(5):148–1494 (May 1987).

Smith, Gale E., et al., "Modification and secretion of human interluken 2 produced . . . ," *Proc. Natl. Acad. Sci.* USA, 82:8404–8408 (Dec. 1985).

Miyamoto, Chikara, et al., "Production of Human c=myc Protein Insect Cells Infected with a Baculovirus Expression Vector," *Molecular and Cellular Biology*, 5(10):2860–2865 (Oct. 1985).

Hambraeus, B. Anna M., et al., "Animal model of rotavirus infection in rabbis protection obtained without shedding of viral antigen," *Arch Virol*, 107:237–251 (1989).

Summers, Max D., et al., *Genetically Altered Viruses & The Environment.* Cold Spring Harbor Laboratory 1985. 319–331.

Brussow, Harald, et al., "Polypeptide Composition of Rotavirus Empty Capsids and Their Possible Use as a Subunit Vaccine," *J. Virol.*, 64:3635–3642.

Welch, Siao–Kun Wan, et al., "Rotavirus SA11 Genome Segment 11 Protein Is a Nonstructural Phosphoprotein," *j. Virol.*, 63:000–000 (1989).

Estes, Mary K., et al., "Synthesis and characterization of Rotavirus Capsid Antigens Using A Baculovirus Expression System," *Abstract U.S.—Japan Cooperative Medical Science Program*, Bethesda, Maryland Oct. 28–30, (1985).

Ward, C.W., "Structural Homologies between RNA Gene Segments 10 and 11 . . . ," *Virology*, 144(2):328–336 (1985).

Posses, R.D., "Cell–surface expression of influenza virus haemagglutinin in insect cells using a baculovirus vectors." *Virus Research*, 5:43–59 (1986).

Kuroda, K., et al., "Expression of the influenza virus haemagglutinin in insect cells by a baculovirus," *EmBD jour.* 5(6): 1359–1365 (1986).

Clark, et al., "Rotavirus Vaccines" 11, *Vaccines*, Plotkin, et al. Eds. W.B. Sounders Co., Philadelphia, 1988 pp 517–525.

Offit, et al., "Maternal Antibody—Mediated Protection Against Gastroenteritis Due . . . ," *J. Infect. Dis.* 152(6):1152–1158, (1985).

Daum, et al., "New Developments in Vaccines," Adv. Pediatr. Infect. Dis 6:1–57 (1991). (pp. 30–38 & 54–56 relevant to rotovirus enclosed.

Conner, et al., "Rotavirus Vaccines & Vaccination Potential" in *Current Topics in Microbiology and Immunology*, 185:286–326 (1994).

Both, G.W. et al., "Nucleotide sequence of the dsRNA segment 7 of Simian 11 rotavirus gene 8," *Nucleic ACIDS Research*, 12(3):1621–1625*(1984).

Both, G., et al., "A general strategy for cloning double–stranded BNA nucleotide sequence of the Simian–11 . . . ," *Nucleic Acids Research*, 10(22)7–75–7088 (1982).

Estes, Mary K., et al., Rotavirus Antigens, *Adv. Exp. Med. Biol.* 185:201–214 (1984).

* cited by examiner

FIG. 7A

Bar chart titled "CD1 MICE" showing % DIARRHEA vs nmol CROSS-LINKED NSP4 114-135 PEPTIDE:
- 0.1: 2/10 (~20%)
- 1: 8/10 (~80%)
- 10: 9/16 (~57%)
- 50: 8/10 (~80%)
- 100: 7/10 (~70%)
- 200: 8/10 (~80%)
- 250: 9/10 (~90%)
- 400: 8/9 (~90%)

FIG. 7B

Bar chart titled "Balb/C MICE" showing % DIARRHEA vs nmol CROSS-LINKED NSP4 114-135:
- 0.1: 2/6 (~33%)
- 10: 4/4 (100%)
- 50: 4/5 (~90%)
- 100: 5/5 (100%)

```
SEQ. ID. NO. 8 OSU-a    1  MDKLADLNYT LSVITLMNDT LHSIIQDPGM AYFPYIASVL TVLFTLHKAS
SEQ. ID. NO. 7 OSU-v    1  MDKLADLNYT LSVITLMNDT LHSIIQDPGM AYFPYIASVL TVLFTLHKAS

51  IPTMKIALKT SKCSYKVIKY CMVTIINTLL KLAGYKEQVT TKDEIEQQVD
                       51  IPTMKIALRT SKCSYKVIKY CIVTIINTLL KLAGYKEQVT TKDEIEQQMD

101  RIIKEMRRQL EMIDKLTTRE IEQVELLKRI HDKLAARSVD AIDMSKEFNQ
                      101  RIVKEMRRQL EMIDKLTTRE IEQVELLKRI HDKLVVRPVD AIDMSKEFNQ

151  KNIRTLDEWE SGKNPYEPSE VTASM
                      151  KNIRTLDEWE SGKNPYEPSE VTASM
```

FIG. 10

ROTAVIRUS ENTEROTOXIN NSP4 AND METHODS OF USING SAME

This application is a continuation-in-part of U.S. application Ser. No. 08/973,961 filed May 26, 1998 now U.S. Pat. No. 6,210,682, which was the National Stage Application PCT/US96/10523, filed Jun. 14, 1996, which claims the benefit of U.S. Provisional Application No. 60/000,220, filed Jun. 14, 1995 now abandoned.

This work was supported in part by Public Health Service Award DK 30114 from the National Institutes of Health.

FIELD OF THE INVENTION

This invention relates to the viral enterotoxin NSP4 and to methods for using it, or antibodies/antisera thereto, as diagnostic agents, vaccines and therapeutic agents for the detection, prevention and/or treatment of rotaviral disease, for the prevention of stunted growth in animals and children caused by rotaviral infection and for the treatment of cystic fibrosis. This invention also relates to methods and animal models for 1) the screening for viral enterotoxins, 2) the detection of viral enterotoxins and 3) the identification of viral enterotoxins.

BACKGROUND OF THE INVENTION

Rotaviruses are the leading cause of severe, life-threatening viral gastroenteritis in infants and animals (Kapikian et al., 1996) and are associated with sporadic outbreaks of diarrhea in elderly (Halvorsrud 1980) and immunocompromised patients (Holzel et al., 1980). These viruses have a limited tissue tropism, with infection primarily being restricted to cells of the small intestine (Estes et al., 1994). Rotavirus infections also cause morbidity and mortality in many animal species. Moreover, the outcome of infection is age-related; although rotaviruses may infect individuals and animals of all ages, symptomatic infection (i.e., diarrhea) generally occurs in the young (6 months—2 years in children, and up to 14 days in mice), and the elderly.

Age-related host factors which may influence the outcome of infection have been proposed to include 1) differences in the presence/quantity of virus-binding receptors on mature villus epithelial cells, 2) virus strains with a specific spike protein (VP4), 3) passive immunity acquired by maternal antibody or in colostrum, and 4) reduced levels of proteases in the young.

Disease resulting from rotavirus infection in mice has been studied more extensively than in any other species and an age restriction of disease has been reported by several investigators (Ramig 1988; Wolf et al. 1981; Riepenhoff-Talty et al., 1982). Only mice less than 14 days of age develop diarrhea following oral inoculation of murine rotavirus, and the peak age at which animals are most likely to develop diarrhea (6–11 days) corresponds to the age when rotavirus can bind to mouse enterocytes (Riepenhoff-Talty et al., 1982). Treatment of 8 day old mice with cortisone acetate which promotes premature maturation of intestinal epithelial cells, results in a reduced susceptibility to rotavirus-induced diarrhea, although the mice can still be infected (Wolf et al., 1981). These data were interpreted to suggest that the capacity of murine rotaviruses to induce diarrhea in young, but not adult mice, is due to the quantity of rotavirus-binding receptors on the surface of villus epithelial cells in the young mouse intestine.

When compared to rotavirus infections in other species, rotavirus infections in mice show minimal histologic alterations. That is, villus blunting is limited and transient, and crypt cell hyperplasia is not present. In addition, the loss of villus tip epithelial cells is more limited in mice than in other animals. Instead, vacuolization of enterocytes on the villus tips is a predominant feature in symptomatic rotavirus infection in mice and virus replication may be abortive (Greenberg et al., 1981). The lack of extensive pathologic alterations in the mouse intestine during symptomatic infections has remained a puzzle; one interpretation of this phenomenon is that a previously unrecognized mechanism of diarrhea induction may be active in symptomatic rotavirus infection in mice.

Despite the prevalence of rotavirus infections and extensive studies in several animal models and many advances in understanding rotavirus immunity, epidemiology, replication and expression, rotavirus pathogenesis, specifically, the mechanism of diarrhea induction, remains poorly understood. Proposed pathophysiologic mechanisms by which rotaviruses induce diarrhea following viral replication and viral structural protein synthesis include malabsorption secondary to the destruction of enterocytes (Graham et al., 1984), disruption of transepithelial ion homeostasis resulting in fluid secretion (Collins et al., 1988), and local villus ischemia leading to vascular damage and diarrhea (Osborne et al., 1988). However, these proposed mechanisms do not explain cases of rotavirus-induced diarrhea observed prior to, or in the absence of, histopathologic changes (Theil et al., 1978; McAdaragh 1980; Saif et al., 1976).

On the other hand, the pathophysiology of bacterial-induced diarrhea based on interactions with intestinal receptors and bacterial enterotoxins is well understood (Burges et al., 1978; Gianella et al., 1981; Krause et al., 1990). The heat-stable toxin A and the heat-labile toxin of *E. coli*, and guanylin (an endogenous, 15 amino acid intestinal ligand originally isolated from rat jejunum) induce diarrhea by binding a specific intestinal receptor, increasing cAMP or cGMP, and activating a cyclic nucleotide signal transduction pathway (Giannella et al., 1993; Currie et al., 1992; Field et al., 1978; Forte et al., 1992). The net effect of these bacterial toxins is to increase $Cl^-$ secretion, and decrease $Na^+$ and water absorption.

Previous studies in insect cells indicated that a receptor-mediated phospholipase C pathway is associated with the increases in $[Ca^{2+}]_i$, following exogenous treatment of cells with NSP4 or NSP4 114–135 peptide (Tian et al., 1994). The rotavirus nonstructural ER glycoprotein, NSP4, has been shown to have multiple functions including the release of calcium from the endoplasmic reticulum (ER) in SF9 insect cells infected with recombinant baculovirus containing the NSP4 cDNA (Tian et al., 1994; Tian et al., 1995). In addition, NSP4 disrupts ER membranes and may play an important role in the removal of the transient envelope from budding particles during viral morphogenesis. NSP4 114–135, a 22 aa peptide of NSP4 protein, has been shown to be capable of mimicking properties associated with NSP4 including being able to (i) mobilize intracellular calcium levels in insect cells when expressed endogenously or added to cells exogenously (Tian et al., 1994; Tian et al., 1995), and (ii) destabilize liposomes.

Expression of NSP4 in insect cells increased $[Ca^{2+}]_i$ levels from a subset of the thapsigargin-sensitive store (ER) (Tian et al., 1995). The $[Ca^{2+}]_i$ mobilized by NSP4 or the NSP4 114–135 peptide added exogenously to cells was blocked by a phospholipase C inhibitor, the U-73122 compound, suggesting that a receptor-mediated pathway is responsible for the calcium release from the ER induced by NSP4 (Tian et al., 1995). The $[Ca^{2+}]_i$ mobilized by NSP4 expressed intracellularly was not blocked by the U-73122 compound, suggesting that a second pathway is responsible for the calcium release from the ER induced by intracellular NSP4 (Tian et al., 1995).

SUMMARY OF THE INVENTION

The present invention discloses herein a method of immunization against rotavirus infection or disease comprising administering to a subject a peptide NSP4 112–175 or NSP4 112–150 or a toxoid thereof. Further, the present invention discloses a method of immunization against rotavirus infection or disease comprising administering to a subject a non-gylcosylated NSP4 protein or a toxoid of NSP4. The immunizations may result in both homotypic and heterotypic immunity.

In another specific embodiment, it is also provided a method of passive immunization against rotavirus infection comprising administering to an expectant mother a peptide NSP4 112–175, NSP4 112–150 or a toxoid thereof. Yet further, the present invention discloses a method of passive immunization against rotavirus infection comprising administering to an expectant mother a non-gylcosylated NSP4 protein or a toxoid of NSP4. The immunizations may result in both homotypic and heterotypic immunity.

A specific embodiment of the present invention is that the NSP4 peptide (e.g., NSP4 112–175 or NSP4 112–150) or toxoid is produced by a synthetic method. In a further specific embodiment, the NSP4 peptide or toxoid is produced by an expression vector. The expression vector is selected from the group consisting of mammalian, yeast, bacterial or insect.

Another embodiment of the present invention is a fusion protein comprising a protein that forms a virus-like particle linked to a NSP4 peptide. The fusion protein further comprises a linker sequence. An exemplary linker sequence includes, but is not limited to, three alanine residues and an alanine and serine residue. It is also contemplated that three glycine residues may be substituted for the three alanine residues. One of skill in the art is cognizant that the scope of the invention is not limited to a five residue linker. It is contemplated that other linkers may be used, for example, but not limited to, three alanine residues or 3 glycine residues. The NSP4 peptide is NSP4 112–175 or a toxoid thereof or NSP4 112–150 or a toxoid thereof. The protein that forms a virus-like particle is a viral protein or peptide isolated from the viral families Caliciviridae or Reoviridae.

In specific embodiments, the viral protein isolated from Caliciviridae is a Norwalk virus protein or peptide. In two particular fusion proteins, the Norwalk virus protein is ORF2 or ORF2 plus ORF3 or a fragment or toxoid of ORF2 or ORF2 plus ORF3. Specifically, ORF2 comprises amino acids 21–530 and ORF3 comprises 1–212.

In yet another specific embodiment, the viral protein or peptide isolated from Reoviridae is a rotavirus protein or peptide. More particularly, the rotavirus peptide is selected from the group of rotavirus proteins consisting of VP2, VP4, VP6 and VP7. In specific embodiments, the rotavirus peptide is VP2 or a VP2 fragment. Specifically VP2 comprises amino acids 94–881.

Another embodiment of the present invention discloses an expression vector comprising a nucleic acid sequence encoding a fusion protein operatively linked to a first promoter sequence, and a nucleic acid sequence encoding a viral peptide that is part of a virus-like particle operatively linked to a second promoter sequence. The fusion protein comprises a viral peptide that is part of a virus-like particle linked to a NSP4 peptide. The viral peptide linked to the NSP4 peptide is VP2 and forms the inner shell of the virus-like partilce. The viral peptide that is not linked to the fusion protein is rotavirus VP6. This peptide forms the outer shell of the virus-like particle surrounding the VP2 shell. The first promoter sequence is a polyhedrin promoter sequence and the second promoter sequence is a p10 promoter sequence. The expression vector is selected from the group consisting of insect, mammalian, viral and bacterial In specific embodiments, the expression vector comprises a fusion protein that comprises a nucleic acid sequence encoding rotavirus VP2 amino acids 94–881 linked to a nucleic acid sequence encoding NSP4 amino acids 112–175.

In another embodiment, the expression vector comprises a fusion protein that comprises a nucleic acid sequence encoding rotavirus VP2 amino acids 94–881 linked to a nucleic acid sequence encoding NSP4 amino acids 112–150.

Another embodiment of the present invention comprises an expression vector comprising a nucleic acid sequence encoding a fusion protein, wherein the fusion protein comprises a viral peptide that is part of a virus-like particle linked to a NSP4 peptide. The nucleic acid sequence is operatively linked to a promoter sequence.

In specific embodiments, the expression vector comprises the fusion protein that comprises a nucleic acid sequence encoding Norwalk virus ORF2 linked to a nucleic acid sequence encoding NSP4 amino acids 112–175. In a further embodiment, the fusion protein comprises a nucleic acid sequence encoding Norwalk virus ORF2 linked to a nucleic acid sequence encoding NSP4 amino acids 112–150. It is also contemplated that the fusion protein may be a fragment of Norwalk virus ORF2 linked to NSP4 amino acids 112–175 or a fragment of Norwalk virus ORF2 linked to NSP4 amino acids 112–150.

In another embodiment, the expression vector comprises the fusion protein that comprises a nucleic acid sequence encoding a nucleic acid sequence encoding Norwalk virus ORF2 and ORF3 linked to NSP4 amino acids 112–175. In another embodiment the fusion protein comprises a nucleic acid sequence encoding Norwalk virus ORF2 and ORF3 linked to a nucleic acid sequence encoding NSP4 amino acids 112–150. It is also contemplated that the fusion protein may be a fragment of Norwalk virus ORF2 and ORF3 linked to NSP4 amino acids 112–175 or a fragment of Norwalk virus ORF2 and ORF3 linked to NSP4 amino acids 112–150.

A specific embodiment of the present invention also comprises a vaccine for inducing the formation of protective antibodies against rotavirus infection comprising administering a chimeric virus-like particle. The chimeric virus-like particle comprises a peptide NSP4 112–175, a first viral protein that is part of a virus-like particle, and a second viral protein that is part of a virus-like particle. Specifically, the first viral protein is rotavirus VP2, which forms an inner shell and said second viral protein is rotavirus VP6, which forms an outer shell surrounding the VP2 shell.

In another embodiment, it is also provided a method of immunization against rotavirus infection or disease comprising the step of administering to a subject a compound comprising a chimeric virus-like particle. The chimeric virus-like particle comprises a peptide NSP4 112–175, a first viral protein that is part of a virus-like particle, and a second viral protein that is part of a virus-like particle. More particularly, the first viral protein is rotavirus VP2 and said second viral protein is rotavirus VP6. The compound is administered orally, parenterally or intranasally. Another aspect comprises that the compound is administered with an adjuvant.

In specific embodiments, the compound is simultaneously or consecutively administered by at least two different routes of administration. Exemplary routes of administration include, but are not limited to, oral, parenteral or intranasal.

Another embodiment of the present invention comprises a method of inducing an immune response comprising the step of administering to a mammal one expression vector, wherein said expression vector comprises a nucleic acid sequence encoding a fusion protein, wherein said fusion protein comprises a first viral protein that is part of a virus-like particle linked to a NSP4 nucleic acid sequence, and a nucleic acid sequence encoding a second viral protein that is part of a virus-like particle. In specific embodiments, the nucleic acid sequence encoding the fusion protein and the nucleic acid sequence encoding the second viral protein are under separate transcriptional control and wherein the nucleic acid sequence encoding the fusion protein and the nucleic acid sequence encoding the second viral protein are in tandem in the one expression vector.

A specific embodiment also provides a method of inducing an immune response comprising the steps of co-administering to a mammal or a cell two different expression vectors, wherein a first expression vector comprises a nucleic acid sequence encoding a first viral protein that is part of a virus-like particle and a second expression vector comprises a nucleic acid sequence encoding a fusion protein, wherein said fusion protein comprises a second viral protein that is part of a virus-like particle linked to a NSP4 nucleic acid sequence.

Other embodiments, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows rotavirus NSP4 protein induces diarrhea in CD1 mice. 0.1 to 5 nmols (2–100 $\mu$M) of purified NSP4 was administered by the IP or IL routes to 6–7, 8–9 and 17–18 day old CD1 pups. Rotavirus protein VP6 was used as the control in 6–7 day old animals, the most sensitive. The dose and route of the proteins, age of the animals, and mean diarrhea score (mean score) are indicated on the bottom of the graph. The Y axis displays the % diarrhea. Above each column is the number of responders (mice with diarrheal disease) over the total number of animals tested.

FIG. 2 shows IP administration of NSP4 induces diarrhea in 6–7 day old CD-1 pups. 0.04 to 1.0 nmols (1–25 $\mu$g) of purified NSP4 protein was administered to 6–7 day old CD1 pups by the IP route. The dose administered, in nanomoles and in micrograms, is shown on the X-axis. The percentage of pups that display diarrhea in response to the administered dose is shown on the Y-axis. Above each column the number of responders (pups with diarrhea) over the total number of animals receiving treatment is shown.

FIG. 3 shows diarrheal response in CD1 mice following IP administration of NSP4 114–135 peptide. Young (6–7 day) mouse pups were injected with various doses of peptide (x axis) and monitored for disease. The number of responders over the total number animals tested is shown above each column. With the CD1 mice, 0.1–50 nmol (2 $\mu$M-1 mM) of peptide elicited similar responses (30–40% diarrhea induction); and 100–400 nmols (2–8 mM) of peptide elicited comparative responses with 60–70% of the animals sick.

FIG. 4 shows diarrheal response in Balb/C mice following IP administration of NSP4 114–135 peptide. Young (6–7 day) mouse pups were injected with various doses of peptide (x axis) and monitored for disease. The number of responders over the total number animals tested is shown above each column.

FIG. 5 shows IP delivery of NSP4 114–135 peptide induce an age-dependent diarrhea in CD1 mice and Spraque-Dawley Rats. Different age outbred mice and rats were inoculated (IP) with NSP4 114–135 peptide and evaluated for disease. The age and species of the pups, dose of the synthetic peptide and indication of whether peptides were unlinked or cross-linked are indicated on the bottom of the graph. The dose of the IP delivered peptide varied with the age of the animals, i.e., older animals received a higher dose to control for the differences in body weight. The Y axis indicates the % diarrhea and above each column is indicated the number of responders over the total number of animals inoculated. The peptide was diluted in sterile PBS and evaluated for sterility. A final volume of 50 $\mu$l per dose was used.

FIG. 6 shows IL delivery of NSP4 114–135 peptide induce an age-dependent diarrhea in CD1 mice and Spraque-Dawley Rats. Different age outbred mice and rats were inoculated (IL) with NSP4 114–135 peptide and evaluated for disease. The age and species of the pups, dose of the synthetic peptide and indication of whether peptides were unlinked or cross-linked are indicated on the bottom of the graph. The Y axis indicates the % diarrhea and above each column is indicated the number of responders over the total number of animals inoculated. The peptide was diluted in sterile PBS and evaluated for sterility. A final volume of 50 $\mu$l per dose was used.

FIG. 7A and FIG. 7B shows the dose response for cross-linked NSP4 peptide delivered ip to 6–7 day old CD1 and Balb/C Mice. The NSP4 114–135 peptide was cross-linked to itself with glutaraldehyde and dialyzed against sterile PBS prior to IP delivery to CD1 (FIG. 7A) and Balb/C (FIG. 7B) mice. The number of responders over the total number of animals inoculated is shown above each column.

FIG. 8 illustrates the experimental designs to test the ability of NSP4 114–135 to induce protective immunity from infectious rotavirus challenge and the ability of NSP4-specific antibody to mitigate rotavirus diarrhea following infection. The left hand side of the figure illustrates that mouse dams were immunized with NSP4 peptide or with control peptide and then bred. Pups born to the dams were orally challenged with virulent rotavirus at 6–7 days. The right hand side of the figure illustrates how pups born to non-immunized dams were first orally challenged with virulent rotavirus, followed by oral gavage of NSP4-specific or control antisera. The results of these experiments are set forth in Tables 5 and 6.

FIG. 9 shows the results from an experiment to study the differences in weight and growth between normal animals and animals suffering from NSP4 114–135-induced diarrhea.

FIG. 10 shows the amino acid sequence comparison of NSP4 from OSU attenuated and OSU virulent virus. The amino acid sequence of the NSP4 protein of OSU-a (a porcine rotavirus, tissue culture attenuated, avirulent strain, SEQ.ID.NO:7), top line, is compared to the amino acid sequence of the NSP4 protein of OSU-v (a porcine rotavirus, virulent strain, SEQ.ID.NO:8), bottom line. Positions at which the two sequences are different are shown in bold.

Figure 11:
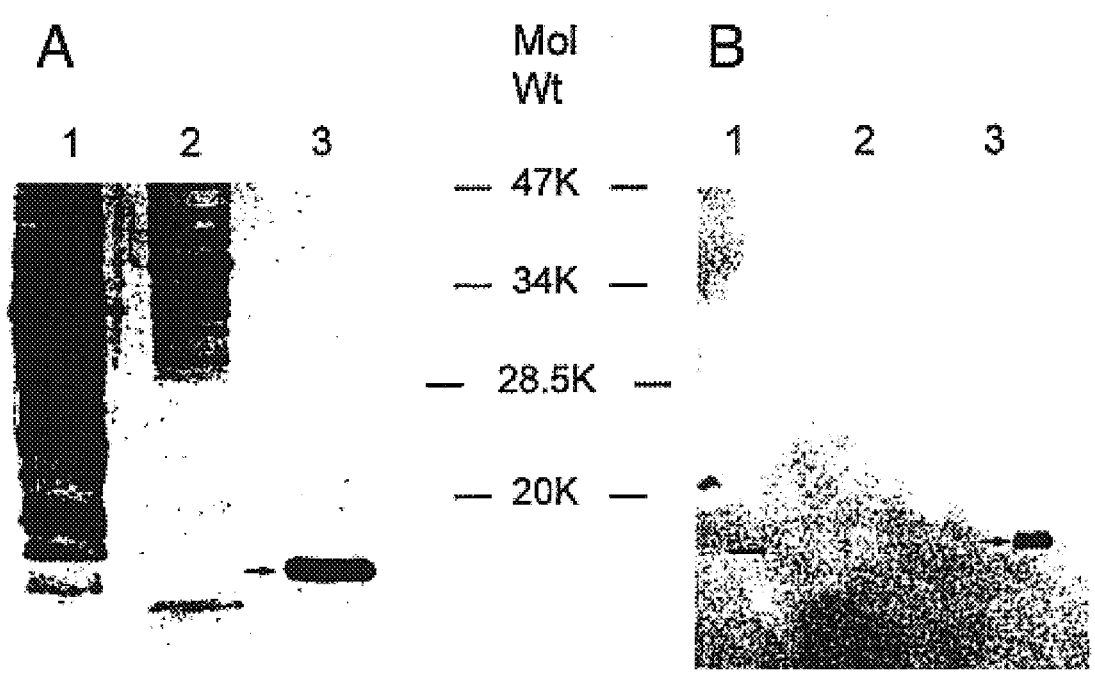

FIG. 11A and FIG. 11B show purity of NSP4 112–175 and its interaction with an antiserum raised with synthetic SA11 NSP4 peptide 114–135. FIG. 11A illustrates the silver stained SDS-15% polyacrylamide gel of purified NSP4 112–175. FIG. 11B illustrates the Western blot of purified NSP4 112–175 tested by rabbit antiserum against synthetic SA11 NSP4 peptide 114–135 (1:300 dilution). Lane 1, NSP4 112–175 crude material. Lane 2, eluate from immune affinity column against baculoviral proteins. Lane 3, 0.5 μg of purified NSP4 112–175. Arrows indicate NSP4 112–175.

Figure 12:
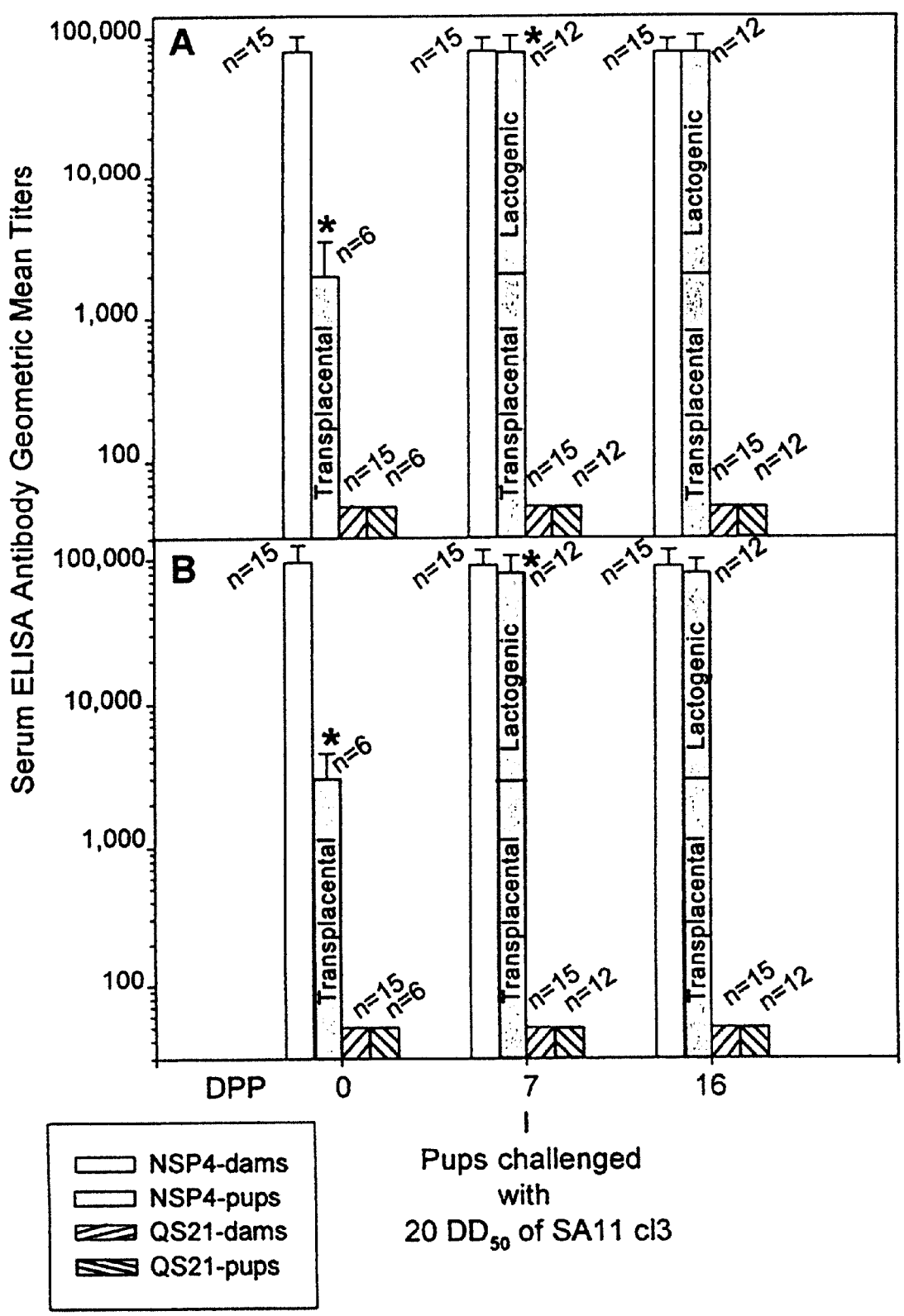

FIG. 12A and FIG. 12B show the serum antibody responses in dams and pups to parenterally administered NSP4 112–175. Mice were immunized three times with 15 μg of NSP4 aa 112–175 plus 20 μg of QS-21 or with 20 μg of QS-21 alone. Blood samples were collected at 0, 7, and 16 DPP. FIG. 12A shows the serum antibody titers against NSP4 112–175. FIG. 12B shows the Serum antibody titers against full-length NSP4. Bars: NSP4 dams, immunized with NSP4 112–175 plus QS-21; NSP4-pups: delivered to an nursed by NSP4-dams; QS-21-dams, inoculated with QS-21 alone; QS-21-pups: delivered to and nursed by QS-21-dams.

Figure 13:
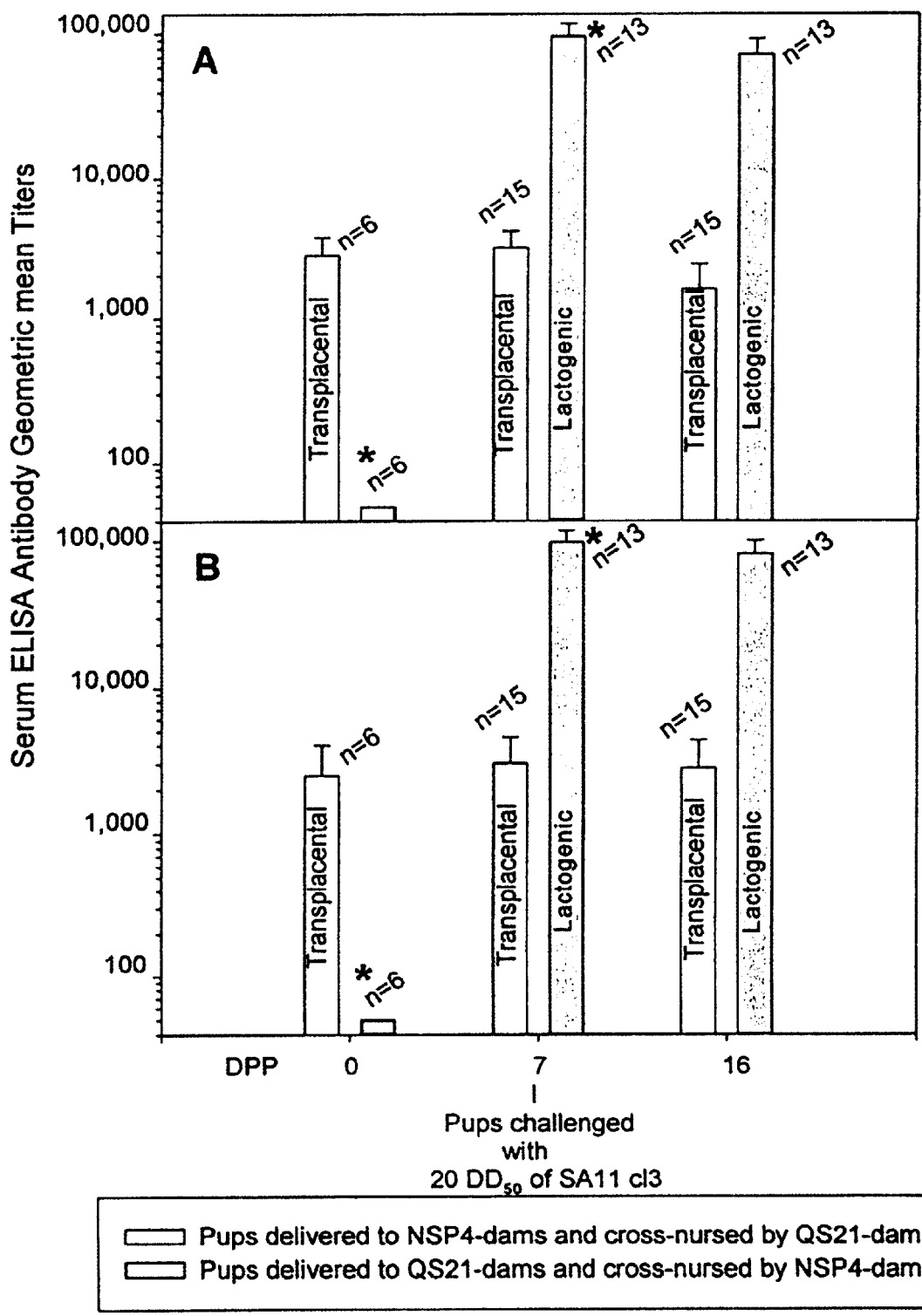

FIG. 13A and FIG. 13B show the serum antibody responses in pups during cross-nursing. FIG. 13A illustrates the serum antibody titers to NSP4 112–175 in pups. FIG. 13B illustrates the serum antibody titers to full-length NSP4 in pups. Blood samples were collected on 0, 7, and 16 DPP.

Figure 14:
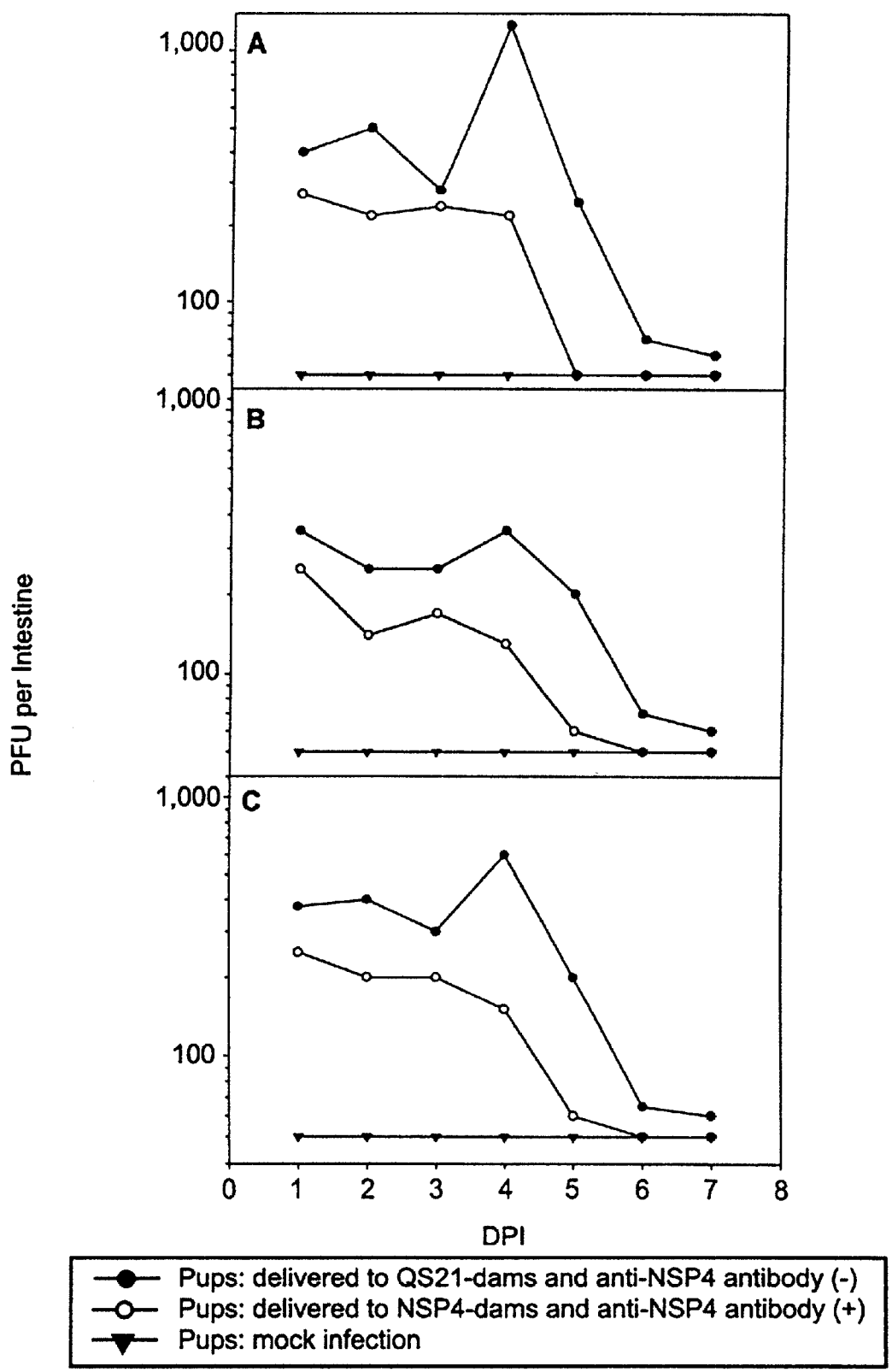

FIG. 14A, FIG. 14B and FIG. 14C show replication of simian rotavirus SA11 in seven-day-old mice. SA11, at a dose of 20 $DD_{50}$ was orally gavaged in seven-day-old BALB/c mice born to NSP4 dams with QS-21 dams. Titers of infectious virus in the combined small and large intestine homogenates were determined at various days postinfection by plaque assay. The limit of virus detection was about 50 PFU/ml. -●-, virus titers in intestinal homogenates from QS-21-pups. -○-virus titers in intestinal homogenates from NSP4-pups. -▲-, baseline of intestines from pups with mock infection. FIG. 14A and FIG. 14B show the virus titers from 2 individual experiments and each experiment was composed of one inoculated and one control pup 1–7 DPI. FIG. 14C shows the average virus titers given in FIG. 14 A and FIG. 14B.

Figure 15:
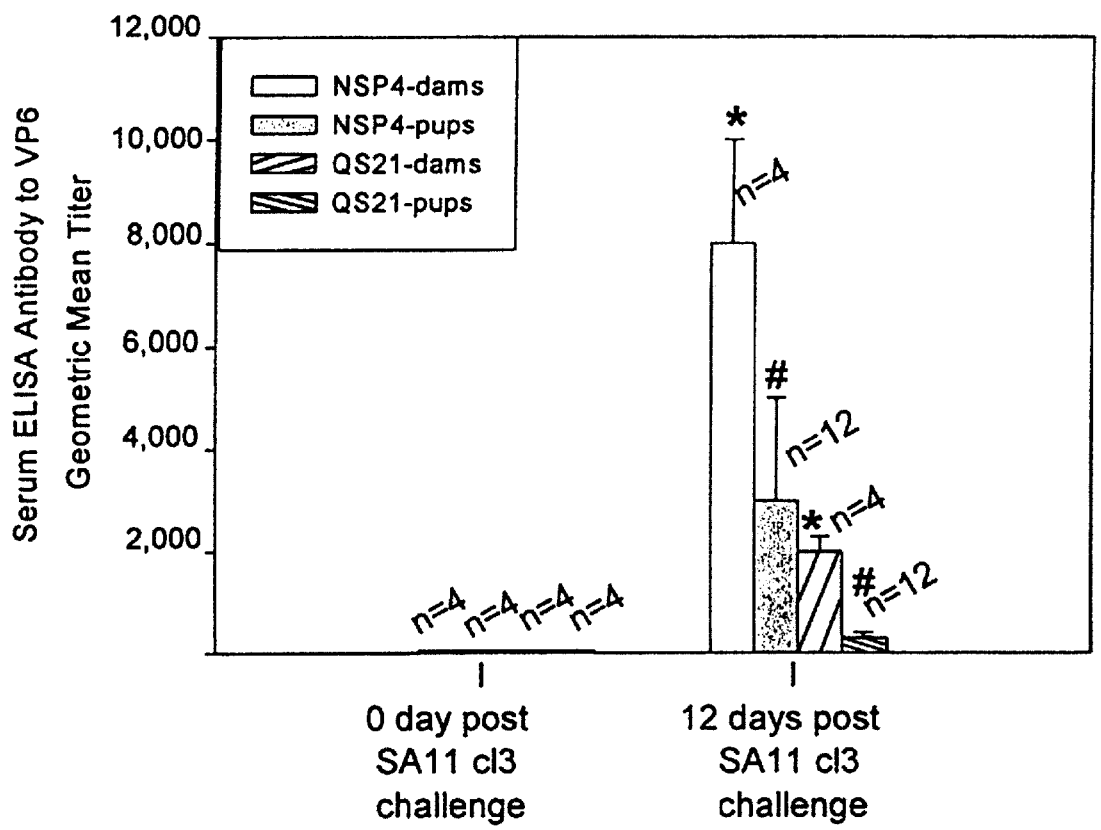

FIG. 15 shows serum antibody responses against SA11 VP6 in dams and pups with or lacking antibody to NSP4 112–175 and challenged with a single dose of rotavirus SA11. Pups were challenged with a single dose of 20 $DD_{50}$ of SA11. Blood samples were collected on 0 DPI and 12 DPI. Bars: Bars: NSP4 dams, immunized with NSPA4 112–175 plus QS-21; NSP4-pups: delivered to an nursed by NSP4-dams; QS-21-dams, inoculated with QS-21 alone; QS-21-pups: delivered to and nursed by QS-21-dams. n, number of mice per group. The antibody GMT between NSP4-pups and QS-21-pups were 3000 vs. 300.

Figure 16:
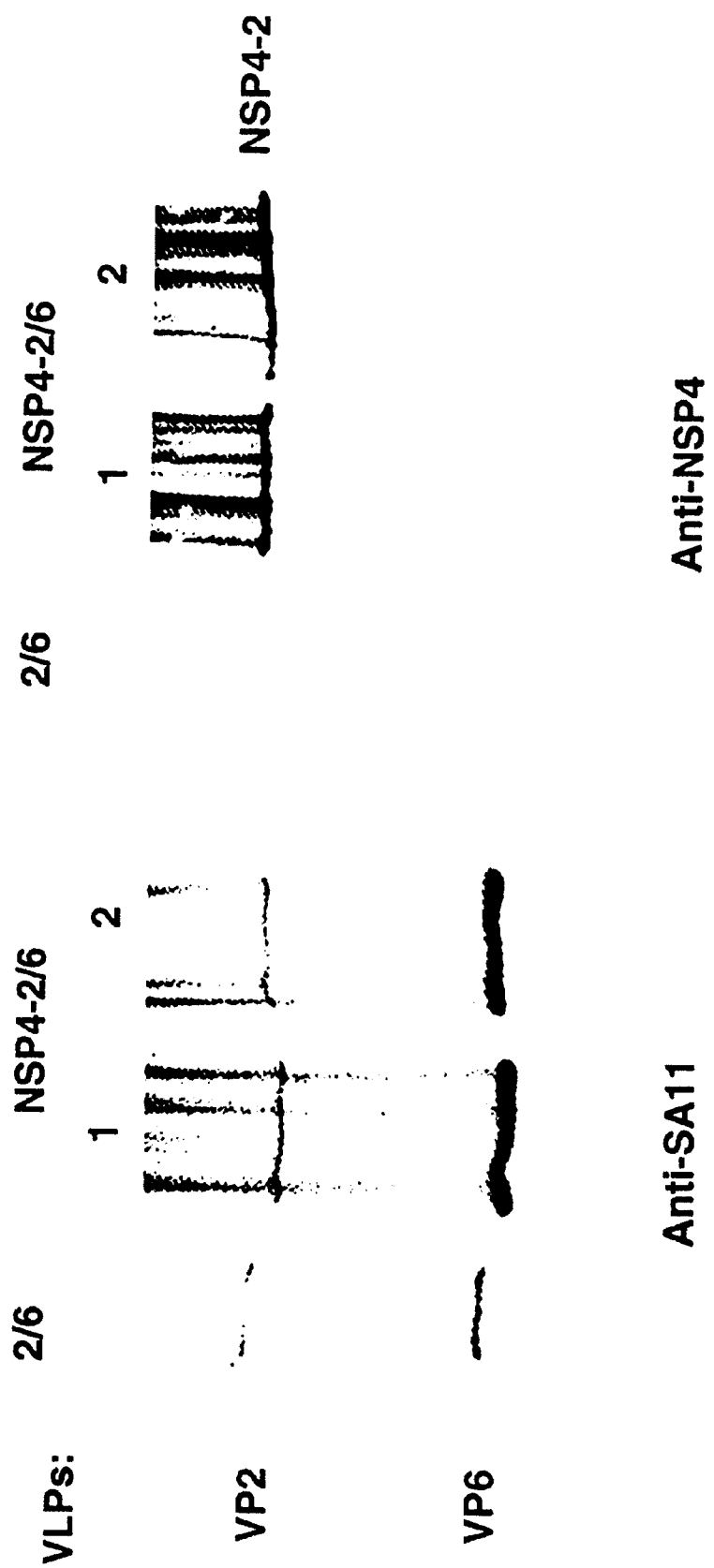

FIG. 16 shows a Western blot analysis of NSP4-2/6-VLPs. A fusion protein was constructed comprising NSP4 112–175 and aa 94–881 of VP2. The fusion was inserted into a baculovirus expression vector pBAC4x-1. Cells were transiently transfected with the expression vector. Virus-like particles were expressed, purified, and analyzed by Western blot.

Figure 17:
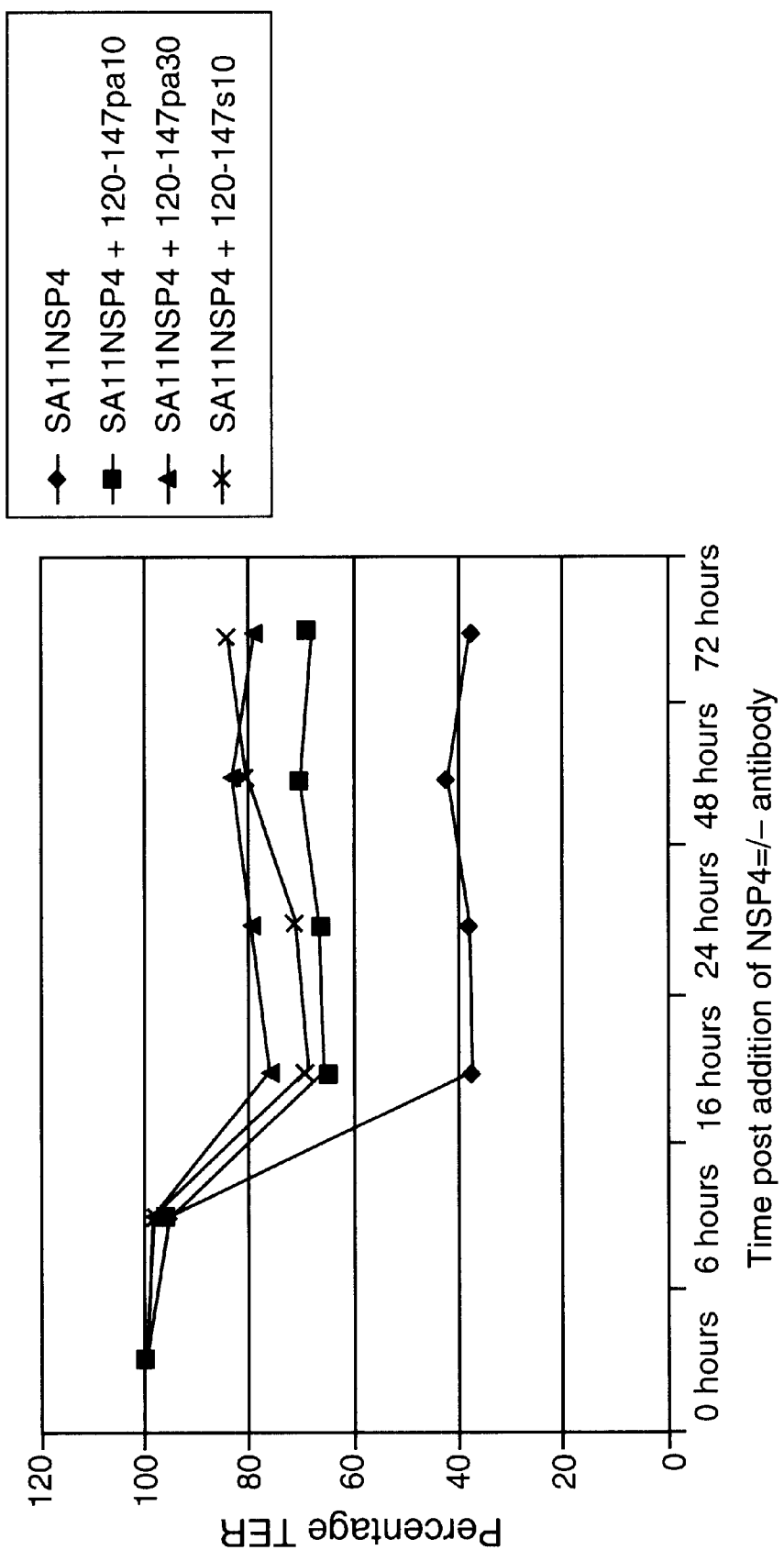

FIG. 17 shows the effect of NSP4 on transepitherlial resistance (TER) of MDCK-1 cells and neutralization by antibody. This is an in vitro assay that mimics the effect of antibody on induction of diarrhea in mice.

DETAILED DESCRIPTION OF THE INVENTION

This invention stems from the discovery of the first known viral enterotoxin, rotavirus NSP4, previously called NS28, which encodes a viral toxin capable of inducing intestinal secretion through a heretofore unknown signal transduction pathway to cause diarrheal disease.

The present invention relates to the fortuitous discovery that the rotavirus nonstructural ER glycoprotein, NSP4, induces an age-dependent diarrhea in two rodent models. Induction of diarrhea following administration of this protein alone was completely unexpected because infection with rotavirus was not involved. Characterization of the parameters of these new models of rotavirus-induced diarrhea demonstrates that this enteric viral-encoded protein is an enterotoxin, similar to bacterial enterotoxins, which are well-known to induce diarrhea by stimulating signal transduction pathways following interaction with specific intestinal receptors. The ordinary practitioner will appreciate that these new findings on NSP4-induced diarrheal disease and the data presented herein support several novel therapeutic and preventive approaches to rotavirus-induced disease.

The present invention also demonstrates that a synthetic peptide corresponding to amino acids 114–135 of SA11 NSP4 also induces an age-dependent diarrhea in young mice comparable to NSP4 when administered by the IP and IL route. Since the NSP4 114–135 peptide was readily available in large amounts in pure form, the response to the peptide was studied in detail. The response to the peptide was specific as shown by 1) lack of response to control peptides, 2) blocking with peptide-specific antibody, and 3) a mutated peptide (differing by only a single residue) alone failed to induce the response. The concentration of peptide required for disease induction was considerably higher than that needed for a response to the protein. Because the entire protein possesses more potent activity than the peptide, other peptides from this protein which have the same effect are also included in the present invention. These peptides include, but are not limited to, NSP4, non-glycosylated NSP4, NSP4 114–135, 120–147, 112–175 or 112–150. Also contemplated in the present invention is the use of toxoids of the above listed NSP4 proteins or peptides.

Specifically, proteins and or peptides according to the present invention may contain the entire amino acid sequence of NSP4 protein or any other fragment of NSP4 as set forth herein. The following amino acid sequences are sequences corresponding to NSP4 proteins and are within the scope of the invention and some are referenced with the corresponding GenBank Accession Numbers-: SA11 (SEQ.ID.NO:11, AAC61867); SA11 clone 3 (SEQ.ID.NO:12); Murine EC (SEQ.ID.NO:13, AAB58700); Porcine OSU (SEQ.ID.NO:7, BAA13728); Gott-v (SEQ.ID.NO:14) and Gott-a (SEQ.ID.NO:15).

Further, the present invention illustrates an analogous age dependence in the induction of diarrhea with purified NSP4 protein and NSP4 114–135 peptide. Mice were most sensitive to the effects of the protein or peptide at 6–7 days of age. Diarrhea induction by NSP4 or NSP4 114–135 decreased as the age of the animal increased, regardless of the route of administration. Hence the observed diarrhea in this study mimics the properties of symptomatic infection observed in experimental and natural rotavirus infection.

The present invention also shows that the inoculation of NSP4 114–135 peptide-specific antiserum prior to IP delivery of peptide results in a dramatic reduction of disease. (90% reduction in disease).

Further, the present invention shows that diarrheal disease in pups born to dams immunized with the NSP4 114–135 and NSP4 112–175 peptide is significantly reduced in severity, duration, and in the number of pups with diarrhea. Further, the present invention demonstrates that immunization of dams with highly pure NSP4 112–175 induces passive protection of suckling mice against diarrhea induced by challenge viruses homotypic or heterotypic to the NSP4 112–175 immunogen.

Yet further, post-infection administration of NSP4-specific antibody significantly reduces diarrheal disease.

One skilled in the art realizes that these data, showing that NSP4 protein or NSP4 114–135 and NSP4 112–175-specific antibodies are sufficient to block the induction or severity of diarrhea, demonstrate that NSP4, NSP4 114–135 or NSP4 112–175 and/or antibodies specific thereto will be useful as vaccines and as therapeutic agents. Additionally, new drugs can now be developed to block or minimize the effects of interaction of NSP4 with its receptor or the effects of the disruption of the calcium homeostasis in affected cells.

In accordance with the foregoing and with the disclosure that follows, it is an embodiment of the present invention to provide a method for the screening and identification of viral enterotoxins associated with rotavirus and other gastroenteritis viruses, such as caliciviruses, astroviruses, enteric adenoviruses, coronaviruses, and parvoviruses, including administering expressed proteins or peptides or synthetic peptides of such viruses to animals and monitoring the animals for diarrhea. For the purpose of this and other embodiments of the invention, human volunteers shall be considered to be within the scope of "animals." It is a further embodiment of the present invention to provide methods for the screening and identification of new viral enterotoxins including administration of expressed proteins or peptides or synthetic peptides to CD1 mice, Balb/C mice and/or Sprague-Dawley rats and monitoring for diarrhea.

To the extent that the meaning of the term "diarrhea-genic viral protein" may be construed to differ from the meaning of the term viral enterotoxin, if the term "diarrhea-genic viral protein" is substituted for the term viral enterotoxin, the subject matter of this and all following embodiments and all claims is also considered to be within the scope of the invention, and fully described for all purposes.

It is another embodiment of the present invention to provide a method for the screening for and identification of viral enterotoxins associated with viruses that are not known as diarrhea or gastroenteritis virus, but that are associated with diarrhea as a consequence of infection. Without limiting the invention, examples include human immunodeficiency virus (HIV) and cytomegalovirus (CMV). This method includes administering expressed proteins or peptides or synthetic peptides of a selected virus to animals and monitoring the animals for diarrhea.

In certain embodiments, the present invention provides antibodies that bind with high specificity to NSP4 or fragments thereof (i.e., NSP4 114–135, NSP4 120–147, NSP4 112–175 or NSP4 112–150) provided herein. As detailed above, in addition to antibodies generated against NSP4, antibodies may also be generated in response to smaller constructs comprising epitopic core regions, including wild-type and mutant epitopes.

It is another embodiment of the present invention to provide a method for treatment of diarrheal disease, including reducing the severity of diarrhea caused by viral infection, including administering antibodies to viral enterotoxins to a subject with diarrhea or known, or suspected to be infected by or to have been exposed to a gastroenteritis virus. For the purpose of this invention, antibodies shall mean polyclonal and monoclonal antibodies unless otherwise indicated. Methods for the preparation of polyclonal and monoclonal antibodies to any protein or peptide are well known to the practitioner having ordinary skill in the art.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference). Generally, IgG and/or IgM are preferred because they are the most common antibodies in the physiological situation and because they are most easily made in a laboratory setting. Another antibody that is important for mucosal protection is IgA. IgA functions as the primary antibody that is present in body secretions, such as saliva, tears, breast milk, gastrointestinal secretions and mucus secretions of the respiratory and genitourinary tracts.

"Humanized" antibodies are also contemplated, as are chimeric antibodies from mouse, rat, or other species, bearing human constant and/or variable region domains, bispecific antibodies, recombinant and engineered antibodies and fragments thereof.

Antibodies, both polyclonal and monoclonal, specific for isoforms of antigen may be prepared using conventional immunization techniques, as will be generally known to those of skill in the art. A composition containing antigenic epitopes of the NSP4 protein, peptide or fragments thereof of the present invention can be used to immunize one or more experimental animals, such as a rabbit or mouse, which will then proceed to produce specific antibodies against the compounds of the present invention. One skilled in the art realizes that fragments of NSP4 protein include, but are not limited to NSP4 114–135, NSP4 120–174, NSP4 112–175 or NSP4 112–150. Polyclonal antisera may be obtained, after allowing time for antibody generation, simply by bleeding the animal and preparing serum samples from the whole blood.

Briefly, a polyclonal antibody is prepared by immunizing an animal with an immunogen comprising a NSP4 polypeptide or fragment thereof (i.e., NSP4, NSP4 114–135, NSP4 120–174, NSP4 112–175 or NSP4 112–150) and collecting antisera from that immunized animal. A wide range of animal species can be used for the production of antisera. Typically an animal used for production of anti-antisera is a non-human animal including rabbits, chickens, mice, rats, hamsters, pigs or horses. Because of the relatively large blood volume of rabbits, a rabbit is a preferred choice for production of polyclonal antibodies.

It is another embodiment of the present invention to provide monoclonal antibodies to NSP4 protein, to NSP4 114–135 peptide, to NSP4 120–147 peptide, to NSP4 112–175 peptide, to NSP4 112–175 and to other peptides of NSP4.

Monoclonal antibodies (MAbs) are recognized to have certain advantages, e.g., reproducibility and large-scale production, and their use is generally preferred. Monoclonal antibodies may be readily prepared through use of well-known techniques, such as those exemplified in U.S. Pat.

No. 4,196,265, incorporated herein by reference. Typically, this technique involves immunizing a suitable animal with a selected immunogen composition, e.g., a purified or partially purified NSP4 protein, polypeptide or peptide or cell expressing high levels of NSP4. One skilled in the art realizes that NSP4 protein or polypeptide includes, but is not limited to, NSP4 114–135, NSP4 120–174, NSP4 112–175 or NSP4 112–150. The immunizing composition is administered in a manner effective to stimulate antibody producing cells. Rodents such as mice and rats are preferred animals, however, the use of rabbit, sheep, human, monkey, rabbit, chicken, chicken eggs or frog cells is also possible. The use of rats may provide certain advantages (Goding 1986), but mice are preferred, with the BALB/c mouse being most preferred as this is most routinely used and generally gives a higher percentage of stable fusions.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to NSP4, NSP4 114–135, NSP4 120–174, NSP4 112–175 or NSP4 112–150 antigen epitopes. Additionally, it is proposed that monoclonal antibodies specific to the particular NSP4 protein or polypeptide (i.e., NSP4 114–135, NSP4 120–174, NSP4 112–175 or NSP4 112–150) of different species may be utilized in other useful applications.

The present invention also contemplates the use of antibodies against NSP4 proteins, polypeptides or fragments thereof (i.e., NSP4 114–135, NSP4 120–174, NSP4 112–175 or NSP4 112–150), generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins".

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging".

Antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

Another embodiment of the present invention is to provide a method of using NSP4 and the peptides thereof, including but not limited to NSP4 114–135, NSP4 120–147, NSP4 112–175 and NSP4 112–150 to measure the levels of antibodies to NSP4. These antibody measurements may be a surrogate for measuring protective immunity. For example, NSP4 and peptides thereof may be used to measure binding of antibodies, such as in an ELISA, or to measure neutralizing antibodies, such as in a transepithelial resistance assay (TER). Thus, it is contemplated that these type of in vitro methods (antibody binding and antibody neutralization) may correlate to protective immunity.

It is another embodiment of the present invention to provide a method for the prevention or amelioration of diarrhea caused by rotavirus infection including administration of antibodies to NSP4 protein or peptides thereof, including but not limited to NSP4 114–135, NSP4 120–147, NSP4 112–175 and NSP4 112–150. As rotavirus infection is transmitted rapidly, this method is considered to include the prevention or amelioration of disease following exposure to a known infected person, for example in day care centers and in hospitals.

For the purpose of this invention, the term "compound comprising amino acids in a sequence corresponding to NSP4 114–135" shall mean a compound which has within it a sequence of amino acids corresponding to the sequence of NSP4 114–135, including NSP4 114–135 and the NSP4 protein. For the purpose of this invention, the term "compound comprising amino acids in a sequence corresponding to NSP4 120–147" shall mean a compound which has within it a sequence of amino acids corresponding to the sequence of NSP4 120–147, including NSP4 120–147 and the NSP4 protein. For the purpose of this invention, the term "comprising amino acids in a sequence corresponding to NSP4 112–175" shall mean a compound which has within it a sequence of amino acids corresponding to the sequence of NSP4 112–175, including NSP4 112–175 and the NSP4 protein. For the purpose of this invention, the term "compound comprising amino acids in a sequence corresponding to NSP4 112–150" shall mean a compound which has within it a sequence corresponding to the sequence of NSP4 112–150, including NSP4 112–150 and the NSP4 protein. For the purpose of this invention, the term "derivative" shall mean any molecules which are within the skill of the ordinary practitioner to make and use, which are made by derivatizing the subject compound, and which do not destroy the activity of the derivatized compound. Compounds which meet the foregoing criteria which diminish, but do not destroy, the activity of the derivatized compound are considered to be within the scope of the term "derivative." Thus, according to the invention, a derivative of a compound comprising amino acids in a sequence corresponding to the sequence of NSP4 114–135, NSP4 120–147, NSP4 112–175 or NSP4 112–150 need not comprise a sequence of amino acids that corresponds exactly to the sequence of NSP4 114–135, NSP4 120–147, NSP 112–175 or NSP4 112–175 so long as it retains a measurable amount of the activity of the NSP4 114–135, NSP4 120–147, NSP 112–175 or NSP4 112–150 peptide.

Another aspect of the present invention is a method of immunization against rotavirus infection or disease comprising administering to a subject a peptide NSP4 112–175 or NSP4 112–150 or a toxoid thereof. The immunization may result in homotypic or heterotypic immunity.

It is another embodiment of the present invention to provide a method of passive immunization against rotavirus infection comprising administering to an expectant mother NSP4 peptides or toxoids thereof, including, but not limited to NSP4 114–135, NSP4 120–174, NSP4 112–175 or NSP4 112–150.

It is also contemplated in the present invention that a non-glycosylated peptide of NSP4 may be administered to a subject or to an expectant mother. One skilled in the art is cognizant that NSP4 is a gylcosylated protein. The amino terminus of NSP4 contains two N-linked high mannose glycosylation sites, which are located in the first of three hydrophobic domains. Glycosylation of NSP4 is required for removal of the transient envelope from the budding particles. It is also contemplated that the glycosylation sites may be mutated using standard mutagenesis techniques well known and used in the art e.g., site-directed mutagenesis.

Inhibition of N-linked glycosylation will be preformed utilizing standard procedures that are well known in the art. Exemplary inhibitors of N-linked glycosylation that may used include, but are not limited to tunicamycin, deoxynojirimycin, castanospermine, deoxymannojirimycin or swainsonine.

It is another embodiment of the present invention to provide a method for the prevention of decreased growth rates caused by rotavirus infection including use of the NSP4 protein or peptides thereof, including but not limited to NSP4 114–135, NSP4 120–147, NSP4 112–175 and/or NSP4 112–150 as a treatment for or vaccine against rotavirus diarrhea. In addition, animals given peptide twice (at a two day interval) showed a rapid onset of severe diarrhea followed by stunted growth. The weight of these animals was 20–30% lower for three weeks after administration of peptide.

The present invention also illustrates that NSP4 114–135 promotes and augments cAMP-dependent Cl⁻ secretion in mouse intestinal mucosa and induces diarrhea in rodents in a time frame similar to STB (about 3 hrs). The electrophysiological data show that NSP4 induces calcium increases in the intestines of mice in an age-dependent manner and these increases in calcium result in chloride secretion as measured by short-circuit currents. Direct addition of cross-linked NSP4 114–135 to mouse ileal mucosal sheets resulted in a rise in current, similar to that evoked by the calcium agonist, carbachol. In addition to the age-dependence, induction of chloride secretion from intestinal mucosal sheets was site-dependent. Zero to minimal responses were observed when mouse jejunum, duodenum or colon tissue was employed, and maximum responses were induced when the ileum was utilized. These results support the model of NSP4-induced diarrhea.

The present invention also includes, NSP4 112–175, a cleavage product of the SA11 NSP4 C-terminus, which was detected in the extracellular medium of rotavirus-infected cells. The cleavage product mobilizes calcium and has enterotoxin activity in mice, similar to full-length NSP4 (Zhang et al., 2000). Thus, one skilled in the art realizes that these results demonstrate that NSP4 is released from virus-infected cells and such extracellular NSP4 initiates a signaling pathway leading to diarrhea (Ball et al., 1996). These distinctive pathogenic effects of NSP4 or NSP4 112–175 suggest that antagonists to NSP4 in vivo may result in protection against rotavirus-induced diarrhea.

These data show that NSP4 stimulation of a $Ca^{2+}$-dependent signal transduction pathway, resulting in disruption of normal intestinal epithelial transport, is similar to that reported for guanylin and the heat-stable enterotoxins. Based on the enteropathogenic similarities in intestinal secretion with those reported for guanylin and the heat-stable enterotoxins, NSP4 can be considered a viral enterotoxin.

It has been demonstrated that NSP4 induces diarrhea by activating an age-dependent, calcium-sensitive anion (chloride) permeability in the small and large intestine mucosa in both normal mice and mice with cystic fibrosis that lacks the cystic fibrosis transmembrane regulation. These properties of NSP4 indicate that it is a novel secretary agonist since other secretagogous fail to function in mice with cystic fibrosis. Further, this is confirmed in the present invention. Administration of NSP4, virus or peptide to 5–7 day old CFTR knock-out mice (mice homozygous for the mutation in the CFTR chloride channel coding region that causes Cystic Fibrosis) results in diarrhea in 100% of the cases.

One of skill in the art is cognizant that the models of NSP4-induced diarrhea may be altered. Thus, the scope of the present invention is not limited to one specific model of NSP4-induced diarrhea, but includes and is not limited to alterations and variations of the model. For example, the data from the Cystic Fibrosis mice suggest that age-dependence may be downstream of $Ca^{2+}$ moblization, thus a channel may be involved instead of a receptor for the regulation of age-dependent disease.

It is another embodiment of the present invention to provide methods for the screening for and identification of viral enterotoxins associated with rotavirus and other gastroenteritis viruses, such as caliciviruses, astroviruses, enteric adenoviruses, coronoviruses and parvoviruses, including in vitro administration of virus, viral proteins or peptides thereof to intestinal mucosa tissues or to cells and monitoring chloride secretion and/or intracellular calcium levels and/or cAMP levels.

It is another embodiment of the present invention to provide methods for the screening for and identification of viral enterotoxins associated with other viruses associated with diarrhea, including HIV and CMV, including in vitro administration of virus, viral proteins or peptides thereof to intestinal mucosa tissues or to cells and monitoring chloride secretion and/or intracellular calcium levels and/or cAMP levels.

Yet further, the present invention has also shown that administration of HIV gp160 to 6–7 day old Balb/C mice causes diarrhea in 100% of the cases.

It is another embodiment of the present invention to use the NSP4 protein or peptides thereof, including but not limited to NSP4 114–135, NSP4 120–147, NSP4 112–175 or NSP4 112–175 to identify and/or characterize a new intestinal receptor whose signaling induces secretion.

It is another embodiment of the present invention to provide a method for the intentional induction of intestinal secretion including administration of the NSP4 protein or peptides thereof, including but not limited to NSP4 114–135, NSP4 120–14, NSP4 112–175 or 112–150.

It is another embodiment of the present invention to provide a method for the treatment of cystic fibrosis including administration of NSP4 protein or peptides thereof, including but not limited to NSP4 114–135, NSP4 120–147, NSP4 112–175 or NSP4 112–150, to enhance fluid secretion.

It is another embodiment of the present invention to provide a method for the treatment of cystic fibrosis comprising administering NSP4 or derivatives or new molecules that act like NSP4 to enhance secretion through the same mechanism NSP4 uses.

It is another embodiment of the present invention to provide a new laxative including the NSP4 protein or peptides thereof, including but not limited to NSP4 114–135, NSP4 120–147, NSP4 112–175 or NSP4 112–150.

It is another embodiment of the present invention to provide methods for the identification and use of compounds, such as small molecule inhibitors, to bind the active domain of NSP4, NSP4 peptides or fragments thereof (i.e., NSP4 114–135, NSP4 120–174, NSP4 112–175 or NSP4 112–150) or other viral enterotoxins to prevent, ameliorate or stop diarrheal disease. For the purpose of this invention, small molecule inhibitors shall mean any ligand that can bind with high affinity to a target molecule, thereby inhibiting the target molecule's activity. Small molecule inhibitors include, but are not limited to, peptides, oligonucleotides, amino acids, derivatized amino acids, carbohydrates, and organic and inorganic chemicals. Libraries of small molecule inhibitors are available to the practitioner either according to known methods, or commercially. Accordingly, this method includes identifying a viral enterotoxin, screening the purified enterotoxin against one or more random small molecule libraries, for example, a random peptide library, a random oligonucleotide library, or a pharmaceutical drug library, and identifying those small molecules that bind with high affinity to the viral enterotoxin.

As used herein the term "candidate substance" refers to any molecule that may potentially inhibit or enhance NSP4 or any fragment of NSP4 (i.e., NSP4 114–135, NSP4 120–147, NSP4 112–175 or NSP4 112–150) activity. The candidate substance may be a protein or fragment thereof, a small molecule, or even a nucleic acid molecule. It may prove to be the case that the most useful pharmacological compounds will be compounds that are structurally related to NSP4 or any fragment of NSP4 (i.e., NSP4 114–135, NSP4 120–147, NSP4 112–175 or NSP4 112–150). Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from barks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide lbraries), is a rapid and efficient way to screen large numbers of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on NSP4 or any fragment of NSP4 (i.e., NSP4 114–135, NSP4 120–147, NSP4 112–175 or NSP4 112–150). Regardless of the type of inhibitor or activator identified by the present screening methods, the effect of the inhibition or activator by such a compound results in NSP4 or any fragment of NSP4 (i.e., NSP4 114–135, NSP4 120–147, NSP4 112–175 or NSP4 112–150) as compared to that observed in the absence of the added candidate substance.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determination of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

The present invention also contemplates the screening of compounds for their ability to modulate NSP4 or any fragment of NSP4 (i.e., NSP4 114–135, NSP4 120–147, NSP4 112–175 or NSP4 112–150) in cells. Various cell lines can be utilized for such screening assays, including cells specifically engineered for this purpose.

Depending on the assay, culture may be required. The cell is examined using any of a number of different physiologic assays. Alternatively, molecular analysis may be performed, for example, protein expression, mRNA expression (including differential display of whole cell or polyA RNA) and others.

In vivo assays involve the use of various animal models, including transgenic animals that have been engineered to have specific defects, or carry markers that can be used to measure the ability of a candidate substance to reach and affect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound or cell, or instead a broader indication such as behavior, anemia, immune response, etc.

Treatment of these animals with test compounds will involve the administration of the compound, in an appropriate form, to the animal. Administration will be by any route that could be utilized for clinical or non-clinical purposes, including but not limited to oral, intranasal, buccal, or even topical. Alternatively, administration may be by a parenteral route, e.g intradermal, subcutaneous, intramuscular, intraperitoneal or intravenous injection.

Determining the effectiveness of a compound in vivo may involve a variety of different criteria. Also, measuring toxicity and dose response can be performed in animals in a more meaningful fashion than in in vitro or in cyto assays.

Another method for identifying small molecule inhibitors includes the steps of identifying viral enterotoxins, determining the high resolution structure of these proteins and/or peptides thereof, determining the active domain(s) and designing small molecule inhibitors which bind with high affinity to the active domain(s). Another method includes identifying viral enterotoxins, identifying the intestinal receptor which binds the viral enterotoxin, and designing small molecule inhibitors which competitively bind the receptor, without inducing secretion.

It is another embodiment of the present invention to provide a method for the design of new drugs for the prevention of diarrhea and/or $Ca^{2+}$ mediated intestinal secretion including identifying the intracellular pathway by which $[Ca^{2+}]_i$, is increased or downstream between $Ca^{2+}$ mobilization and chloride channel activation or identifying channel blocking and making compounds which inhibit any step in the pathways. Specifically, this method includes identifying the molecules active in the signaling pathway and identifying compounds which inhibit their activity. Such compounds will include but not be limited to small molecule inhibitors which block binding of NSP4 to its receptor, blocking of G protein mediated or other signal transduction secondary messengers and pathways which lead to chloride secretion or diarrhea.

It is another embodiment of the present invention to provide a method for the diagnosis of rotavirus infection including the detection of NSP4 in stools of individuals with diarrhea. Detection of peptides of NSP4 is considered to fall within the scope of detection of NSP4.

It is another embodiment of the present invention to provide a method for the diagnosis of rotavirus infection including the detection of antibodies to NSP4 in the sera or stools of individuals with diarrhea.

It is another embodiment of the present invention to provide a vaccine comprising the NSP4 protein or peptides thereof, including but not limited to NSP4 114–135, NSP4 120–147, NSP4 112–175 or NSP4 112–150 to induce the formation of protective active or passive antibodies.

It is another embodiment of the present invention to provide a vaccine comprising a toxoid form of the NSP4 protein or fragments thereof, including but not limited to formaldehyde, heat inactivated or mutated NSP4 to induce the formation of a protective immune response. Fragments of NSP4 include, but are not limited to, NSP4 114–135, NSP4 120–147, NSP4 112–175 or NSP4 112–150.

It is another embodiment of the present invention to provide a method to monitor vaccine efficacy or protective immunity by determining the immune response to NSP4 protein and/or to peptides thereof.

It is another embodiment of the present invention to provide a method for immunization against rotavirus infection comprising administering to a subject a vaccine including the NSP4 protein or peptides thereof including, but not limiting to, NSP4 114–135, NSP4 120–147, NSP4 112–175 or NSP4 112–150 peptides.

It is another embodiment of the present invention to provide a method of passive immunization against rotavirus infection including administering to an expectant mother a vaccine including the NSP4 protein or peptides thereof, including but not limiting to, NSP4 114–135, NSP4 120–147, NSP4 112–175 or NSP4 112–150.

It is another embodiment of the present invention to provide a method for immunization against rotavirus infection comprising administering to a subject a vaccine comprising a toxoid form of the NSP4 protein.

It is another embodiment of the present invention to provide a method for immunization against rotavirus infection comprising administering to a subject a vaccine comprising a non-glycosylated NSP4 protein.

For an antigenic composition to be useful as a vaccine, an antigenic composition must induce an immune response to the antigen in a cell, tissue or animal (e.g., a human). As used herein, an "antigenic composition" may comprise an antigen (e.g., a NSP4 peptide or NSP4 polypepide or NSP4 protein or toxoid thereof), a nucleic acid encoding an antigen (e.g., an antigen expression vector), or a cell expressing or presenting an antigen. In particular embodiments the antigenic composition comprises the nucleic acid sequence that encodes NSP4, or any fragments thereof, including but not limiting to NSP4 112–135, NSP4 120–147, NSP4 112–175 or NSP4 112–150, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing a humoral and/or cell-mediated immune response in an animal. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence encoding a peptide or polypeptide comprising an antigen of the present invention in an in vitro translation system or in a living cell. Preferably the antigenic composition isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with the antibody recognition of the epitopic sequence.

A peptide or polypeptide corresponding to one or more antigenic determinants of the present invention should generally be at least five or six amino acid residues in length, and may contain up to about 10, about 15, about 20, about 25 about 30 ,about 35, about 40, about 45 or about 50 residues or so. A peptide sequence may be sythesized by methods known to those of ordinary skill in the art, such as, for example, peptide synthesis using automated peptide synthesis machines, such as those available from Applied Biosystems (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

In certain embodiments, an immune response may be promoted by transfecting or inoculating an animal with a nucleic acid encoding an antigen. One or more cells comprised within a target animal then expresses the sequences encoded by the nucleic acid after administration of the nucleic acid to the animal. Thus, the vaccine may comprise "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In other aspects, the nucleic acid comprises a coding region that encodes all or part of the NSP4, NSP4 114–135, NSP4 120–147, NSP4 112–175 or NSP4 112–150, or an immunologically functional equivalent thereof. Of course, the nucleic acid may comprise and/or encode additional sequences, including but not limited to those comprising one or more immunomodulators or adjuvants. The nucleotide and protein, polypeptide and peptide encoding sequences for various genes have been previously disclosed, and may be found at computerized databases known to those of ordinary skill in the art. One such database is the National Center for Biotechnology Information's Genbank and GenPept databases. The coding regions for these known genes may be amplified, combined with the sequences NSP4 (SEQ.ID.NO:16), NSP4 114–135, NSP4 120–147, NSP4 112–175 or NSP4 112–150 disclosed herein (e.g., ligated) and/or expressed using the techniques disclosed herein or by any technique that would be know to those of ordinary skill in the art (e.g., Sambrook et al., 1987). Though a nucleic acid may be expressed in an in vitro expression system, in preferred embodiments the nucleic acid comprises a vector for in vivo replication and/or expression.

Specifically, nucleic acids according to the present invention may encode an entire NSP4 gene, a domain of NSP4, or any other fragment of NSP4 as set forth herein. The nucleic acid may be derived from genomic DNA, i.e., cloned directly from the genome of a particular organism. The following sequences are sequences corresponding to NSP4 genes and are within the scope of the invention and are referenced with the corresponding GenBank Accession Numbers: ALA(SEQ.ID.NO:17, AF144792); C-11 (SEQ.ID.NO:18, AF144793); R-2 (SEQ.ID.NO:19, AF144794); BAP-2 (SEQ.ID.NO:20, AF144795); BAPwt (SEQ.ID.NO:21, AF144796);, A253 (SEQ.ID.NO:22, AF144797); A131 (SEQ.ID.NO:23, AF144798); A411 (SEQ.ID.NO:24, AF144799); A34 (SEQ.ID.NO:25, AF165219); H-2 (SEQ.ID.NO:26, AF144801); FI-23 (SEQ.ID.NO:27, AF144802); FI-14 (SEQ.ID.NO:28, AF144803); BRV033 (SEQ.ID.NO:29, AF144804); B223 (SEQ.ID.NO:30, AF144805); CU-1 (SEQ.ID.NO:31, AF144806); OSU (SEQ.ID.NO:32, D88831); and SA11 (SEQ.ID.NO:33, AF087678). Also included in the scope of the present invention is the nucleic acid sequences for other rotavirus genes including, but not limiting to: VP6 (SEQ.ID.NO:34, D00325); VP6(SEQ.ID.NO:35, K02086) and VP2(SEQ.ID.NO:36, X14949).

It is also contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

In particular embodiments, it is contemplated that nucleic acids encoding antigens of the present invention may be transfected into plants, particularly edible plants, and all or part of the plant material used to prepare a vaccine, such as for example, an oral vaccine. Such methods are described in U.S. Pat. Nos. 5,484,719, 5,612,487, 5,914,123, 5977,438 and 6,034,298, each incorporated herein by reference.

For example, it is contemplated that immunomodulators can be included in the vaccine to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFβ, LT and combinations thereof.

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

In certain embodiments, an antigenic composition's may be chemically coupled to a carrier or recombinantly expressed with a immunogenic carrier peptide or polypetide (e.g., a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to an immunogenic carrier protein are well known in the art and include, for example, glutaraldehyde, m-maleimidobenzoyl-N-hydroxysuccinimide ester, carbodiimide and bis-biazotized benzidine.

It may be desirable to co-administer biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m2) (Johnson/Mead, NJ), or a gene encoding a protein involved in one or more immune helper functions, such as B-7.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In certain embodiments, an adjuvant effect is achieved by use of an agent such as alum used in about 0.05 to about 0.1% solution in phosphate buffered saline. Alternatively, the antigen is made as an admixture with synthetic polymers of sugars (Carbopol®) used as an about 0.25% solution. Adjuvant effect may also be made by aggregation of the antigen in the vaccine by heat treatment with temperatures ranging between about 70° to about 101° C. for a 30-second to 2-minute period, respectively.

Some adjuvants, for example, are certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611).

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE® BCG (Organon Inc., West Orange, N.J.).

In a typical practice of the present invention, cells of Mycobacterium bovis-BCG are grown and harvested by methods known in the art. For example, they may be grown as a surface pellicle on a Sauton medium or in a fermentation vessel containing the dispersed culture in a Dubos medium (Dubos et al., 1947; Rosenthal 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2\times10^{10}$ cells/ml to about $2\times10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants also contemplated for use in the invention are the detoxified endotoxins, such as the refined detoxified endotoxin of U.S. Pat. No. 4,866,034. These refined detoxified endotoxins are effective in producing adjuvant responses in mammals. The combination of detoxified endotoxins with trehalose dimycolate is also contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. No. 4,436,727, 4,436,728 and 4,505,900. Combinations of just CWS and trehalose dimycolate, without detoxified endotoxins, is also envisioned to be useful, as described in U.S. Pat. No. 4,520,019.

One skilled in the art is cognizant that the NSP4 peptide (NSP4 114–135, NSP4 120–147, NSP4 112–175 or NSP4 112–150) or toxoid thereof may be produced synthetically or by an expression vector. Expression vectors that may be used include, but are not limited to mammalian, yeast, viral, bacterial, plant or insect.

Another embodiment of the present invention is a fusion protein. One of skill in the art is cognizant that fusion proteins are generated using standard molecular biology techniques well known in the art. Further, one of skill in the art is aware that in the present invention the term "linked" can be used interchangeably with the term "fused". The fusion protein comprises a NSP4 peptide linked to a protein that forms a virus-like particle. The NSP4 peptide may include, but is not limited to, NSP4 114–135, NSP4 120–147, NSP4 112–175 or NSP4 112–150. The virus-like particle is a viral protein or peptide isolated from Caliciviridae or Reoviridae. Specifically, the viral protein or peptide isolated from Caliciviridae is a Norwalk virus protein or peptide and the viral protein or peptide isolated from Reoviridae is a rotavirus protein or peptide. The Norwalk virus protein or peptide may be ORF2 or ORF3 or ORF2 plus ORF3 or a toxiod thereof. The rotavirus protein or peptide may be VP2, VP4, VP5, VP6 and VP7. In specific embodiments, the rotavirus peptide is VP2.

It is well known that virus-like particles (VLPS) consist of capsid proteins assembled into a shell-like structure without the presence of viral nucleic acid within the shell. These shells can display conformational epitopes that are not present on individual capsid proteins. The use of VLPs offer several immunogenic advantages. First, VLPs present conformational epitopes to the immune system in such a way as native infectious particles so that neutralizing antibodies and other protective immune responses are induced effectively. Second, because VLPs are noninfectious, inactivation is not required. Thus, one skilled in the art realizes that the use of virus-like particles may be better immunogens than formalin-inactivated whole-virus vaccines or proteins. Thus, it can be appreciated that the fusion protein of the present invention may be a better immuogen than the NSP4 alone.

Another embodiment of the present invention comprises an expression vector comprising a nucleic acid sequence encoding a fusion protein, wherein the fusion protein comprises a NSP4 peptide and a viral peptide that forms a virus-like particle. The nucleic acid sequence is operatively linked to a promoter sequence.

As used herein the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called ihe Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

It is another embodiment of the present invention to provide vaccines against gastroenteritis viruses, including rotaviruses, caliciviruses, astroviruses, enteric adenoviruses, coronaviruses and parvoviruses, including viral enterotoxins which induce the diarrhea associated with viral infection.

It is another embodiment of the present invention to provide methods for the identification of potential vaccines against gastroenteritis viruses, including screening for viral enterotoxins, raising antibodies against any identified possible enterotoxins, and determining whether the antibodies protect against disease caused by the virus.

It is another embodiment of the present invention to provide a method of identifying a virulent strain of rotavirus by determining the amino acid sequence of the NSP4 protein of the strain.

It is another embodiment of the present invention to identify key residues in NSP4 responsible for its ability to induce diarrhea and thus to identify specific amino acid sequences associated with avirulence. Having done this, gene 10 from these avirulent viruses may be used to select and produce reassortment viruses that contain a gene 10 that confers an avirulent phenotype which can be used as live attenuated reassortment virus vaccine candidates.

It is another embodiment of the present invention to provide methods for the screening of antiviral compounds, compositions and/or treatments and/or the evaluation of vaccine efficacy, including administering viruses, viral proteins or peptides thereof to one or more of three new animal models for diarrheal virus infections, the CD1 mouse, the Balb/C mouse and the Sprague-Dawley rat.

Pharmaceutical Compositions and Administration

Aqueous compositions of the present invention comprise an effective amount of NSP4 (NSP4 114–135, NSP4 120–147, NSP4 112–175 or NSP4 112–150) protein, polypeptide, peptide, expression vector, or cells containing the expression vector, antibodies, epitopic core region, inhibitor, and/or such like, dissolved and/or dispersed in a pharmaceutically acceptable carrier and/or aqueous medium. Aqueous compositions of gene therapy vectors expressing any of the foregoing are also contemplated.

The phrases "pharmaceutically and/or pharmacologically acceptable" refer to molecular entities and/or compositions that do not produce an adverse, allergic and/or other untoward reaction when administered to an animal as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of the agent as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

The active compounds of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure (see for example, "Remington's Pharmaceutical Sciences" 15th Edition). Some variation in dosage will necessarily occur depending on the condition of the subject being treated. The person responsible for administration will, in any event, determine the appropriate dose for the individual subject.

The active peptides and/or agents may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One skilled in the art recognizes that nasal solutions and/or sprays, aerosols and/or inhalants can be used in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

NSP4

NSP4 was purified from recombinant-baculovirus pAC461-G10 infected Spodoptera frugiperda (Sf9) cells expressing gene 10 by FPLC on a QMA anion exchange column as previously described (Tian et al., 1994 and Tian et al., 1995), and with an additional affinity purification step on a column containing anti-NSP4 antibodies. Different NSP4 preparations of >70% and 90% purity gave the same biologic results. The protein was sterile based on bacteriologic culturing in L-broth incubated at 37 C for one week, which predict surface potential (Parker et al., 1986), turn potential (Pt) (Chou 1978), and amphipathic structure (Margolit et al., 1987). A block length of 11 was used and an amphipathic score (AS) of 4 was considered significant. Sequences were selected based on the high predicted propensities for folding into amphipathic helices and reverse turns, because small peptides which typically lack any folding pattern in an aqueous environment can fold into an ordered secondary structure resembling the nascent protein if the structural propensity is high (Dyson et al., 1988; Dyson et al., 1991; Dyson et al., 1988; Dyson et al., 1995; Yao et al., 1994; Waltho et al., 1993; Dyson et al., 1992; Wright et al., 1988).

Peptide sequences used in this study include: NSP4 114–135 (Both et al., 1983), (DKLTTREIEQVELLKRIYDKLT, SEQ.ID.NO:1), AS=35; a peptide from the amino-terminus of NSP4, NSP4 2–22 (EKLTDLNYTLSVITLMNNTLH, SEQ.ID.NO:2), AS=14; an extended highly amphipathic peptide, NSP4 90–123 (TKDEIEKQMDRVVKEMRRQLEMIDKLTTREIEQ, SEQ.ID.NO:3) AS=71; a mutated NSP4 114–135 peptide, mNSP4 131K (DKLTTREIEQVELLKRIKD KLT, SEQ.ID.NO:4) AS=31; and a peptide from the COOH-terminus of the Norwalk virus capsid protein having a centrally located tyrosine residue (Jiang et al., 1990), NV 464–483 (DTGRNLGEFKAYPDGFLTCV, SEQ.ID.NO:5) AS=41 (Table 1), and NSP4 120–147 (EIEQVELLKRIYDKLTVQTTGEIDMTKE, SEQ.ID.NO:6) AS=35.0, NSP4 112–175 (MIDKLTTREI EQVELL KRIYDKLTVQTTGEIDMTKEINQKN-VRTLEEWESGKN PYEPKEVTAAM, SEQ.ID.NO:9) and NSP4 112–150 (MIDKLTTREIEQVELLKRIYDK LTVQTTGEID MTKEINQ, SEQ.ID.NO:10).

TABLE 1

| Peptide | Sequence[1] | AS[2] | Pt[3] | Mr[4] |
|---|---|---|---|---|
| NSP4 114-135 | DKLTTREIEQVELLKRIYDKLT | 35 | 1.12 (YDKL) | 2705 |
| NSP4 2-22 | EKLTDLNYTLSVITLMNNTLH | 13.9 | 1.12 (TDLN) | 2434 |
| NSP4 90-123 | TKDEIEKQMDRVVKEMRRQLEMIDKLTTREIEQ | 70.6 | 1.11 (TKDE) | 4092 |
| NSP4 m131K | DKLTTREIEQVELLKRI(K)DKLT | 31.4 | 1.08 (KDKL) | 2669 |
| NV 464-483 | DTGRNLGEFKAYPDGFLTCV | 41.4 | 1.58 (YPDG) | 2204 |

[1]NSP4 sequence from rotavirus SA11 (Both et al., 1983). Norwalk virus (NV) sequence from Jiang et al., 1990. Underlined sequence is the region of the NSP4 2-22 peptide which overlaps with the NSP4 114-135 peptide. This substitution decreases the trun potential from 1.12 to 1.08. The mutated tyrosine to lysine residue is shown in bold and in parentheses.
[2]AS = amphipathic score. A block length of 11 was used with an AS of 4 considered significant (Margolit et al., 1987).
[3]PT = turn potentials greater than 1.0 within the selected peptide based on the algorithm of Chou and Fasman (1974, 1978).
[4]Mr = Theoretical mass.

and lacked endotoxin based on testing by the limulus amebocyte lysate (LAL) assay (Levin 1968 and Novitsky 1984). VP6 was purified to >95% purity from recombinant-baculovirus pAc461/SA11-G6 infected Sf9 cells by gradient centrifugation as previously described (Zeng et al., 1996). Both proteins were lyophilized and diluted in sterile PBS to a final volume of 50 µl per dose, regardless of the route of administration.

Example 2
Synthetic Peptides

Synthetic NSP4-specific and control peptides utilized in this study were originally selected based on algorithms All peptides were synthesized by the University of Pittsburgh Peptide Core Facility employing Fmoc chemical strategy and standard protocols (Carpino 1970). Coupling and deblocking efficiencies were monitored by the ninhydrin colorometric reaction (Kaiser, et al., 1970). Peptides were cleaved from their solid resin support and separated from organic contaminants by multiple cold ether extractions, and conventional gel filtration chromatography (Sephadex G-25). The final peptide product was characterized by reverse-phase HPLC (Deltapak C4, Waters) and plasma desorption mass spectroscopy (Johnson et al., 1986). Only those peptides with the correct theoretical mass and 90% or greater full-length product were employed in these studies. Prior to use, peptides were further purified either by HPLC on a semi-preparative, reverse-phase C18 column (uBondapak, Waters) or by multiple elutions from a conventional gel filtration column (1.5 mm×40 mm). Peptide purity was confirmed prior to inoculations by gel filtration chromatography (Protein-Pak 60 column, 10 μm, Waters) on a Waters HPLC unit. The elution profiles were monitored by UV absorption (Lambda-Max LC-spectrophotometer, Waters) at 220 nm and recorded by a 745 Data Module (Waters). The elution buffer was PBS, pH 7.2, and the flow rate 0.5 ml/min. Sterility was confirmed as described for NSP4 protein.

Example 3

Glutaraldehyde Cross-linking of Synthetic Peptides

Peptides were cross-linked to themselves or to the carrier protein, keyhole limpet hemocyanin (KLH), by glutaraldehyde in a single-step coupling protocol (Reichlin 1980). Briefly, the peptide immunogen was coupled to KLH at a ratio of 100 nmol peptide: 1 nmol KLH or to itself at a 1:1 ratio by the addition of glutaraldehyde to a final concentration of 0.4%. The reaction was quenched by the addition of 1M glycine (Cf=20 mM). The cross-linked peptides were extensively dialyzed against sterile PBS prior to use.

Example 4

Antibody Production

NSP4 114–135 peptide-specific antiserum was generated in CD1 mice and New Zealand white rabbits by immunization with peptide cross-linked via glutaraldehyde to the protein carrier KLH, as described above. The first inoculum was emulsified in Freund's complete adjuvant, whereas all subsequent inoculations were prepared in incomplete Freund's adjuvant. Rabbits were injected intramuscularly (IM, once in each hip) and subcutaneously (SC) across the back of the neck. Boosting doses of emulsified antigen (100 nmol of peptide) were done every 4 wk for a total of 5 immunizations. Mice were immunized every three weeks by the IM, SC and IP routes. Preimmunization and postimmunization sera were evaluated by peptide ELISAs (titer of 400–3200) as previously described (Ball et al., 1994) and by Western blot analyses.

Example 5

IP and IL Administration of Protein and Peptides

Purified NSP4 protein, peptide alone, or cross-linked to itself, were administered to young (6–10 days) and older (11–25 days) outbred CD1 or inbred Balb/C mice, and outbred Sprague-Dawley rats by the intraperitoneal (IP), intraileal (IL), intramuscular (IM), subcutaneous and oral routes. The peptide or protein inocula were diluted in sterile PBS to a final volume of 50 μl per dose, regardless of the route of administration or inoculum. A 30 G needle was employed for the IP and IL delivery of the inocula. Peptide was delivered orally to young mice by gavage using a PE-10 polyethylene flexible tubing (Intramedic, Becton Dickinson) and food coloring. For the surgical introduction of the peptide or protein via the IL route, animals were anesthetized with isofurane (Anaquest), a small incision was made below the stomach, the inocula were directly injected into the upper ileum, and the incision was sealed with polypropylene sutures (PROLENE 6-0, Ethicon). The pups were isolated, kept warm, and closely monitored for a minimum of 2 hrs prior to returning them to their cage.

Example 6

Monitoring of Diarrhea Induction

Diarrhea induction by the NSP4 protein and peptides was carefully monitored for 24 hrs following the inoculations. Each pup was examined every 1–2 hr for the first 8 hr and at 24 hr post inoculation by gently pressing on the abdomen. Diarrhea was noted and scored from 1 to 4 with a score of 1 reflecting unusually soft, loose, yellow stool, and a score of 4 being completely liquid stool. A score of 2 (mucous with liquid stool, some loose but solid stool) and above was considered diarrhea. A score of 1 was noted, but was not considered as diarrhea. The scoring was done by a single person and the pups were coded during analysis of diarrhea. Other symptoms monitored included lethargy, coldness to the touch, and ruffled coats in older animals.

Example 7

Analysis of Chloride Secretion Responsiveness to NSP4 114–135 in the Intestinal Mucosa of Mice Unstripped intestinal mucosal sheets from 19–22 and 35 day old mice were analyzed for chloride secretory responsiveness to NSP4 114–135. Short-circuit currents (Isc) were measured across unstripped intestinal mucosal sheets from 19–22 and 35 day old CD1 mice using an automatic voltage clamp (Bioengineering, Univ. of Iowa) as described previously (Sears et al., 1995 and Morris et al., 1994). The mid-ileum of the mouse intestines was utilized. The unstripped mucosal sheets taken from the intestine were placed into modified Ussing chambers with 0.12 cm$^2$ apertures (machine shop, UTHSC) and transepithelial potential (Vt) was registered by 3 M KCl agar bridges connected to balanced calomel half-cells. The transepithelial current required to clamp Vt to 0 was passed through Ag-AgCl electrodes connected to the 3 M KCl bridges. All experiments were performed at 37 C in bicarbonate Ringers solution gassed with 95% O2–5% $CO_2$ by airlift circulators as previously described (same as above). The mucosal bath contained sodium-free (N-methyl-D-glutamine) substituted Ringers to minimize the effects on Isc of cAMP stimulated electrogenic $Na^{+/}$ glucose co-transport across the small bowel (Grubb 1995). Following temperature and ionic equilibration, basal Isc measurements were taken and intestinal mucosal sheets were challenged with cross-linked peptide (either NSP4 114–135, NSP4 2–22, or mNSP4 131K), the calcium-elevating agonist carbachol (Cch), or the cAMP-agonist forskolin (FSK). Bumetamide sensitivity was tested and confirmed the chloride secretory response.

Example 8

NSP4 Protein Induces Age-dependent Diarrhea in Mice

Whether administration was IP or intraileal (IL), diarrhea was observed within 1 to 4 hr post inoculation, typically continued for up to 8 hr, but occasionally persisted for 24 hr. Purified NSP4 (0.1–5 nmol) was administered by the IP route to 6–7 and 8–9 day old CD1 pups. In 6–7 day old CD1 pups, IP administration of 0.1 nmol of NSP4 induced diarrhea in 60% of the mice, whereas no disease was induced in 8–9 day old mice with the same concentration of protein (FIG. 1). IP administration of 1 nmol of NSP4 resulted in 100% of the 6–7 day pups with diarrhea, and 60% of the 8–9 day old mice with disease. A larger dose of 5 nmol of NSP4 induced diarrhea in 90% of the older (8–9 day) mice. Additional clinical symptoms included lethargy and coldness to the touch, which were observed in the majority of treated animals with diarrhea of all ages. The induction of diarrhea by NSP4 was shown to be specific for this protein as administration of the same volume of buffer or VP6 had no effect.

IL administration of 0.5 nmol of purified NSP4 protein resulted in disease in 100% of the CD1 pups (8–9 day old mice) within the first 2 hr post inoculation, whereas no diarrhea was observed in 17–18 day old pups (Table 2, FIG. 1).

tered since the volume of each dose was limited to 50 µl. These data indicate the disease response in CD1 mice can be divided into three groups based on the dose of the NSP4 114–135 peptide, 1) less than and equal to 50 nmol (1 mM) resulting in 30–40% of the animals with disease, 2) 100–400 nmol (2–8 mM) yielding disease in 60–70% of the animals, and 3) 500 nmol (10 mM) above inducing diarrhea in at least 89% of the young mice.

Diarrhea was induced in 100% of the 6–7 day old Balb/C pups with lower concentrations (only 50 nmol) of peptide (FIG. 4), and diarrhea was observed in 80% of the Balb/C mice given 0.1 nmol (2 µM) of NSP4 114–135. Hence the Balb/C pups appeared more sensitive to the effects of NSP4 114–135.

TABLE 2

Intraileal administration of NSP4 and NSP4 114-135.

| Species | Age (days) | Inoculum | Concentration (nmol) | Diarrhea |
|---|---|---|---|---|
| Sprague Dawley rat | 6–7 | X-linked NSP4 114-135 | 120–240 | 9/10 |
| Balb/C mice | 8–9 | X-linked NSP4 114-135 | 10 | 6/6 |
| Balb/C mice | 11–12 | X-linked NSP4 114-135 | 10 | 2/6 |
| Balb/C mice | 15–17 | X-linked NSP4 114-135 | 10 | 0/6 |
| CD1 mice | 7 | X-linked NSP4 114-135 | 50 | 3/5 |
| CD1 mice | 11–12 | X-linked NSP4 114-135 | 50 | 2/8 |
| CD1 mice | 17–18 | X-linked NSP4 114-135 | 50 | 0/6 |
| CD1 mice | 25 | X-linked NSP4 114-135 | 50 | 0/5 |
| CD1 mice | 25 | X-linked NSP4 114-135 | 100—200 | 0/8 |
| CD1 mice | 8–9 | NSP4 | 0.5 | 5/5 |

Thus, the response to NSP4 was age- and dose-dependent in CD1 pups. In addition, the induction of diarrhea by NSP4 was specific, as administration of the same concentration of purified rotavirus VP6 or the same volume of buffer had no effect (FIG. 1). The effect of IP and IL delivery of NSP4 protein in mice is the same. Intramuscular (IM) inoculation of 1 nmol of purified NSP4 produced no ill effects. Subcutaneous and oral administration of NSP4 also produced no ill effects.

Figure 2:
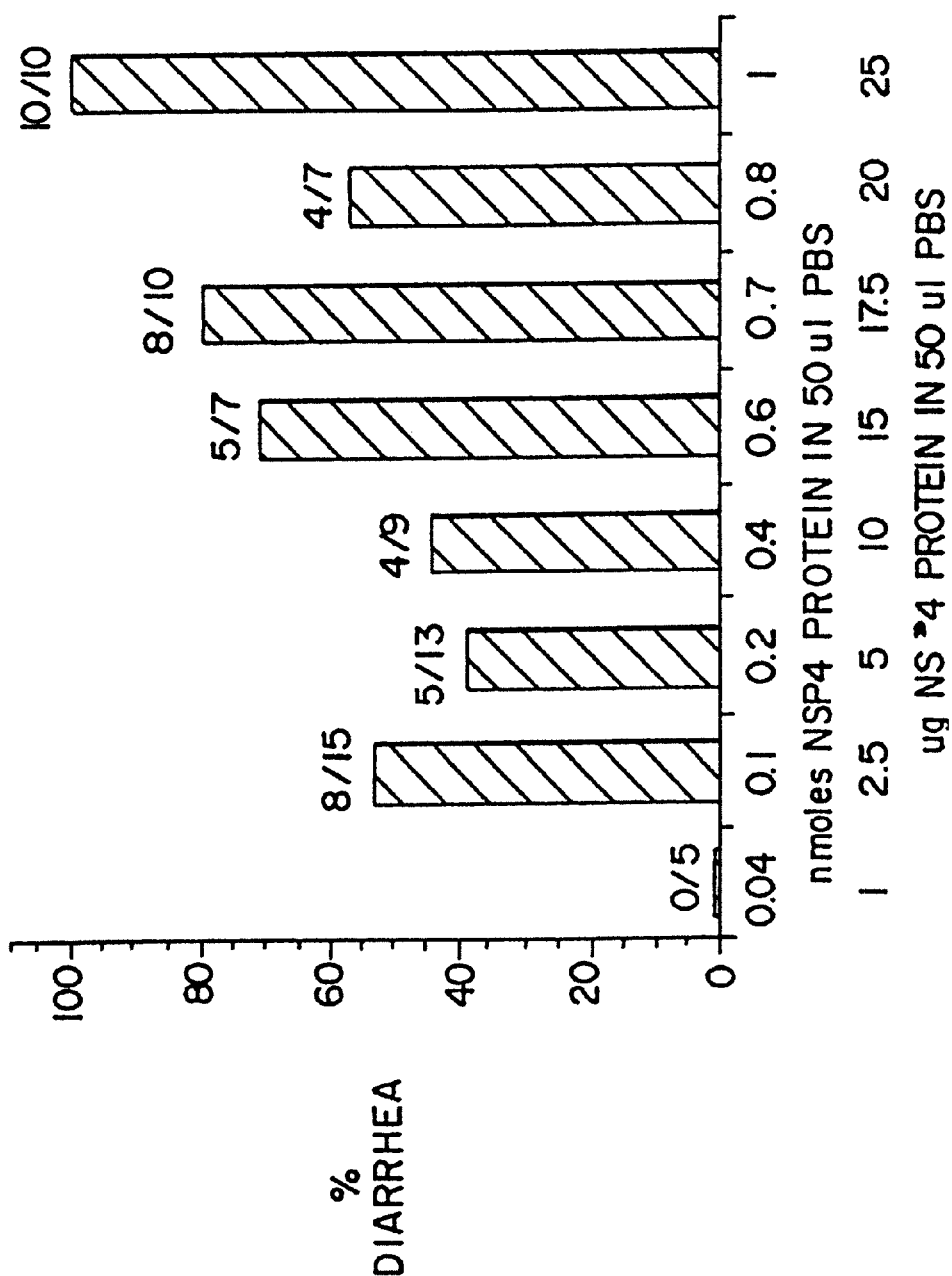

Additional data showing a dose response in 6–7 day old CD1 pups is presented in FIG. 2. The amount of peptide administered is shown in nanomoles and micrograms. 0.04–1.0 nmols (1–25 µg) of purified NSP4 was administered to 6–7 day old CD-1 pups by the IP route. A correlation between increasing incidence of diarrhea and increasing dose was seen (FIG. 2) over the range tested. The highest tested dose (1.0 nmol=25 µg) induced diarrhea in all mice tested (10 of 10).

Example 9

NSP4 114–135 Peptide Induces Diarrhea in Mice

The NSP4 114–135 peptide has an AS of 35, is localized in the cytoplasmic domain of NSP4, and mobilizes intracellular calcium in eukaryotic cells (Tian et al., 1994 and Tian et al., 1995).

Figure 3:
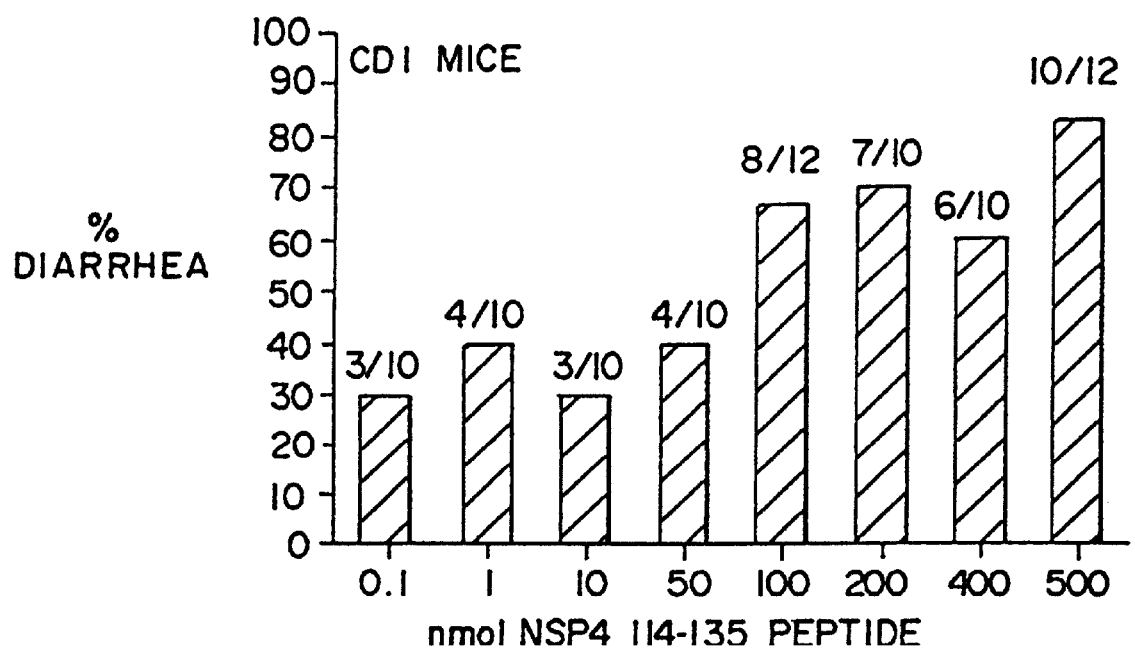

Following IP administration of 0.1 to 50 nmol of the NSP4 114–135 peptide, a similar disease response was noted in 6–7 day old CD1 outbred pups with 30–40% diarrhea induction (FIG. 3). The percentage of CD1 pups with diarrhea increased to 60–70% following the IP delivery of 100–400 nmol of NSP4 114–135 and 89% of pups had diarrhea following administration of a dose of 500 nmol of peptide. Induction of disease in 100% of the CD1 pups was not achieved; doses exceeding 500 nmol were not adminis- Doses exceeding 50 nmol (1 mM) of NSP4 114–135 peptide were sufficient to induce diarrhea in the majority of young mice when administered by the IP route. The diarrhea was observed within 1 to 4 hr post inoculation and typically continued for up to 8 hr, but occasionally was present for 24 hr. The severity of diarrhea typically increased with time. That is, a mouse with a diarrhea score of 1 in the first hr post inoculation would have a diarrhea score of 4 in the next hr. Various degrees of lethargy were noted following the administration of peptide and this was most pronounced at 3 to 4 hr post inoculation. The lethargy was accompanied by the pups being cold to the touch and was age-dependent. The severity of the induced diarrhea was greater in the Balb/C pups. No symptoms were noted with control peptides (NSP4 2–22, NV C-terminus) or PBS administered to the same age and species of mice.

Example 10

NSP4 120–147 Peptide Induces Diarrhea in Mice

A peptide corresponding to amino acid residues 120–147 of NSP4 was prepared and tested in 5–7 day old pups. When a dose of 100 nmols was administered, all (5 of 5) animals exhibited severe diarrhea. A dose of 5 nmols induced diarrhea in 7 out of 8 animals (88%). This demonstrates that other peptides derived from NSP4 can be prepared and screened to find the peptide with the highest activity. It is well within the ability of one of ordinary skill in the art to synthesize and screen a library of overlapping peptides that represents the entire sequence of the NSP4 protein in order to locate peptides with biological activity. One skilled in the art can readily appreciate that both the length of the peptides, and the number of residues that overlap in adjacent peptides, can be varied at the discretion of the practitioner without deviating from the spirit of the present invention.

Example 11

Diarrhea Induction in CD1 and Balb/C Mice by Cross-linked NSP4 114–135

Figure 5:
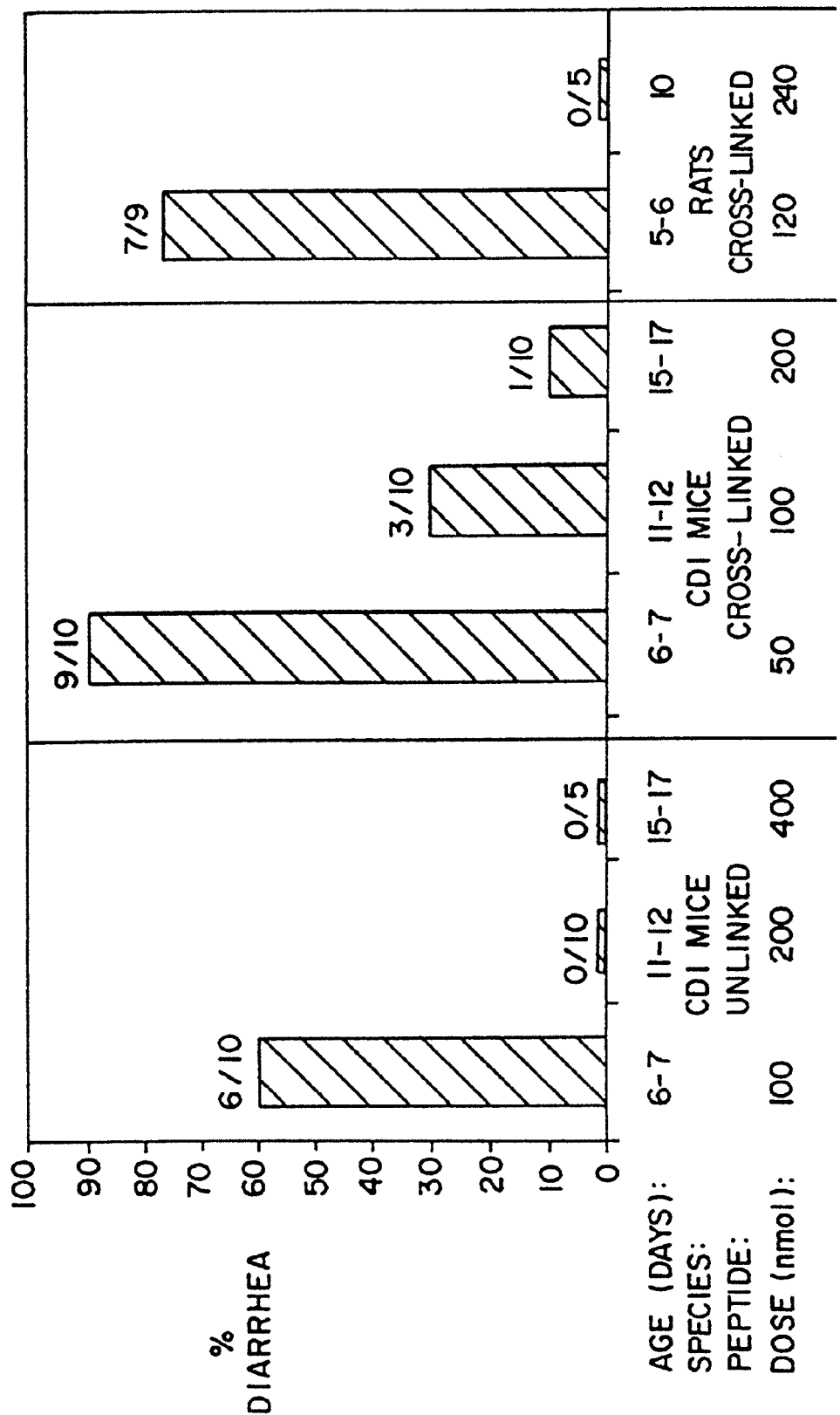
Figure 6:
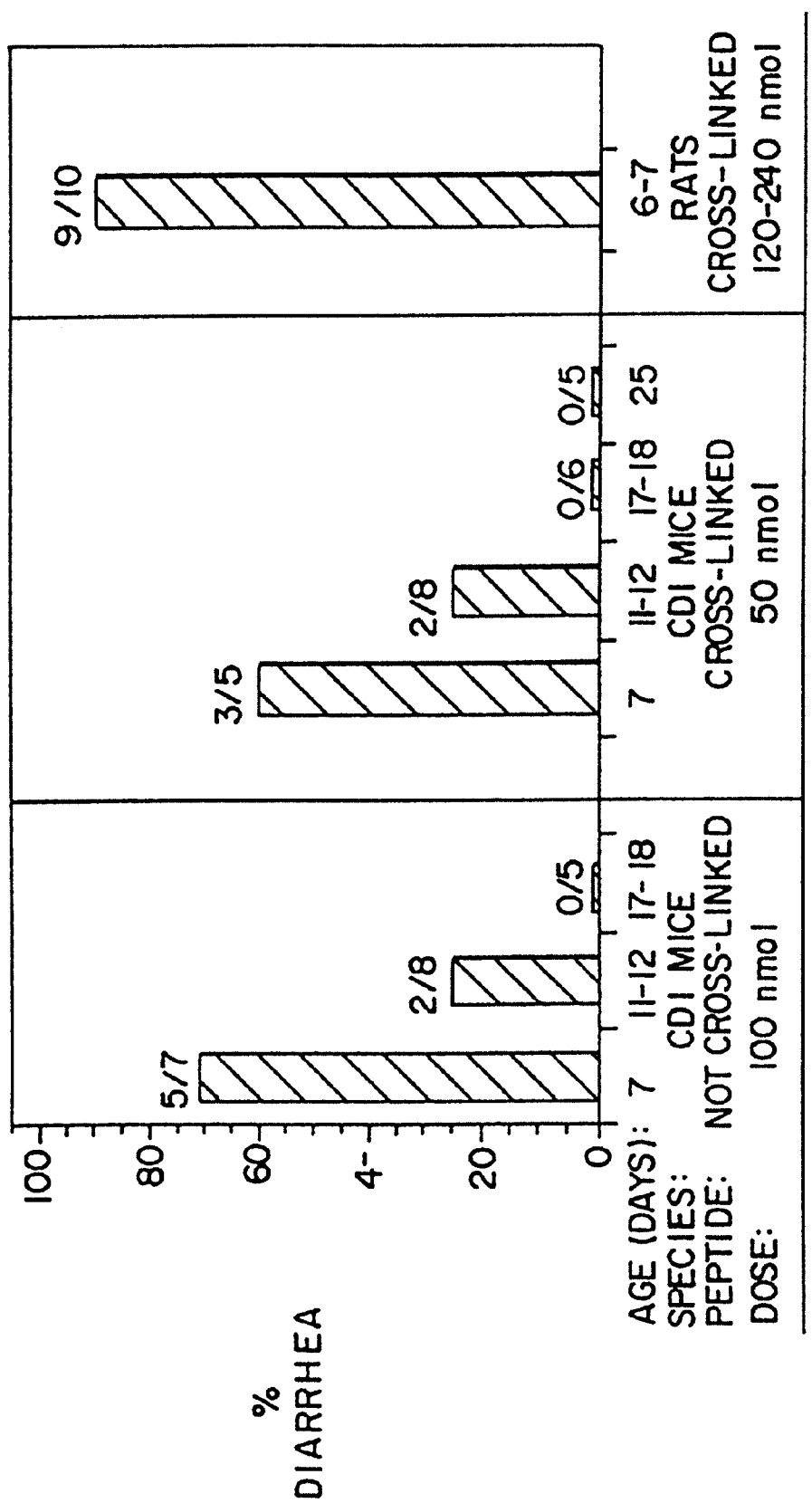

The NSP4 114–135 peptide was cross-linked to itself by glutaraldehyde and administered to young mouse pups by the IP route to determine if the diarrhea induction was affected by structure or oligomerization. Diarrhea was induced in the majority of the CD1 pups at a lower dose of NSP4 114–135 when the peptide was cross-linked to itself when compared to the peptide alone (FIG. 7A and FIG. 7B). One nmol of cross-linked peptide induced diarrhea in 80% of the CD1 pups which increased to 90% with 250 nmol of cross-linked NSP4 114–135. As illustrated in FIG. 5 and FIG. 6, doses at or above 1 nmol (20 µM) of cross-linked peptide were sufficient to elicit a response in the majority of the CD1 pups. Increasing the dose above 1 nmol of cross-linked NSP4 114–135 had little effect, indicating the diarrheal response could not be increased with increased amounts of synthetic peptide, or that the response, once stimulated, could be saturated or additional stimulation had no effect.

Similar to the response in CD1 mice, diarrhea induction in 100% of the Balb/C pups was achieved with a lower dose (10 nmol, 200 µM) of cross-linked peptide when compared to the peptide alone (FIG. 7A and FIG. 7B). In addition, the lethargy and coldness to the touch were more severe and lasted longer in animals that received the cross-linked peptide. Cross-linked NSP4 2–22 and NV C-terminus peptides were administered as controls and did not induce symptoms in young mice.

Induction of disease at a lower dose and with greater severity with the IP administration of cross-linked NSP4 114–135 suggests that cross-linking either stabilizes the peptide, oligomerizes the peptide, or results in a conformation more closely resembling the native protein. These data suggest structure may be important for disease induction.

Example 12

Cross-linked NSP4 114–135 Peptide Also Induces Diarrhea in Young Rats

The NSP4 114–135 peptide was tested in a second species, the Sprague-Dawley rat to determine whether the disease response induced by this peptide was only effective in young mice. IP inoculation of 100–250 nmol of cross-linked peptide induced diarrhea in 78% of young (6 days) rat pups and in none of the older (10 day) rat pups (FIG. 5). No disease was observed in the same age rodents administered control peptides. The response in rats was slower than that observed in mice, taking from 6 to 12 hr before the onset of diarrhea was noted, compared to 2 to 4 hours post inoculation for the mice, and required a higher concentration of peptide to observe disease. However, the induced diarrhea and lethargy in the young rats frequently persisted for up to 48 hr. These differences may reflect the difference in size and intestinal transit time between the rat and mouse or species (genetic) variation.

Example 13

IL Delivery of NSP4 Peptide

IL administration of 120–240 nmol of cross-linked NSP4 114–135 induced diarrhea in 90% of young (6–7 days) rat pups. Analogous to the response of young rats following the IP administration of cross-linked peptide, the onset of diarrhea was slower than that seen in the mice, taking from 6 to 12 hr, but lasted for a greater length of time (up to 48 hr). The surgical introduction of 10 nmol (200 µM) of cross-linked peptide induced diarrhea in 100% of the young (8–9 days) Balb/C pups, identical to the induction of diarrhea following IP delivery (Table 2). The age-dependence of the diarrhea response noted with the IP administration of cross-linked NSP4 114–135 was maintained with the IL administration of cross-linked peptide. Only one-third of the 11–12 day old Balb/C mice had diarrhea when administered 10 nmol of cross-linked peptide by the IL route, and none of the 15–17 day animals had diarrhea. In addition, older CD1 mice (11–12 and 25 days) had no ill effects from the IL delivery of 50–200 nmol (1–4 mM) of cross-linked peptide (FIG. 6, Table 2). An equal concentration of cross-linked NSP4 2–22 peptide or an equal volume of PBS, when surgically introduced in both young and older rodents, had no ill effects (data not shown).

Hence, the effect of IP and IL delivery of NSP4 peptide in rodents was equivalent.

Example 14

Diarrhea Induction is age Dependent

Between 100 and 300 nmol of NSP4 114–135 peptide, alone or cross-linked, was administered by the IP route to different age outbred mice and rats. Diarrhea was observed in the young mice within 2 to 4 hr post inoculation, whereas reduced or no symptoms were seen in older (11–12 or 15–17 days) animals (FIG. 5 and FIG. 6). With IP administration of peptide alone, disease was induced in 60% of the 6–7 day old CD1 pups with no symptoms noted in the 11–12 and 15–17 day old mice. IP administration of cross-linked peptide resulted in 90% diarrhea induction in 6–7 day old CD1 pups, 30% disease in 11–12 day old pups, and only 10% disease in 15–17 day old mice.

A comparable age dependence was observed with the Sprague-Dawley rats when cross-linked peptide was administered by the IP route. Diarrhea was detected 6 to 12 hr post inoculation in 78% of the young (5–6 day) rats while no disease was seen in the 10 day old rats given a similar dose of cross-linked peptide (FIG. 5 and FIG. 6). Thus an age dependence, similar to what is seen in a natural infection, is seen with the NSP4 114–135 peptide.

Example 15

Induction of Diarrhea is Dose Dependent

Figure 4:
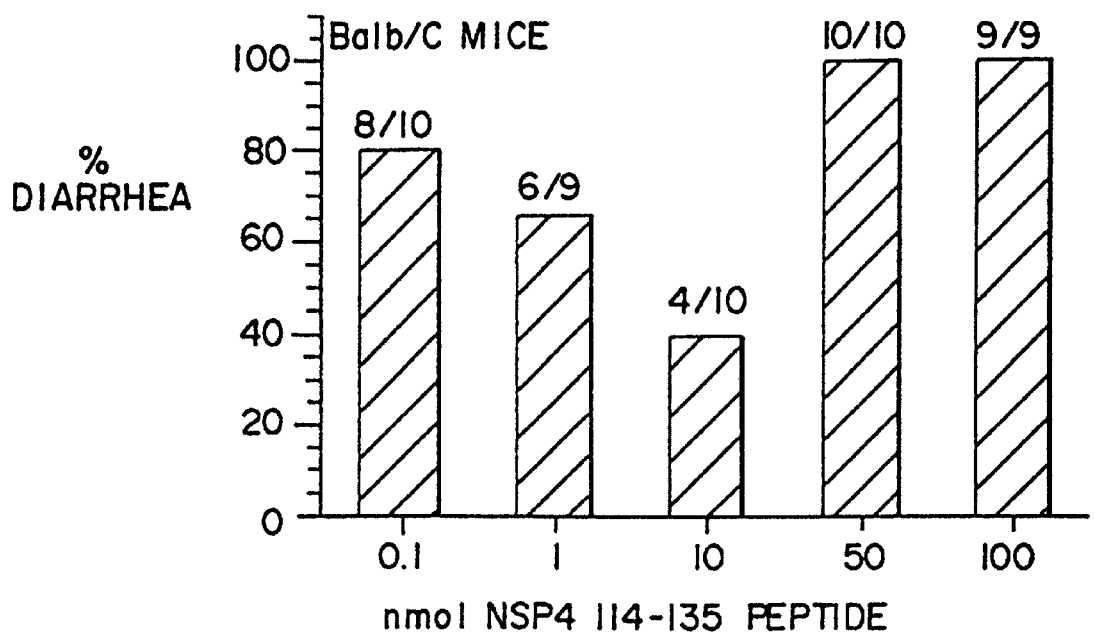

Doses of 0.1–500 nmol of a peptide were administered IP to 84 CD1 pups (6–7 days old; FIG. 3 and FIG. 4). The disease resp onse to the NSP4 114–135 peptide was dose-dependent ($X^2_{trend}=9.98$, p=0.0016) with a DD50 (50% diarrheal dose) of 79 nmol (Collins et al., 1988).

Example 16

Specificity of the Diarrhea Response to Peptide NSP4 114–135

Specificity of the diarrhea induction by the NSP4 114–135 peptide was confirmed by the administration of a panel of control peptides to young mouse pups (Table 1 and Table 3).

Mutant peptide mNSP4 131K, in which the tyrosine at position 131 of NSP4 114–135 is replace with a lysine did not induce diarrhea (0/11), indicating the importance of this tyrosine residue in the induction of diarrhea. Neither did NSP4 2–22 or NV 464–483 cause diarrhea, 0/11 and 0/10, respectively. NSP4 90–123, which overlaps the 114–135 peptide by 9 residues, induced diarrhea in only 20% (2/10) of the mice tested (Table 3). The percentage of diarrhea induction increased to 50% when the NSP4 90–123 peptide was crosslinked. Cross-linked mutant (m)NSP4 131k peptide induced diarrhea in 2 of 10 mice, while cross-linked NV 464–483 did not cause disease. Thus, the response to peptide alone appears to be directed to a region of NSP4 inclusive of residues 114–135.

TABLE 3

Specificity of the Diarrheal Response:
Diarrhea Induction in CD1 Mice following IP Administration of 50–100 nmol Peptide

| Peptide | % Diarrhea | # responders/total # tested |
|---|---|---|
| NSP4 114-135 | 67 | 8/12 |
| antibody[a] + NSP4 114-135 | 10 | 1/10 |
| Cross-linked NSP4 114-135 | 75 | 15/20 |
| MNSP4 131K[b] | 0 | 0/11 |
| Cross-linked mNSP4 131K | 20 | 2/10 |
| NSP4 2-22 | 0 | 0/11 |
| Cross-linked NSP4 2-22 | 0 | 0/17 |
| NSP4 90-123 | 20 | 2/10 |
| Cross-linked NSP4 90-123 | 50 | 4/8 |
| NV 463-486 | 0 | 0/10 |
| Cross-linked NV 463-486 | 0 | 0/9 |

[a]rabbit hyperimmune anti-NSP4 114-135 serum administered just prior to administration of the peptide
[b]single amino acid substitution at residue 131

Example 17

Administration of Peptide NSP4 114–135 Results in Stunted Growth

Figure 9:
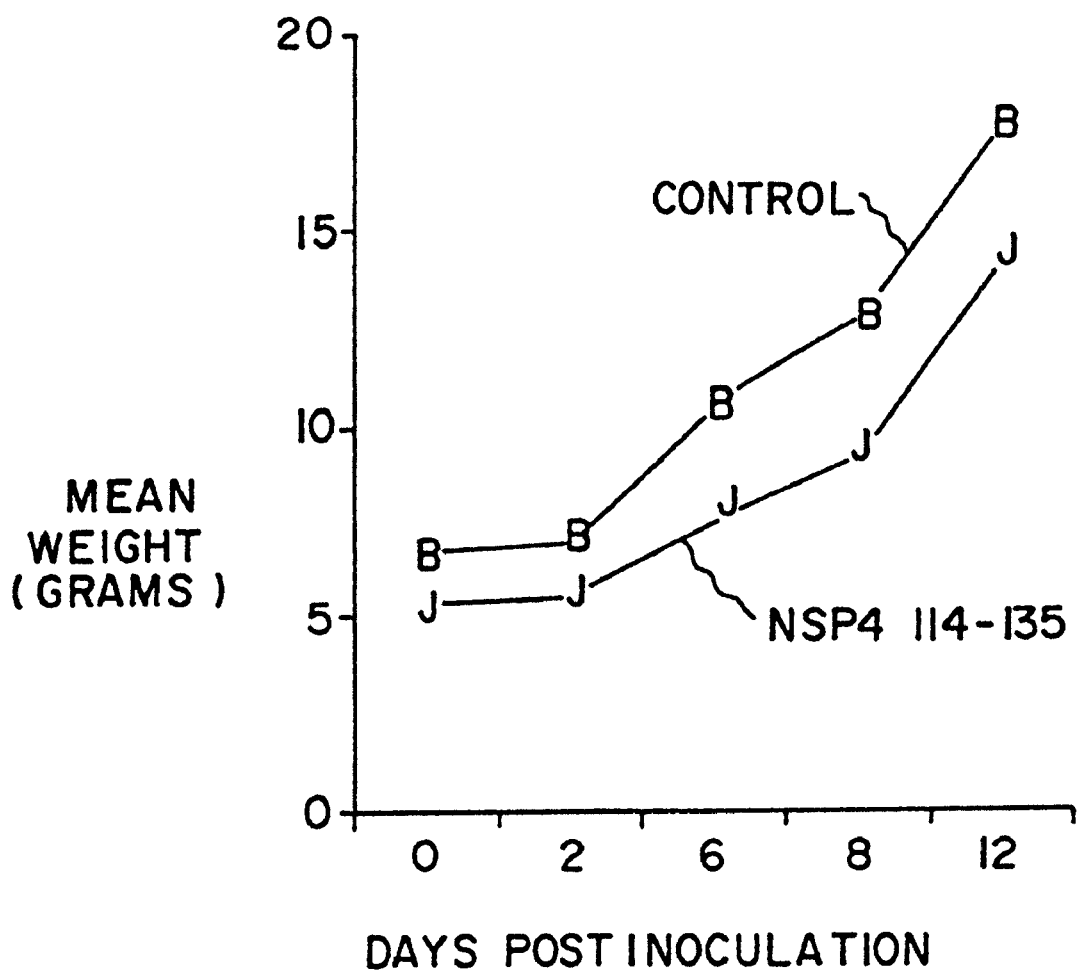

Animals given peptide three times per day for two days showed a rapid onset of severe diarrhea followed by stunted growth. The weight of these animals was 20–30% lower for three weeks after administration of peptide (FIG. 9). These results mimic characteristics of rotavirus disease in animals and children, including the fact that both may show decreased growth rates after multiple infections.

Example 18

Antiserum to NSP4 114–135 Peptide Blocks Induction of Diarrhea

In the absence of antibody, IP delivery of 50–100 nmol of NSP4 114–135 peptide induced diarrhea in 67% of the mice. IP inoculation of NSP4 114–135 peptide-specific antiserum 5 mins prior to IP delivery of peptide (50–100 nmol) resulted in a 90% reduction of disease. IP administration of normal rabbit serum prior to peptide did not block the diarrhea.

Example 19

NSP4 Antibodies Protect Against Virus-induced Disease

Figure 8:
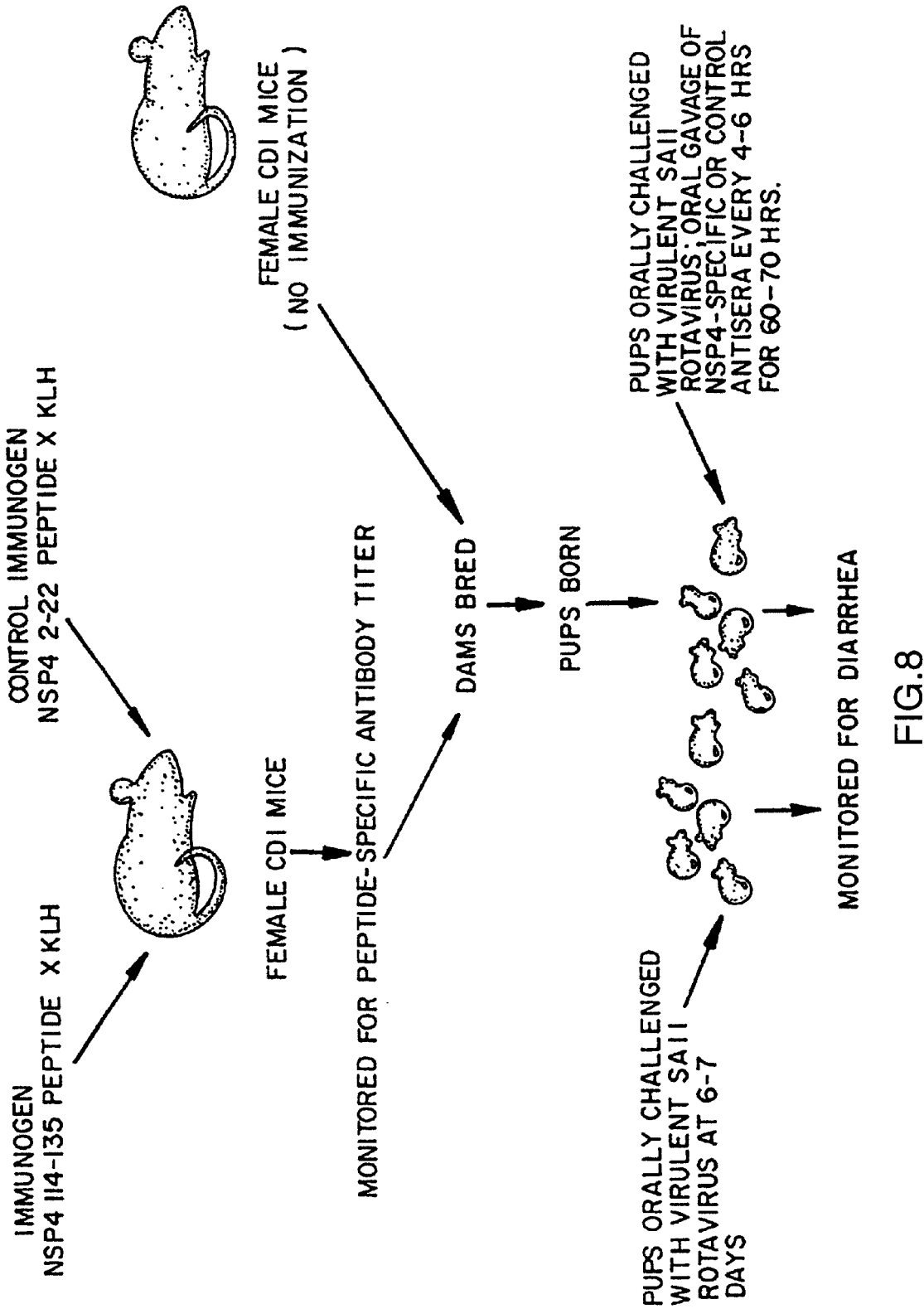

The potential of NSP4 antibodies to protect against virus-induced disease was tested by challenging pups, born to dams which were immunized with the NSP4 114–135 peptide or a control peptide, with a high dose of infectious SA11 virus, FIG. 8, left hand side. Diarrheal disease in pups born to dams immunized with the NSP4 114–135 peptide was significantly (Fisher's exact test) reduced in severity, duration, and in the number of pups with diarrhea (Table 4). The NSP4 2–22 peptide was used as a control peptide, as it does not induce diarrhea in pups.

TABLE 4

Immunization with NSP4 114-135 peptide induces protective immunity from infectious rotavirus challenge
Diarrhea Observed in Passively Immunized Pups[a]

| | % pups with diarrhea[b] | | | Mean |
|---|---|---|---|---|
| Peptide | Total | 2 days | 3 days | Diarrhea Score |
| NSP4 2-22 | 100% (16/16) | 63% (10/16) | 25% (4/16) | 3.5+ |
| NSP4 114-135 | 42% (5/12) *P = <0.001 | 17% (2/12) P = <0.025 | 0% (0/12) NS | 2.0+ |

*Fischer's Exact Test
[a]Pups born to dams immunized with NSP4 114-135 or control peptide were challenged with a high dose of infectious SA11 rotavirus and diarrheal disease was monitored.
[b]Significant protection against disease was seen in pups born to mothers immunized with NSP4 114-135 peptide.

In another experiment, young mouse pups were infected with SA11 virus, and NSP4 antiserum or control antiserum was orally administered every 4–6 hours for 60 hr, FIG. 8, right hand side. The pups administered NSP4-specific antibody had significantly reduced diarrheal disease compared to animals given no treatment, rabbit pre-immune serum or normal rabbit serum (NRS), (Table 5). These data show the potential of NSP4 antibodies to block rotavirus-induced disease.

TABLE 5

Protection from Rotavirus Severe Diarrhea (≧3+) after Administration of NSP4-specific Antibody

| Treatment | | Total # with Diarrhea | | Onset of Diarrhea (hpi) | | Illness at 71–77 hpi | | Illness at 90–110 hpi | |
|---|---|---|---|---|---|---|---|---|---|
| None | Exp. 1 | 7/7 | (100%) | 27–28 | 5/7 | 4/7 | (57%) | 2/7 | (29%) |
| | Exp. 2 | 10/10 | (100%) | 22–23 | 6/10 | 4/10 | (40%) | 3/10 | (30%) |
| Rab pre immune | Exp. 1 | 8/8 | (100%) | 27–28 | 5/8 | 4/8 | (50%) | 0/8 | (0%) |
| NRS | Exp. 2 | 13/13 | (100%) | 22–24 | 3/14 | 2/13 | (15%) | 0/13 | (0%) |
| Rabbit anti-NSP4 | Exp. 1 | 5/10* | (50%) | 27–28 | 3/10 | 1/8 | (12%) | 0/8 | (0%) |
| | Exp. 2 | 2/13* | (15%) | 27–28 | 1/13 | 0/10 | (0%) | 0/10 | (0%) |
| Rabbit anti-NSP4 | Exp. 1 | ND | | ND | | ND | | ND | |
| Anti-NSP4 114-135 peptide | Exp. 2 | 2/9* | (22%) | 22–23 | 1/9 | 0/9 | (0%) | 0/9 | (0%) |

TABLE 5-continued

Protection from Rotavirus Severe Diarrhea (≧3+) after
Administration of NSP4-specific Antibody

| Treatment | Total # with Diarrhea | Onset of Diarrhea (hpi) | Illness at 71–77 hpi | Illness at 90–110 hpi |
|---|---|---|---|---|

*Statistically significant compared to the pre immune or no treatment groups; Fischer's exact (2-tailed). ND = not done.

Example 20

Electrophysiological Analyses

The effects of a peptide, and known $Ca^{2+}$- and cAMP-elevating agonists were tested on unstripped mouse intestinal mucosal sheets in modified Ussing chambers (Giannella

TABLE 6

Electrophysiological Analyses of CD1 Mice Ileal Mucosa

| Agonist Treatment[a] | 19–22 Day Old Mice $\Delta I_{SC}$ ($\mu A/cm^2$)[b] | | 35 Day Old Mice $\Delta I_{SC}$ ($\mu A/cm^2$)[b] | |
|---|---|---|---|---|
| Forskolin (FSK), 5 μM | 44 ± 0.7 | (n = 8) | 41 ± 7 | (n = 5) |
| Carbachol (Cch), 5 μM | 9 ± 2 | (n = 8) | 14 ± 4 | (n = 5) |
| NSP4 114-135 peptide, 5 μM[c] | 3 ± 0.2 | (n = 4) | 0.4 ± 0.4 | (n = 4)[d] |
| FSK (5 μM) = Cch (5 μM) | 63 ± 10 | (n = 5) | 64 ± 9 | (n = 6) |
| FSK (5 μM) + NSP 4 114-135 peptide (5 μM) | 64 ± 5 | (n = 7) | 43 ± 9 | (n = 5) |

[a]The mean resting conductance for the ileal mucosal sheets prior to agonist treatment was 10.4 ± 4.8 msemens (ms)/cm² (n = 32) for the 19–22 day old mice and 12.3 ± 3.8 ms/cm² (n = 25) for the 35 day old mice.
[b]The $\Delta I_{SC}$ was calculated by subtracting the stimulated $I_{SC}$ measurement from the $I_{SC}$ measured immediately before the addition of agonist. All agonist stimulated values were significantly different (p < 0.001, unpaired t-test).
[c]NSP4 114-135 peptide is active when added to either surface of the mucosa.
[d]For n = 3, there was no response with peptide; for n = 1, the response was 2 μA/cm² et al., 1983; Currie et al., 1992; Field et al., 1978 and Forte et al., 1992). Addition of forskolin (FSK, cAMP agonist) and carbachol (Cch, cholinergic agonist which mobilizes $Ca^{2+}$) to normal mouse ileal mucosa resulted in measurable elevations in Cl-secretory short circuit current (Isc, Table 6). Addition of either 5 μM of NSP4 114–135 peptide (cross-linked to itself for enhanced stability) or 5 μM of Cch to mucosal sheets of 19–22 day old CD1 mice induced small (3 or 9 μA/cm2, respectively) and transient (1–2 min) increases in Isc. When the mucosal sheets were exposed to 5 μM of the cAMP-mobilizing agonist, FSK, larger increases in Isc (44 μA/cm2) were elicited that reached sustained levels within 2–3 min. After FSK pretreatment, challenge of the mucosa with either peptide or Cch resulted in much larger increases in mucosal Isc (64 or 63 μA/cm2, respectively); both the peptide and Cch potentiated the response to FSK. All of the responses to agonists were sensitive to bumetamide and treatment of ileal mucosal sheets with cross-linked control NSP4 2–22 peptide did not induce a response. Addition of Cch to 19–22 day old mouse mucosal sheets which had been pretreated with peptide alone, or peptide in combination with FSK, had minimal or no additional effect on Isc. This subsequent loss of sensitivity to the $Ca^{2+}$-elevating agonist (Cch) after peptide pretreatment suggests that the NSP4 peptide increases Isc through changes in intracellular $Ca^{2+}$ ($[Ca^{2+}]_i$). Addition of Cch to mucosa from a 35 day old mouse again elicited a small (14 μA/cm²) and transient (1–2 min) response that potentiated the effect of FSK (64 μA/cm²), whereas there was no or minimal increase in Isc when the NSP4 114–135 peptide was added alone or with FSK to the 35 day old mouse mucosal sheets (Table 6).

The electrophysiological responses from 19 day old mice initially seem paradoxical to the biological data since measurable secretion was not observed as diarrhea in this age animal. Diarrhea likely was not seen in these older animals because of fluid reabsorption by the colon. This hypothesis was tested by IL administration of 200 nmol of NSP4 114–135 or control peptide to 19 day old pups. At 4 hrs post inoculation, the mice were sacrificed and the intestines were tied off, removed, weighed, and the length measured. The pups given NSP4 114–135 peptide showed significant fluid accumulation when compared to the control pups although no diarrhea was seen in any animals.

It is anticipated that younger mice would show a greater increase in Isc than that seen in the 19 day old mucosa. However, intestinal mucosa from younger mice (<19 days) could not be mounted efficiently into the Ussing chambers due to their small size; such experiments in very young mice will require the development of new methods to measure Cl-secretion in vitro. Nonetheless, the NSP4 114–135 peptide did not augment secretion in 35 day old mice, correlating the age-dependence seen in vivo.

Example 21

Live Rotavirus and NSP4 Cause Diarrhea in CFTR Knock-out Mice

Cystic Fibrosis is caused by a defect in the gene that codes for the cAMP-activated chloride channel called CFTR. As a result of the defect, the CFTR channel is defective and chloride secretion—and hence water secretion—is greatly diminished. Without sufficient secretion of water, membranes accumulate excessive amounts of mucous and eventually become obstructed.

Peptide or virus was administered to 5–7 day old CFTR knock-out mice—mice homozygous for a mutation that disables the CFTR coding region—and got diarrhea in 100% of the cases for virus and cross-linked peptide or in 80% of the animals given 100 nmoles of non-crosslinked NSP4 114–135 peptide. This demonstrates that NSP4 stimulation of chloride secretion through a $Ca^{2+}$-dependent channel can compensate for the lack of secretion through the defective cAMP-dependent CFTR channel.

Example 22

HIV gp120 Causes Diarrhea in Mice

Human immunodeficiency virus (HIV) is associated with wasting or Slim disease. To determine whether the HIV glycoprotein 120 (gp 120) is an enterotoxin, 6–7 day old Balb/C mouse pups were inoculated with purified gp120. Diarrhea was observed in 100% of the animals. Other proteins of HIV or other retrovirus or other proteins of other viruses may be found to have similar functional activity-i.e., to directly induce diarrhea.

Example 23

Identification of Small Molecule Inhibitors of NSP4/receptor Interaction.

The above data demonstrate that effective treatment of rotavirus-induced diarrhea can be accomplished through inhibition of NSP4's interaction with its receptor. Identification of small molecule inhibitors of NSP4 is well within the ability of the ordinary practitioner according to known techniques. Small molecule inhibitors are known in the art to refer to any ligand which can bind to a target molecule with sufficient affinity to inhibit the target molecule's activity. Libraries of small molecules, such as random peptide libraries, random oligonucleotide libraries, and pharmaceutical drug libraries, are available either according to known techniques or commercially, and may be quickly and easily screened against a purified target molecule for small molecules that bind with high affinity to a target molecule. Examples include the "FliTrx Peptide Library," (Invitrogen) and the SELEX technology.

Example 24

Construction of Attenuated Rotavirus Strains by Incorporation of a Selected NSP4 Amino Acid Sequence The sequence of gene 10, the gene encoding NSP4, was determined for a pair of virulent and tissue culture attenuated porcine rotavirus strains. Double stranded RNAs were extracted from an intestinal homogenate from a piglet infected with a virulent strain of porcine rotavirus (OSU-v, SEQ.ID.NO:7) and from a piglet infected with a tissue culture attenuated OSU virus (OSU-a, SEQ.ID.NO:8). Gene 10 from the dsRNAs was amplified by RT/PCR using primers from the SA11 gene 10 sequence. cDNAs from these two strains were cloned and sequenced. Comparisons of the gene 10 sequences of these two strains and other rotavirus strains have suggested that the amino acid sequence between amino acids 131 to 140 are important in pathogenesis. The amino acid sequence of the NSP4 protein from the attenuated strain (OSU-a) was compared to that of the virulent strain (OSU-v) and the results are presented in FIG. 10. The positions at which the two sequences differ are shown in bold. Mice infected with virulent virus develop diarrhea while those infected with attenuated virus do not.

Gene 10 encoding NSP4 protein from each of these two strains has been cloned and expressed in a baculovirus expression system and purified. The purified NSP4 proteins were tested for their ability to induce diarrhea in mouse pups. The NSP4 protein from the virulent strain causes increased intracellular calcium concentration and induced diarrhea while that of the attenuated strain did not. These results indicate that avirulence is associated with mutations in gene 10 and indicate that certain amino acid positions of the NSP4 protein are critical for diarrhea induction. The identification of critical residues makes it a routine matter for one skilled in the art to determine whether a given rotavirus is likely to cause diarrhea by comparing the amino acid sequence of the NSP4 protein to known sequences. For example, comparisons can be made using virulent and avirulent pairs of amino acid sequences. In addition, the identification of NSP4 sequences that correlate to an attenuated phenotype makes it a routine matter to construct attenuated reassortment viruses that include such an NSP4 sequence, using techniques that are well known to those skilled in the art. This permits the construction of rotaviruses for use as vaccines that retain the antigenicity of the virulent strain yet display an attenuated phenotype as a result of the incorporation into the genome of the virus a nucleic acid coding for an NSP4 protein having a selected sequence.

Example 25

Preparation and use of an NSP4 Toxoid

Vaccines comprising NSP4 in the form of a toxoid may be prepared from purified NSP4 protein, NSP4 114–135, NSP4 120–147, NSP4 112–175 or NSP4 112–150. The purified protein can be chemically treated, using known techniques, to inactivate the biological activity of the NSP4 protein while retaining the immunogenicity. For example, the purified protein may be treated with a 10% solution of formaldehyde at about 37 C for about an hour. One skilled in the art will recognize that other equivalent protocols to produce a toxoid may be employed without deviating from the spirit of the invention. After chemical treatment the toxoid will typically be washed with buffer, for example phosphate buffered saline or the like, and formulated into a vaccine. The toxoid may be in solid form such as adsorbed to alum or the like. Alternatively, the toxoid may be in solution in any pharmaceutically acceptable liquid. The toxoid may be administered as a vaccine in the absence of adjuvant. A vaccine formulated with the toxoid may include adjuvants including but not limited to alum, Freund's complete and incomplete adjuvants, Ribi's adjuvant, bacterial and mycobacterial cell wall components and derivatives thereof, liposomes and any other adjuvant formulation known in the art. Vaccines thus formulated may be administered using parenteral or mucosal routes such as by intraperitoneal, intranasal, intragastric, subcutaneous, intramuscular, or rectal application.

Example 26

Characterization of the Receptor for NSP4

The human intestinal cell line HT29 was assayed for sensitivity to NSP4. In response to purified NSP4, these cells showed an increase in intracellular calcium levels. When these cells are pre-treated with trypsin, the response is ablated. The binding of radiolabelled NSP4 protein to responsive cells is dose-dependent and saturable as would be expected for a receptor dependent phenomenon. Taken together, these two results demonstrate that NSP4 binds to a protein receptor. Recent tests with respiratory epithelial cells have demonstrated that these cells do not respond to NSP4 and do not bind radiolabelled NSP4 protein. It is well within the ability of one of ordinary skill in the art to identify the receptor by expression cloning in these nonresponsive cells that do not bind NSP4. The mRNA from a responsive cell can be isolated using standard techniques and reverse transcribed into cDNA. This cDNA can then be inserted into a vector and then used to transform the nonresponsive cell line. One skilled in the art is cognizant that any vector may be used in this invention. Exemplary vectors include, but are not limited to, insect expression vectors, bacteria expression vectors, mammalian expression vectors or viral expression vectors. Alternatively, the genomic DNA from the responsive cells may be inserted into a vector and used to transform the nonresponsive cell line. The transformed cells will be screened for the expression of the receptor using routine techniques, for example, by screening for cells capable of binding radiolabelled NSP4. Cells that express the receptor will be isolated.

Example 27

Preparation of SA 11 Clone 3

Plaque-purified simian rotavirus SA11 clone 3 (SA11, serotypes P3B[2],G3) was cultivated in monkey kidney MA104 cells in the presence of trypsin. The 50% diarrhea dose (DD50) of the SA11 virus stock for Balb/C suckling mice was $1.4 \times 10^4$ PFU. A stock of the wild type murine rotavirus ECwt (P[16],G3) was prepared from the infected intestines of orally inoculated five-day-old mouse pups (Feng et al., 1994 and O'Neal et al., 1997). The titer of this ECwt stock in mouse pups was $2 \times 10^8$ DD50 per ml.

Example 28

Preparation of SA11-NSP4 112–175

NSP4 112–175 was produced in an insect cell suspension culture system and purified by immunoaffinity chromatography as reported elsewhere (Zhang et al., 2000). The purified NSP4 112–175 was lyophilized, and stored at 4 C in a dessicator until used. SDS-15% PAGE/silver staining and Western blot were used to evaluate protein purity.

Example 29

Preparation of SA11 NSP4 and VP6

Full-length NSP4 production and purification were conducted in an insect cell suspension system, purified by FPLC and irnmunoaffinity chromatography (Zhang et al., 1998 and Tian et al., 1996). VP6 was expressed in SF9 cells grown in optimized serum-free media, SF90011 SFM (Gibco, Grand Island, N.Y.), and purified by CsCI isopycnic centrifugation (Zeng et al., 1996).

Example 30

Detection of Serum Antibodies by ELISA

All ELISAs were performed on 96-well polyvinyl chloride microtiter plates (Dynatech, McLean, Va.) (Ciarlet, et al., 1998 and Johansen, et al., 1999). To detect the mouse serum antibodies, the coating concentration of NSP4 was 24 µg/ml, NSP4 112–175 was 8 µg/ml, and VP6 was 15 µg/ml. Horseradish peroxidase-conjugated goat anti-mouse Ig (H+L) (Southern Biotechnology Associates, Inc., Birmingham, Ala.) was used to detect the bound mouse antibodies. The optimum dilution of antibody conjugates was determined by checkerboard titration. TMB peroxidase substrate, tetramethylbenzidine and $H_2O_2$, was used as chromogenic reagent (Kirkegaard and Perry Laboratories, Gaithersburg, Md.). Optical densities (O.D.) at 450 nm were measured with an ICN Flow Titertech Multiscan Plus MK11 plate reader (McLean Va.). Antibody titers were defined as the reciprocal of the highest dilution giving a net O.D. value (O.D. value of detected serum minus O.D. value of pooled pre-immune serum) higher than 0.1.

Example 31

Plaque Assay to Detect Infectious Virus in the Intestines of Rotavirus SA11-challenged Suckling Mice The level of replication of SA11 in the intestine of suckling mice was determined by titration of infectious virus by plaque assay (Ramig 1988). Similar experiments could not be performed with ECwt challenged mice because the ECwt virus does not replicate efficiently in vitro. Additional mock-infected (PBS) mice were also included in this experiment as controls. The entire intestinal tract was removed from one SA11- and mock-infected mouse pup from 1–7 days post infection (DPI). The experiment was repeated once, for a total of two mouse pups for every timepoint. Each intestinal tract was homogenized separately in 1 ml of serum-free medium 199, extracted with an equal volume of Freon (1,1,2-Trichloro-1,2,2-trifluoroethanol, Fisher Scientific, Springfield, N.J.), the water soluble phase was collected and treated with 20 µg/ml of trypsin for 30 min at 37 C. Each intestinal sample was tested in duplicate for virus titer in plaque assays with $MA10^4$ cells.

Example 32

Preparation of Baculovirus Recombinants

S.frugiperda insect cells (Sf9) were grown and maintained in TNM-FH (Hinks) medium (Gibco, Grand Island, N.Y.) containing 10% fetal bovine serum (FBS). Baculovirus recombinants encoding the following rotavirus proteins were used: pFastBac/SA11–10 112–175 [NSP4 112–175 of SA11 cl 3] (Zhang et al., 2000), pAc461/SA11–10 [NSP4 of SA11 cl 3] (Au et al., 1989), and pAc4461/SA11–6 [VP6 of SA11 cl 3] (Estes et al., 1987).

Example 33

Immunization of Dams With NSP4 aa 114–175

NSP4 aa 112–175 was expressed in and purified from the medium of insect Sf9 cells. Purified NSP4 112–175 contained a single band with an apparent molecular weight of 7,000 identified by SDS-15% PAGE/silver staining (FIG. 11A, arrow). A single band was also visualized by Western blot using rabbit anti-NSP4 peptide 114–135 (FIG. 11B, arrow), rabbit anti-NSP4 full-length antiserum, or a rabbit anti-NSP4 peptide 120–147 antiserum.

Seronegative female mice were subcutaneously and intramuscularly immunized with 14 µg NSP4 112–175 plus 20 µg Quillaja saponaria [adjuvant QS-21 (Kensil, et al., 1991)] (NSP4-dam) or with 20 µg QS-21 alone (QS-21-dam). The first inoculation was followed by a booster two weeks later at which time breeding was begun. A second booster was given on the tenth day of bre e ding. Each dam was tail-bled on the indicated days for determination of antibodies by ELISA.

The control group (QS-21-dam) was inoculated with QS-21 alone. In the initial experiments, pups were nursed by their own dams. The serum antibody titers in NSP4-dams, QS-21-dams and all pups were determined on 0, 7, and 16 DPP. The serum antibody titers to NSP4 aa112–175 and to NSP4 full-length detected by ELISA were essentially the same (FIG. 12A and FIG. 12B). The results show that (i) ser a from NSP4-dams had antibody geometric mean titers (GMT) as high as 9×10 to both NSP4 aa112–175 and NSP4 full-length; (ii) serum GMT were maintained throughout the experimental period in the NSP4-dams; (iii) NSP4-pups acquired only 3% of NSP4-dam titers transplacentally (NSP4-pups on 0 DPP), but the maj ority of NSP4-specific antibody was obtained by lactogenic transfer (NSP4-pups on 7 and 16 DPP); (iv) the sera from QS-21-dams lacked antibody to either NSP4 112–175 or to NSP4 full-length; and (v) sera from the QS-21-pups lack ed detectable antibody to NSP4, similar to their mothers, throughout the experimental period.

Example 34

Cross-nursing of Neonates Induces Changes in Serologic Antibody Levels

Within 4 hrs of birth, neonatal pups born to NSP4-dams and QS-21-dams were immediately segregated from their biological mothers and cross-nursed by the dams in the other group.

Cross-nursing of neonates induces dramatic changes in serologic antibody levels against both NSP4 aa112–175 and full-length NSP4 in the pups. To compare the importance of transplacental and lactogenic transfers of antibody, cross-nursing experiments wer e performed. Pups were removed from their biological mothers within 4 hrs post parturition and cross-nursed. The results in FIG. 13A and 13B show that (a) sera from the NSP4-pups cross-nursed by QS-21-dams maintained thei r low antibody status (GMT, 3×10$^3$) during the experimental period, at levels similar to their antibody level at birth (white bars); and (b) by 7 DPP, QS-21-pups cross-nursed by NSP4-dams acquired antibody titers in the sera (GMT, 9×10$^4$) similar to those of their nursing NSP4-dams which were maintained throughout the experimental period (gray bars). Cross-nursing experiments confirmed that 97% of antibody in pups was acquired from lactogenic transfer and only 3% from transplacental transfer.

Example 35

Immunization of Dams With NSP4 112–175 Induces Protection of Suckling Mice Against SA11-induced Diarrhea At 7 DPP, each pup was challenged by stomach gavage with either 20 diarrhea dose 50% (DD50) of SA11 or 10 DD50 of ECwt in 50 μl of endotoxin-free PBS. Virus inocula were not trypsin-activated prior to inoculation. All cages were coded and individual mice were checked for diarrhea daily for 7 or 8 days after inoculation by gentle palpation of their abdomen. Stool classification was: 0, no stool; 1, normal stool; 2, normal stool accompanied with yellow pasty stool; 3, all yellow pasty stool; 4, milky-liquid stool. The pups with a stool score $\geq 2$ were considered to have diarrhea.

To evaluate whether antibody to NSP4 112–175 can mediate protection against rotavirus-induced diarrhea, pups were challenged orally with 20 DD50 of SA11 at 7 DPP and checked for diarrhea 0–7 DPI. All QS-21-pups developed diarrhea between 2–4 DPI which generally lasted at least two days (Table 7). Only 50% of the NSP4-pups developed diarrhea and the duration of diarrhea was generally limited to one day. The percentage of NSP4-pups with diarrhea compared to QS-21-pups was significantly lower (P=0.007). The mean diarrhea scores of NSP4-pups were also lower (2.8) compared to QS-21-pups (3.5).

TABLE 7

Passively acquired antibody to NSP4 aa112-175 protects pups from SA11-induced diarrhea

| Group | Pups from dams immunized with | Pups with diarrhea % at indicated DPI | | | | Mean diarrhea score[a] |
|---|---|---|---|---|---|---|
| | | 2 | 3 | 4 | 7 | |
| A | QS-21 | 76% (8/12) | 100% (12/12) | 33% (4/12) | 100% (12/12) | 3.5 |
| B | NSP4 aa112-175 Plus QS-21 | 0% (0/12) P = 0.006[b] | 50% (6/12) P = 0.007[b] | 8% (1/12) NS[c] | 50% (6/12) P = 0.007[b] | 2.8 |

[a]The scores were calculated only for pups with diarrhea 2–4 DPI. Mean diarrhea score = Total diarrhea scores/Total diarrhea times.
[b]Fisher's exact compared to group A.
[c]NS, not significant by Fisher's exact test, P > 0.05.

Example 36

Passively Acquired Antibody to Simian Rotavirus SA11 NSP4 112–175 Protects Pups

NSP4 112–175 was administered parenterally with the saponin adjuvant QS-21, rather than Freund's adjuvant, because QS-21 may be licensed for use in humans and is more potent than aluminum phosphate (Ciarlet et al., 1998).

It was tested whether passively acquired antibody to simian SA11 NSP4 112–175 could protect pups from a heterotypic challenge with 10 DD50 of virulent murine rotavirus ECwt. Similar to the results with homotypic virus challenge with SA11, fewer NSP4-pups (44%) were not protected from ECwt-induced diarrhea, while 100% of QS-21-pups developed diarrhea (P=0.02) (Table 8). The mean diarrhea scores in the NSP-4 pups (2.8) were also lower compared to the QS-21-pups (3.3) (Table 8). In addition, the onset of diarrhea in NSP4-pups was later and was of shorter duration than in the QS-21-pups. Thus, NSP4 112–175 administered parentally induced protection of suckling mice against diarrhea induced by heterotypic murine ECwt rotavirus.

detectable in any of the dams and pups at 0 DPI, but was detectable at 12 DPI (FIG. 15). The serum antibody titers to VP6 in the NSP4-pups (GMT, $3\times10^3$) were significantly higher than those in the QS-21-pups (GMT, $3\times10^2$) (P<0.001). The serum antibody titers to VP6 in the NSP4-dams (GMT, $8\times10^3$) were also significantly higher than

TABLE 8

Passively acquired antibody to simian rotavirus SA11 NSP4 112-175 protects pups from murine rotavirus $EC_{wt}$ induced diarrhea

| Group | Biological dams immunized with | Pups with diarrhea % at indicated DPI | | | | | | | | Mean diarrhea score[a] |
|---|---|---|---|---|---|---|---|---|---|---|
| | | 2 | 3 | 4 | 5 | 6 | 7 | 8 | 0–8 | |
| A | QS21 | 29% (2/7) | 100% (7/7) | 100% (7/7) | 100% (7/7) | 86% (6/7) | 71% (5/7) | 14% (1/7) | 100% (7/7) | 3.3 |
| B | NSP4 aa112-175 Plus QS21 | 0% (0/9) NS[c] | 44% (4/9) P = 0.028[b] | 44% (4/9) P = 0.028[b] | 33% (3/9) P = 0.010[b] | 0% (0/9) P = 0.001[b] | 0% (0/9) P = 0.005[b] | 0% (0/9) NS[c] | 44% (4/9) P = 0.02[b] | 2.8 |

[a]The scores were calculated only for pups with diarrhea 208 DPI. Mean diarrhea score = Total diarrhea scores/Total diarrhea times.
[b]Fisher's exact compared to group A.
[c]NS, not significant by Fisher's exact test, P > 0.05.

Example 37

Antibody to NSP4 Reduced Virus Replication

Rotavirus replication is reduced in pups delivered to and nursed by the dams immunized with NSP4 112–175 plus QS-21. To investigate the possible effect of passively acquired antibody to NSP4 on rotavirus replication, the infectious virus titers of SA11 in the intestines of a subset of pups from NSP4-dams and QS-21-dams were determined in two separate experiments. No virus was detected from the intestines of either of the mock-infected control pups (FIG. 14A, FIG. 14B and FIG. 14C). The yields of infectious SA11 were consistently higher and were detected for a longer period of time in the two QS-21-pups, compared to virus titers in the two NSP4-pups.

Example 38

Immunization of Dams With NSP4 112–175 Induces Higher Serologic Antibody Titers Against SA11 VP6

Dams were immunized with NSP4 aa112–175, both the dams and pups were orally challanged with rotavirus SA11.

This immunization induced higher serologic antibody titers against SA11 VP6 in both dams and pups after pups were orally challenged with rotavirus SA11. It was also determined whether pre-existing antibody to NSP4 would alter the kinetics of antibody acquisition to rotavirus structural proteins by testing the serum antibody titers to VP6. NSP4-pups and QS-21-pups, but not dams, were orally challenged with 20 DD50 SA11. Antibody to VP6 was not those in the QS-21-dams (GMT, $2\times10^3$) (p=0.005). These results indicated that (i) not unexpectedly, infectious rotavirus was transmitted from the inoculated pups to their uninoculated dams; (ii) pre-existing actively acquired antibody to NSP4 in the dams enhanced the immune response to VP6, a non-related immunogen.

Example 39

Cross-nursed Pups Show Protection From Lactogenic Antibody

In a separate cross-nursing and challenge experiment (Table 9), nine QS-21-pups (group A) and 10 NSP4-pups (group B) were nursed by their biological mothers during the experimental period. Within 4 hrs of birth, 13 QS-21-pups were transferred to and cross-nursed by NSP4-dams (group C), and 15 NSP4-pups were transferred to and cross-nursed by QS-21-dams (group D) during the experimental period. All the pups were orally challenged with 20 DD50 SA11. As observed in the initial challenge experiment (Table 8), all of the QS-21-pups in group A developed diarrhea and only 50% of the NSP4-pups in group B developed diarrhea (P=0.026) and the mean diarrhea scores in group B (2.6) were lower than group A (3.3). Only 46% of the QS-21-pups cross-nursed by NSP4-dams (group C) developed diarrhea, their mean diarrhea score was 2.8 and they were significantly protected against SA11 diarrhea (p=0.010) compared to QS-21-pups (group A). The onset of diarrhea in NSP4-pups cross-nursed by QS-21-dams (group D) was delayed; the percentage of pups with diarrhea was significantly different at 2 dpi compared to QS-21-pups in group A (0% vs. 335 of diarrhea, P=0.041). The NSP4-pups cross-nursed by QS-21-dams (group D) had a lower diarrhea score (2.9) and showed partial protection (27%) against diarrhea relative to the QS-21-pups in group A, but protection was not significantly higher (p=0.090).

TABLE 9

Protection against SA11-induced diarrhea in cross-nursed pups shows protection is from lactogenic antibody

| Group | Biologic dams immunized with | Cross-nursing dams immunized with | Pups with diarrhea % at indicated DPI | | | | Mean diarrhea score[a] |
|---|---|---|---|---|---|---|---|
| | | | 2 | 3 | 4 | 7 | |
| A | QS-21 | QS-21 | 33% (3/9) | 100% (9/9) | 56% (5/9) | 100% (9/9) | 3.3 |

TABLE 9-continued

Protection against SA11-induced diarrhea in cross-nursed pups shows protection is from lactogenic antibody

| Group | Biologic dams immunized with | Cross-nursing dams immunized with | Pups with diarrhea % at indicated DPI | | | | Mean diarrhea score[a] |
|---|---|---|---|---|---|---|---|
| | | | 2 | 3 | 4 | 7 | |
| B | NSP4 aa112-175 Plus QS-21 | NSP4 aa112-175 Plus QS-21 | 0% (0/10) NS[c] | 40% (4/10) P = 0.008[b] | 20% (2/10) NS[c] | 50% (5/10) P = 0.026[b] | 2.6 |
| C | QS-21 | NSP4 aa112-175 Plus QS-21 | 0% (0/13) P = 0.045[b] | 39% (5/13) P = 0.004[b] | 31% (4/13) NS[c] | 46% (6/13) P = 0.010[b] | 2.8 |
| D | NSP4 aa112-175 Plus QS-21 | QS-21 | 0% (0/15) P = 0.041[b] | 73% (11/15) NS[c] | 27% (4/15) NS[c] | 73% (11/15) NS[c] | |

[a]The scores were calculated only for pups with diarrhea 2–4 DPI. Mean diarrhea score = Total diarrhea scores/Total diarrhea times.
[b]Fisher's exact test. Each group was compared to group A.
[c]NS, not significant by Fisher's exact test, P > 0.05.

Example 40

NSP4-VP2/VP6 Construct

A VP2-NSP4 fusion protein was constructed such that the coding region of gene 10, amino acids 112–175 without the stop codon, was cloned at the 3'-end of gene 2, amino acids 94–881 (SEQ.ID.NO:39 or SEQ.ID.NO:37). A linker composed of 3 alanine residues followed by one alanine and one serine residues were included between the two coding regions. This construct was cloned behind the p10 promoter of the baculovirus transfer vector pBAC4x-1. The entire coding region for VP6 (SEQ.ID.NO:38) was cloned behind the polyhedrin promotor in the pBAC4x-1 vector containing VP2-NSP4 fusion gene.

Following the standard co-transfection and recombinant baculovirus isolation, two baculorvirus recombinants were obtained. Virus-like particles (VLPs) were expressed, purified and analyzed by Western blot and electron microscopy. VP2-NSP4 and VP6 were detected by Western blot analysis using a polyclonal antibody against SA11 virus (FIG. 16). The presence of VP2-NSP4 was confirmed using an antiserum against NSP4. The linker used above is one possibility of making such a fusion protein with VP2. Others are possible (3 glycines for example) and this represents the first example of producing chimeric VP2/6 particles carrying other proteins of interest. A similar method could be used to make VLPs carrying proteins or peptides from other pathogens.

Example 42

In Vitro Assay for NSP4 120–147

Antiserum to the NSP4 peptide from the rotavirus strain SA11 reacts with NSP4 from at least one other strain, the porcine rotavirus strain OSU that is classified in a separate genetic group from the SA11 NSP4. An in vitro assay was developed to measure "biologic neutralizing activity" of antisera to regions of NSP4 that would block enterotoxin or signaling of the enterotoxin. First, NSP4 was tested to determine whether it can affect the transepithelial resistance (TER) of polarized epithelial cells grown on filters. It was found that polarized epithelial cells displaed high resistance and this resistance begins to decrease about 16 hours after the cells were treated with NSP4. Next, antibodies to different regions of NSP4 were added to examined if this drop in TER can be prevented "or neutralized". Antibodies to the NSP4 2–22 peptide, NSP4 114–135 peptide, NSP4 120–147 peptide, and to the full-length protein were tested. Preimmune serum for these peptides was also tested. These results show that pre-immune serum and antiserum to the 2–22 peptide do not block the drop in TER in cells treated with NSP4. The lack of neutralization by the antibody to 2–22 is consistent with the results that this peptide does not cause diarrhea in mice and immunization of mice with the peptide does not result in protective immunity. In contrast, antibodies to NSP4 114–135, NSP4 120–147 and to the full-length protein blocked the drop in TER in cells treated with NSP4 (FIG. 17 and Table 10). Thus, these data indicate that antibodies to NSP4 120–147 behave in a manner similarly to antibodies to NSP4 114–135. Since the 114–135 peptide causes diarrhea in mice and antibodies to NSP4 114–135 have also been shown to prevent diarrhea in mice, and the NSP4 120–147 peptide causes diarrhea in mice, these in vitro" neutralization data" support the claim that immunization with the peptide NSP4 120–147 will result in protection from diarrhea. This data demonstrates that if a peptide causes diarrhea in mice, antibody to that peptide will protect against diarrhea. The data indicate that the diarrhea is caused by activation by the peptide (or protein) of a cell signaling pathway that results in diarrhea. Antibody to these peptides likely stops this signaling process.

TABLE 10

Neutralization of effect of NSP4 on transepithelial cell resistance (TER) in polarized MDCK-1 cells

| Treatment of MDCK-1 cells | Reduction of TER after 16–24 hours | Interpretation- Neutralization of NSP4 effect? |
|---|---|---|
| Full-length NSP4 | Yes | Not applicable |
| Full-length NSP4 and pre-immune NSP4 2-22 serum | Yes | No |
| Full-length NSP4 and anti NSP4 2-22 serum | Yes | No |
| Full-length NSP4 and pre-immune NSP4 114-135 | Yes | No |
| Full-length NSP4 and anti NSP4 114-135 serum | No | Yes |
| Full-length NSP4 and pre-immune NSP4 120-147 | Yes | No |
| Full-length NSP4 and anti NSP4 120-147 serum | No | Yes |

All patents and publications mentioned in the specification are indicative of the level of those skilled in the art to which the invention pertains. All patents and publications are herein incorporated by reference to the same extent as if each individual publication was specifically and individually indicated to be incorporated by reference.

REFERENCES

A. P. Morris S. A. Cunningham, A. Tousson, D. J. Benos, R. A. Frizzell, Am J. Physiol. 266, C254 (1994).

A. Z. Kapikian and R. M. Chanock, in Virology, B. N. Fields and D. M. Knipe, Eds. (Raven Press, New York, 1996) chap. 55.

American Academy of Pediatrics. 1998. Prevention of rotavirus disease: Guidelines for use of rotavirus vaccine. *Pediatrics* 102:1483–1491.

Au, K. S., Chen, W. K., Burns, J. W., and Estes, M. K. 1989. *J Virol.* 63:4553–4562.

B. R. Grubb, Am. J. Physiol. 268, G505 (1995).

Ball, J. M., Tian, P., Zeng, C. Q. Y., Morris, A. P., and Estes, M. K. 1996. *Science* 272:101–104.

Bern, C., Martines, J., de Zoysa, I., and Glass, R. I. 1992. The magnitude of the global problem of diarrhoeal disease: a ten-year update. *Bull. World health Organ.* 70:705–714.

C. L. Sears, R. L. Guerrant, J. B. Kaper, in Infections of the Gastrointestinal Tract, M. J. Blaser, P. D. Smith, J. I. Ravdin, H. B. Greenberg, R. L. Guerrant, Eds. (Raven Press, New York, 1995), chap. 44;

C. Q.-Y. Zeng, M. J. Wentz, J. Cohen, M. K. Estes, R. F. Ramig, J. Virol., in press (1996).

CDC MMWR. 1999. Intussusception among recipients of rotavirus vaccine-United States. 1998–1999. Morb. Mortal. WKLY. Rep. 48:577–581.

Ciarlet, M., and Conner, M. E. 2000. In J. Gray and U. Desselberger (ed.), Methods in Molecular Medicine. Humana Press Inc., New York.

Ciarlet, M., Crawford, S. E., Barone, C., Bertolotti-Ciarlet, A., Ramig, R. F., Estes, M. K., AND CONNER, M. E. 1998. *J. Virol.* 72:9233–9246.

Ciarlet, M., Liprandi, F., Conner, M. E., and Estes, M. K. 2000. *Arch. Virol.* 145:371–383.

Cunliffe, N. A., Woods, P. A., Leite, J. P., Das, B. K., Ramachandran, M., Bhan, M. K., Hart, C. A., Glass, R. I., and Gentsch, J. R. 1997. *J. Med. Virol.* 53:41–50.

D. Y. Graham, J. W. Sackman, M. K. Estes, Dig. Dis. Sci. 29, 1028 (1984).

Desselberger, U., and Estes, M. K. 2000. In J. Gray and U. Desselberger (ed.), Methods in Molecular Medicine. Humana Press Inc., New York. p 239–258.

Dong, Y. J., Zeng, C. Q. Y., Ball, J. M., Estes, M. K., and Morris, A. P. 1997. *Proc. Natl. Acad. Sci. U.S.A.* 94:3960–3965.

Dyson, et al. Ann. Rev. Biophys. Biophysical Chem.17, 305 (1988).

Dyson, et al., Biochemistry, 31, 1458 (1992).

Dyson, et al., Biophysical Chem. 20, 519 (1991).

Dyson, et al., FASEB J. 9, 37 (1995).

Dyson, et al., J. Mol. Biol. 201, 161 (1988).

Dyson, et al., J. Mol. Biol. 201, 201 (1988).

E. Kaiser, R. L. Colescott, C. D. Bosinger, P.I. Cook, Anal. Biochem. 34 595 (1970).

Estes, M. K. 1996. Rotavirus and their replication, p 1625–1655. In B. N. Fields, D. M. Knipe (ed.), Virology $3^{rd}$ ed. Raven Press, New York.

Estes, M. K., Crawford, S. E., Penaranda, M. E., Petrie, B. L., Burns, J. W., Chan, W. K., Ericson, B. L., Smith, G. E., and Summers, M. D. 1987. *J. Virol.* 61:1488–1494.

Evans, D. G., Evans, D. J. Jr., Opekun, A. R., and Graham, D. Y. 1988. *FEMS Microbiol. Immunol.* 1:117–125.

Feng, N., Burns, J. W., Bracy, L., and Greenberg, H. B. 1994. *J. Virol.* 68:7766–7773.

G. P. Johnson et al., Anal. Chem. 58, 1084 (1986).

G. W. Both, L. J. Siegman, R. R. Bellamy, P. H. Atkinson, J. Virol. 48, 335 (1983).

H. Holzel, D. W. Cubitt, D. A. McSwiggan, P. J. Sanderson, J. Church, J. Infect. Dis. 2, 33 (1980).

H. Margolit et al., J. Immunol. 138, 2213 (1987).

H. B. Greenberg, H. F. Clark, P. A. Offit, Curr. Top. Microbiol. Immunol. 185, 255.

H. B. Greenberg, H. F. Clark, P. A. Offit, ibid. 185, 255 (1994).

Horie, Y., Nakagomi, O., Koshimura, Y., Nakagomi, T., Suzuki, Y., Oka, T., Sasaki, S., Matsuda, Y., and Watanabe, S. 1999. *Virology* 262:398–407.

J. Collins, et al., J. Pediatr. Gastroenterol. Nutr. 7, 264 (1988).

J. Halvorsrud and I. Orstavik, Scand. J. Infect. Dis. 12, 161 (1980).

J. Levin and F. B. Bang, Throm. Diath. Haemorrh. 19, 186 (1968);

J. Yao, et al., J. Mol. Biol. 243, 736 (1994).

J. L. Wolf, G. Cukor, N. R. Ballcklow, R. Dambrauskas, J. S. Trier, Infec. Immun. 33, 565 (1981).

J. L. Wolf, G. Cukor, N. R. Ballcklow, R. Dambrauskas, J. S. Trier, Infec. Immun. 33, 565 (1981)

J. M. Ball, N. L. Henry, R. C. Montelaro, J. J. Newman, J. Immunol Methods 171, 37 (1994).

J. M. R. Parker, D.Guo, R. S. Hodges, Biochemistry 25, 5425 (1986).

J. P. McAdaragh et al., ibid 41, 1572 (1980);

J. W. Burns, et al., Virol. 207, 143 (1995).

Johansen, K., Hinkula, J., Espinoza, F., Levi, M., Zeng, C. Q. Y., Ruden, U., Vesikari, T., Estes, M. K., and Svensson, L. 1999. *J Med. Virol.* 59:369–377.

K. W. Theil, E. Bohl, R. Cross, E. Kohler, A. Agnes, Am. J. Vet. Res. 39, 213 (1978);

Kapikian, A. Z., and Chanock, R. M. 1996. Rotavirus. In *Virology* $3^{rd}$ ed. B. N. Fields, D. M. Knipe, editors. Raven Press, New York. 1657–1708.

Kensil, C. R., Patel, U., Lennick, M., and Marciani, D. J. 1991. *J. Immunol.* 146:431–437.

Kirkwood, C. D., and Palombo, E. A. 1997. *Virology* 236:258–265.

L. A. Carpino and G.H. Han, J. Org. Chem. 37, 5748 (1970).

L. J. Saif, L. A. Ward, L. Yuan, B. I. Rosen, T. L. To, in Proceedings of the Sapparo International Symposiums on Viral Gastroentritis, S. Chiba, S. Nakata, and M. K. Estes, Eds. (Arch. of Virol. Special Issue) in press; C. A. Mebus, Am. J. Dig. Dis. 21, 592 (1976).

L. M. Little and J. A. Shadduck, Infect. Immun. 38, 755 (1982);

L. R. Forte, et al., Am. J. Phys. 263, C607 (1992).

M. Field, L. H. Graf, W. J. Larid, P. L. Smith, Proc. Natl. Acad. Science USA 75, 2800 1978);

M. G. Currie et al., Proc. Natl. Acad. Science USA 89, 947 (1992);

M. K. Estes, E. L. Palmer, J. F. Obijeski, Curr. Top. Microbiol. Immunol. 105, 123 (1983);

M. N. Burges, et al., Infect. Immunol. 221, 526 (1978);

M. P. Osborne et al., J. Pediatr. Gastroenterol. Nutr. 7, 236 (1988).

Matsui, S. M., Offit, P. A., Vo, P. T., Mackow, E. R., Benfield, D. A., Shaw, R. D., Padilla-Noriega, L., and Greenberg, H. B. 1989. *J. Clin. Microbiol.* 27:780–782.

Meyer, J. C., Bergmann, C. C., and Bellamy, A. R. 1989.

Morris, A. P., Scott, J. K., Ball, J. M., Zeng, C. Q. Y., O'Neal, W. K., and Estes, M. K. 1999. *Am. J. Physiol.*; GI 277:G431–G444.

N. Feng, H. W. Burns, L. Bracy, H. B. Greenberg, J. Virol. 68, 7766 (1994);

O'Neal, C. M., Crawford, S. E., Estes, M. K., and Conner, M. E. 1997. *J. Virol.* 71:8707–8717.

Offit, P. A., and Clark, H. F. 1985. *J. Infect. Dis.* 152:1152–1158.

Offit, P. A., and Clark, H. F. 1985. *J. Virol.* 54:58–64.

P. Tian, M. K. Estes, Y. Hu., J. M. Ball, C. Q.-Y. Zeng, W. P. Schilling, J. Virol. 69, 576 (1995).

P. Tian, Y. Hu, W. P. Schilling, D. A. Lindsay, J. Eiden, M. K. Estes, J. Virol. 68, 51 (1994).

P. E. Wright, et al., Biochemistry 27, 7167 (1988).

P. Y. Chou and G. D. Fassman, Adv. in Enz. 47, 45 (1978).

Prasad, B. V. V., and Estes, M. K. 1997. In W. Chiu, R. M. Burnett, and R. L. Garcea (ed.), Structural Biology of Viruses. Oxford University Press, New York, Oxford. p 239–238.

Prasad, B. V. V., Rothnagel, R., Zeng, C. Q. Y., Jakana, J., Lawton, J. A., Chiu, W., and Estes, M. K. 1996. *Nature* (*London*) 382:471–473.

R. A. Giannella, Ann. Rev. Med. 32, 341 (1981);

R. A. Giannella, M. Luttrell, M. Thompson, Am. J. Phys. 245, G492 (1983);

R. F. Ramig, Microbial Pathogenesis 4, 189 (1988).

R. L. Ward, M. M. McNeal, J. F. Sheridan, J. Virol. 64, 5070 (1990);

Ramig, R. F., 1988. *Microb. Pathog.* 4:189–202.

Reichlin, Methods in Enzym. 70, 159 (1980).

Riepenhoff-Talty, P. C. Lee, P. J. Carmody, H. J. Barrett, P. L. Ogra, Proc. Soc. Exp. Biol. Med. 170, 146 (1982).

Riepenhoff-Talty, P. C. Lee, P. J. Carmody, H. J. Barrett, P. L. Ogra, Proc. Soc. Exp. Biol. Med. 170, 146 (1982).

Ryan, E. T., Butterton, J. R., Smith, R. N., Carroll, P. A., Crean, T. I., and Calderwood, S. B. 1997. *Infect. Immun.* 65:2941–2949.

T. J. Novitsky, Oceanus 27, 13 (1984).

Tian, P., Ball, J. M., Zeng, C. Q. Y., and Estes, M. K. 1996. *J. Virol.* 70:6973–6981.

Tian, P., Estes, M. K., Hu, Y., Ball, J. M., Zeng, C. Q. Y., and Schilling, W. P. 1995. *J. Virol.* 69:5763–5772.

W. G. Starkey et al., J. Gen. Virol. 67, 2625 (1986).

W. J. Krause, R. H. Freeman, L. R. Forte, Cell and Tissue Res. 260, 387 (1990).

Waltho, et al., Biochemistry, 32, 6337 (1993).

Woody, M. A., Krakauer, T., and Stiles, B. G. 1997. *Vaccine* 15:133–139.

X. Jiang, D.Y. Graham, P. Madore, T. Tanaka, M. K. Estes, Science 250, 1580 (1990).

Zent, C. Q. Y., Wentz, M. J., Cohen, J., Estes, M. K., and Ramig, R. F. 1996. *J. Virol.* 70:2736–2742.

Zhang, M. D., Zeng, C. Q. Y., Morris, A. P., and Estes, M. K. 2000. A functional NSP4 enterotoxin peptide secreted from rotavirus-infected cells. Submitted for publication.

Zhang, M., Zeng, C. Q. Y., Dong, Y., Ball, J. M., Sarif, L. J., Morris, A. P., and Estes, M. K. 1998. *J. Virol.* 72:3666–3672.

One of skill in the art readily appreciates that the present invention is well adapted to carry out the objectives and obtain the ends and advantages mentioned as well as those inherent therein. Vaccines, vectors, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of immunization against rotavirus infection or disease comprising administering to a subject a peptide NSP4 112–175.

2. A method of immunization against rotavirus infection or disease comprising administering to a subject a peptide NSP4 112–150.

3. The method of claim 1 or 2, wherein said immunization results in both homotypic and heterotypic immunity.

4. The method of claim 1, wherein said peptide has been chemically treated with glutaraldehyde or formaldehyde.

5. The method of claim 1, wherein said peptide has been heat-inactivated.

6. The method of claim 2, wherein said peptide has been chemically treated with glutaraldehyde or formaldehyde.

7. The method of claim 2, wherein said peptide has been heat-inactivated.

8. A method of passive immunization against rotavirus infection comprising administering to an expectant mother a peptide NSP4 112–175.

9. A method of passive immunization against rotavirus infection comprising administering to an expectant mother a peptide NSP4 112–150.

* * * * *

SEQUENCE LISTING

```
<160> NUMBER OF SEQ ID NOS:   39

<210> SEQ ID NO 1
<211> LENGTH: 22
<212> TYPE: PRT
<213> ORGANISM: Rotavirus NSP4 114-135

<400> SEQUENCE: 1

Asp Lys Leu Thr Thr Arg Glu Ile Glu Gln Val Glu Leu Leu Lys Arg
1               5                   10                  15

Ile Tyr Asp Lys Leu Thr
            20

<210> SEQ ID NO 2
<211> LENGTH: 21
<212> TYPE: PRT
<213> ORGANISM: Rotavirus NSP4 2-22

<400> SEQUENCE: 2

Glu Lys Leu Thr Asp Leu Asn Tyr Thr Leu Ser Val Ile Thr Leu Met
1               5                   10                  15

Asn Asn Thr Leu His
            20

<210> SEQ ID NO 3
<211> LENGTH: 33
<212> TYPE: PRT
<213> ORGANISM: Rotavirus NSP4 90-123
```

-continued

```
<400> SEQUENCE: 3

Thr Lys Asp Glu Ile Glu Lys Gln Met Asp Arg Val Val Lys Glu Met
1               5                   10                  15

Arg Arg Gln Leu Glu Met Ile Asp Lys Leu Thr Thr Arg Glu Ile Glu
            20                  25                  30

Gln

<210> SEQ ID NO 4
<211> LENGTH: 22
<212> TYPE: PRT
<213> ORGANISM: Mutated Rotavirus NSP4 114-135 Peptide

<400> SEQUENCE: 4

Asp Lys Leu Thr Thr Arg Glu Ile Glu Gln Val Glu Leu Leu Lys Arg
1               5                   10                  15

Ile Lys Asp Lys Leu Thr
            20

<210> SEQ ID NO 5
<211> LENGTH: 20
<212> TYPE: PRT
<213> ORGANISM: Rotavirus NV 464-483

<400> SEQUENCE: 5

Asp Thr Gly Arg Asn Leu Gly Glu Phe Lys Ala Tyr Pro Asp Gly Phe
1               5                   10                  15

Leu Thr Cys Val
            20

<210> SEQ ID NO 6
<211> LENGTH: 28
<212> TYPE: PRT
<213> ORGANISM: Rotavirus NSP4 120-147

<400> SEQUENCE: 6

Glu Ile Glu Gln Val Glu Leu Leu Lys Arg Ile Tyr Asp Lys Leu Thr
1               5                   10                  15

Val Gln Thr Thr Gly Glu Ile Asp Met Thr Lys Glu
            20                  25

<210> SEQ ID NO 7
<211> LENGTH: 175
<212> TYPE: PRT
<213> ORGANISM: Porcine Rotavirus

<400> SEQUENCE: 7

Met Ala Leu Leu Ala Ala Leu Ala Thr Thr Leu Ser Val Ile Thr Leu
1               5                   10                  15

Met Ala Ala Thr Leu His Ser Ile Ile Gly Ala Pro Gly Met Ala Thr
            20                  25                  30

Pro Pro Thr Ile Ala Ser Val Leu Thr Val Leu Pro Thr Leu His Leu
            35                  40                  45

Ala Ser Ile Pro Thr Met Leu Ile Ala Leu Leu Thr Ser Leu Cys Ser
        50                  55                  60

Thr Leu Val Ile Leu Thr Cys Met Val Thr Ile Ile Ala Thr Leu Leu
65                  70                  75                  80

Leu Leu Ala Gly Thr Leu Gly Gly Val Thr Thr Leu Ala Gly Ile Gly
                85                  90                  95

Gly Gly Met Ala Ala Ile Ile Leu Gly Met Ala Ala Gly Leu Gly Met
```

-continued

```
                    100                 105                 110
Ile Ala Leu Leu Thr Thr Ala Gly Ile Gly Gly Val Gly Leu Leu Leu
            115                 120                 125
Ala Ile His Ala Leu Leu Ala Ala Pro Val Ala Ile Ala Met
        130                 135                 140
Ser Leu Gly Pro Ala Gly Leu Ala Ile Ala Thr Leu Ala Gly Thr Gly
145                 150                 155                 160
Ser Gly Leu Ala Pro Thr Gly Pro Ser Gly Val Thr Ala Ser Met
                165                 170                 175

<210> SEQ ID NO 8
<211> LENGTH: 175
<212> TYPE: PRT
<213> ORGANISM: OSU-a

<400> SEQUENCE: 8

Met Asp Lys Leu Ala Asp Leu Asn Tyr Thr Leu Ser Val Ile Thr Leu
1               5                   10                  15
Met Asn Asp Thr Leu His Ser Ile Ile Gln Asp Pro Gly Met Ala Tyr
            20                  25                  30
Phe Pro Tyr Ile Ala Ser Val Leu Thr Val Leu Phe Thr Leu His Lys
        35                  40                  45
Ala Ser Ile Pro Thr Met Lys Ile Ala Leu Lys Thr Ser Lys Cys Ser
    50                  55                  60
Tyr Lys Val Ile Lys Tyr Cys Met Val Thr Ile Ile Asn Thr Leu Leu
65                  70                  75                  80
Lys Leu Ala Gly Tyr Lys Glu Gln Val Thr Thr Lys Asp Glu Ile Glu
                85                  90                  95
Gln Gln Met Asp Arg Ile Ile Lys Glu Met Arg Arg Gln Leu Glu Met
            100                 105                 110
Ile Asp Lys Leu Thr Thr Arg Glu Ile Glu Gln Val Glu Leu Leu Lys
        115                 120                 125
Arg Ile His Asp Lys Leu Ala Ala Arg Ser Val Asp Ala Ile Asp Met
    130                 135                 140
Ser Lys Glu Phe Asn Gln Lys Asn Ile Arg Thr Leu Asp Glu Trp Glu
145                 150                 155                 160
Ser Gly Lys Asn Pro Tyr Glu Pro Ser Glu Val Thr Ala Ser Met
                165                 170                 175

<210> SEQ ID NO 9
<211> LENGTH: 63
<212> TYPE: PRT
<213> ORGANISM: Rotavirus NSP4 112-175

<400> SEQUENCE: 9

Met Ile Asp Lys Leu Thr Thr Arg Glu Ile Glu Gln Val Glu Leu Leu
1               5                   10                  15
Lys Arg Ile Tyr Asp Lys Leu Thr Val Gln Thr Thr Gly Glu Ile Asp
            20                  25                  30
Met Thr Lys Glu Ile Asn Gln Lys Asn Val Arg Thr Leu Glu Glu Trp
        35                  40                  45
Glu Ser Gly Lys Asn Pro Glu Pro Lys Glu Val Thr Ala Ala Met
    50                  55                  60

SEQ ID NO 10
<211> LENGTH: 39
<212> TYPE: PRT
```

<213> ORGANISM: Rotavirus NSP4 112-150

<400> SEQUENCE: 10

Met Ile Asp Lys Leu Thr Thr Arg Glu Ile Glu Gln Val Glu Leu Leu
1               5                   10                  15

Lys Arg Ile Tyr Asp Lys Leu Thr Val Gln Thr Thr Gly Glu Ile Asp
                20                  25                  30

Met Thr Lys Glu Ile Asn Gln
                35

<210> SEQ ID NO 11
<211> LENGTH: 175
<212> TYPE: PRT
<213> ORGANISM: Simian 11 Rotavirus (strain SA11)

<400> SEQUENCE: 11

Met Gly Leu Leu Thr Ala Leu Ala Thr Thr Leu Ser Val Ile Thr Leu
1               5                   10                  15

Met Ala Ala Thr Leu His Thr Ile Leu Gly Ala Pro Gly Met Ala Thr
                20                  25                  30

Pro Pro Thr Ile Ala Ser Val Leu Thr Val Leu Pro Ala Leu His Leu
                35                  40                  45

Ala Ser Ile Pro Thr Met Leu Ile Ala Leu Leu Thr Ser Leu Cys Ser
        50                  55                  60

Thr Leu Val Val Leu Thr Cys Ile Val Thr Ile Pro Ala Thr Leu Leu
65                  70                  75                  80

Leu Leu Ala Gly Thr Leu Gly Gly Ile Thr Thr Leu Ala Gly Ile Gly
                85                  90                  95

Leu Gly Met Ala Ala Val Val Leu Gly Met Ala Ala Gly Leu Gly Met
                100                 105                 110

Ile Ala Leu Leu Thr Thr Ala Gly Ile Gly Gly Val Gly Leu Leu Leu
                115                 120                 125

Ala Ile Thr Ala Leu Leu Thr Val Gly Thr Thr Gly Gly Ile Ala Met
            130                 135                 140

Thr Leu Gly Ile Ala Gly Leu Ala Val Ala Thr Leu Gly Gly Thr Gly
145                 150                 155                 160

Ser Gly Leu Ala Pro Thr Gly Pro Ala Gly Val Thr Ala Ala Met
                165                 170                 175

<210> SEQ ID NO 12
<211> LENGTH: 176
<212> TYPE: PRT
<213> ORGANISM: Rotavirus NSP4 SA 11 clone 3

<400> SEQUENCE: 12

Met Glu Lys Leu Thr Asp Leu Asn Tyr Thr Leu Ser Val Ile Thr Leu
1               5                   10                  15

Met Asn Asn Thr Leu His Thr Ile Leu Glu Asp Pro Gly Met Ala Tyr
                20                  25                  30

Phe Pro Tyr Ile Ala Ser Val Leu Thr Val Leu Phe Ala Leu His Lys
                35                  40                  45

Ala Ser Ile Pro Thr Met Lys Ile Ala Leu Lys Thr Ser Lys Cys Ser
        50                  55                  60

Tyr Lys Gly Val Val Lys Tyr Cys Ile Val Thr Ile Phe Asn Thr Leu
65                  70                  75                  80

Leu Lys Leu Ala Gly Tyr Lys Glu Gln Ile Thr Thr Lys Asp Glu Ile
                85                  90                  95

```
Glu Lys Gln Met Asp Arg Val Lys Glu Met Arg Gln Leu Glu
            100                 105                 110
Met Ile Asp Lys Leu Thr Thr Arg Glu Ile Glu Gln Val Glu Leu Leu
            115                 120                 125
Lys Arg Ile Tyr Asp Lys Leu Thr Val Gln Thr Thr Gly Glu Ile Asp
            130                 135                 140
Met Thr Lys Glu Ile Asn Gln Lys Asn Val Arg Thr Leu Glu Glu Trp
145                 150                 155                 160
Glu Ser Gly Lys Asn Pro Tyr Glu Pro Arg Glu Val Thr Ala Ala Met
                165                 170                 175

<210> SEQ ID NO 13
<211> LENGTH: 175
<212> TYPE: PRT
<213> ORGANISM: Rotavirus

<400> SEQUENCE: 13

Met Glu Lys Leu Ala Asp Leu Asn Tyr Thr Leu Gly Val Ile Thr Leu
1               5                   10                  15
Met Asn Asp Thr Leu His Asn Ile Leu Glu Glu Pro Gly Met Val Tyr
                20                  25                  30
Phe Pro Tyr Ile Ala Ser Ala Leu Thr Val Leu Phe Thr Met His Lys
            35                  40                  45
Ala Ser Leu Pro Ala Met Lys Leu Ala Met Arg Thr Ser Gln Cys Ser
    50                  55                  60
Tyr Arg Ile Ile Lys Arg Val Val Thr Leu Val Asn Thr Leu Leu
65                  70                  75                  80
Arg Leu Gly Gly Tyr Asn Asp Tyr Leu Thr Asp Lys Asp Glu Thr Glu
                85                  90                  95
Lys Gln Ile Asn Arg Val Val Lys Glu Leu Arg Gln Gln Leu Ala Met
            100                 105                 110
Ile Glu Lys Leu Thr Thr Arg Glu Ile Glu Gln Val Glu Leu Leu Lys
            115                 120                 125
Arg Ile Tyr Asp Met Met Val Val Cys Arg Asp Arg Glu Ile Asp Met
            130                 135                 140
Ser Lys Glu Thr Asn Arg Lys Ala Phe Lys Thr Leu His Asp Trp Gly
145                 150                 155                 160
Ser Asp Arg Asn Tyr Asp Asp Asn Thr Asp Val Ile Ala Pro Leu
                165                 170                 175

<210> SEQ ID NO 14
<211> LENGTH: 175
<212> TYPE: PRT
<213> ORGANISM: GOTT-V

<400> SEQUENCE: 14

Met Asp Lys Leu Ala Asp Leu Asn Tyr Thr Leu Asn Val Ile Thr Leu
1               5                   10                  15
Met Asn Asp Thr Leu His Ser Ile Ile Gln Asp Pro Gly Met Ala Tyr
                20                  25                  30
Phe Pro Tyr Ile Ala Ser Val Leu Thr Val Leu Phe Thr Leu His Lys
            35                  40                  45
Ala Ser Ile Pro Thr Met Lys Ile Ala Leu Lys Thr Ser Lys Cys Ser
    50                  55                  60
Tyr Lys Val Ile Lys Tyr Cys Met Val Thr Ile Ile Asn Thr Leu Leu
65                  70                  75                  80
```

Lys Leu Ala Gly Tyr Lys Glu Gln Val Thr Thr Lys Asp Gly Ile Glu
                85                  90                  95

Gln Gln Met Asp Arg Ile Ile Lys Glu Met Arg Arg Gln Leu Glu Met
            100                 105                 110

Ile Asp Lys Leu Thr Thr Arg Glu Ile Glu Gln Val Glu Leu Leu Lys
            115                 120                 125

Arg Ile His Asp Lys Leu Val Ala Arg Pro Val Asp Ala Ile Asp Met
            130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175

<210> SEQ ID NO 15
<211> LENGTH: 175
<212> TYPE: PRT
<213> ORGANISM: GOTT-A

<400> SEQUENCE: 15

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Ile Lys Tyr Cys Met Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Ile Lys Glu Met Arg Arg Gln Leu Glu Met
            100                 105                 110

Ile Asp Lys Leu Thr Thr Arg Glu Ile Glu Gln Val Glu Leu Leu Lys
            115                 120                 125

Arg Ile His Asp Lys Leu Ala Ala Arg Ser Val Asp Ala Ile Asp Met
            130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175

<210> SEQ ID NO 16
<211> LENGTH: 751
<212> TYPE: DNA
<213> ORGANISM: Rotavirus NSP4 SA 11 clone 3

<400> SEQUENCE: 16
ggcttttaaa agttctgttc cgagagagcg cgtgcggaaa gatggaaaag cttaccgacc      60
tcaattatac attgagtgta atcactctaa tgaacaatac attgcacaca atacttgagg    120
atccaggaat ggcgtatttt ccttatatag catctgtctt aacagttttg tttgcgctac    180
ataaagcatc cattccaaca atgaaaattg cattgaaaac gtcaaaatgt tcatataaag    240
tggtgaaata ttgtattgta acaattttta atacgttgtt aaaattggca ggttataaag    300
agcagataac tactaaagat gagatagaaa agcaaatgga cagagtagtc aaagaaatga    360

```
gacgccagct agaaatgatt gacaaattga ctacacgtga aattgaacaa gtagagttgc      420
ttaaacgcat ttacgataaa ttgacggtgc aaacgacagg cgaaatagat atgacaaaag      480
agatcaatca aaaaaacgtg agaacgctag aagaatggga agtggaaaaa aatccttatg      540
aaccaagaga agtgactgca gcaatgtaag aggttgagct gccgtcgact gtcctcggaa      600
gcggcggagt tctttacagt aagcaccatc ggacctgatg gctgactgag aagccacagt      660
cagccatatc gcgtgtggct caagccttaa tcccgtttaa ccaatccggt cagcaccgga      720
cgttaatgga aggaacggtc ttaatgtgac c                                     751

<210> SEQ ID NO 17
<211> LENGTH: 751
<212> TYPE: DNA
<213> ORGANISM: Rotavirus Strain ALA

<400> SEQUENCE: 17
ggcttttaaa agttctgttc cgagagagcg cgtgcggaaa gatggataaa cttaccgacc       60
tcaattacac attgagcgta atcactttaa tgaatagtac attgcatgca atattggaag      120
atccagggat ggcgtatttc ccatacatag catctgtgtt gactgttctg ttcactttac      180
ataaagcatc aattccaaca atgaaaattg cgttaaaaac atctagatgt tcctacaaag      240
ttattaaata ttgcattgta accatatttta atacattgtt gaaattagct ggatataaag      300
aacaaataac tactaaagat gaaattgaaa aacagatgga tagagtaatc agagaaatga      360
gacgtcagtt ggaaatgatt gataaattga caactcgtga aattgaacag gtagaactac      420
taagacgtat atatgacaga ttaacggtac gaaagactga tgagatagat atgtcgaagg      480
agatcaatca gaaaaatata cgaacgctag atgaatggga gatggaaaaa aatccatatg      540
aaccaagcga agtgaccgca tcattgtgag aggttggact gccgtcgact gtctctggaa      600
gcggcggagt ccttcacagt aagtcccatc ggacctgatg actggctgag aagccacagt      660
cagtcatatc gcgtgtggct caagccttaa tcccgtttaa ccaatccggt gagcgccgga      720
cgttaatgga aggaatggtc ttagtgtgac c                                     751

<210> SEQ ID NO 18
<211> LENGTH: 751
<212> TYPE: DNA
<213> ORGANISM: Lapine Rotavirus Strain C-11

<400> SEQUENCE: 18
ggcttttaaa agttctgttc cgagagagcg cgtgcggaaa gatggataaa cttaccgacc       60
tcaattacac attgagcgtg atcactttaa tgaatagtac attgcataca atattggaag      120
atccagggat ggcgtatttc ccatacatag catctgtgtt gactgttctg ttcactttgc      180
ataaagcatc aattccaaca atgaaaattg cgttaaaaac atctagctgt tcctacaaag      240
ttattaaata ttgtcttgtt actatattta atacattgcc taaattagct ggatataaag      300
aacaaataac tactaaacgt gaaattgaaa aacagatgga tagagttatc agagaaatga      360
gacgtcagtt agaaatgatt gataaattga caactcgtga aattgaacag gtagaactac      420
taagacgtat atatgacaaa ttaacggtac gaaagactga tgataggt atgttgaagg      480 agatcaatca gaaaaatata cggacgctag atgaatggga gatggaaag aatccatacg      540 aaccaagcaa agtgaccgca tcattgtgag aggttggact gccgtcgact gtcctggaag      600
cggcggagtc cttcacagta agtcccatcg gacctgatga ctggctgaga agccacagtc      660
```

-continued

| atatcatatc gcgtgtggct caagccttaa tcccgtttaa ccaatccggt gagcgccgga | 720 |
| cgttaatgga aggaatggtc ttagtgtgac c | 751 |

<210> SEQ ID NO 19
<211> LENGTH: 751
<212> TYPE: DNA
<213> ORGANISM: Lapine Rotavirus Strain R-2

<400> SEQUENCE: 19

| ggcttttaaa agttctgttc cgagagagcg cgtgcggaaa gatggaaaag cttaccgacc | 60 |
| tcaactatac attgaatgtg atcactttat tgaacagtac attgcataca atattggagg | 120 |
| atccagggat ggcgtacttt ccttacattg catctgtcct aacagtttta ttcacattac | 180 |
| acaaagcgtc gattccaacg atgaaaattg ccttaagaac atcaaaatgt tcctataaag | 240 |
| tgataaagta ttgtattgta acaattttca atacgctact aaagttagcc ggctataaag | 300 |
| aacagattac tactaaagaa tggattgaaa acagttggac aaagtaata aaagaaatga | 360 |
| gacgtcagct agaaatgata gataaattga caactcgaga aattgaacag gtagagctac | 420 |
| taaaacgtat atacgacaaa ctaatgatac gaaagactga tgaaatagat atgacgaagg | 480 |
| agatcaatca aaaaaatgta aaaacgctag atgaatggga gatgggaag aatccatatg | 540 |
| aatcaaaaga agtgactgca gcaatgtaag aggttgggct gccgtcgact gtcttcggaa | 600 |
| gcggcggagt tcttcacagt aagttccatc ggacctgatg agtggctgag aagccacagt | 660 |
| cagtcatatc gcgtgtggct caagccttaa tcccgtttaa ccaatccggt gagcgccgga | 720 |
| cgttaatgga aggaagggtc ttagtgtgac c | 751 |

<210> SEQ ID NO 20
<211> LENGTH: 751
<212> TYPE: DNA
<213> ORGANISM: Lapine Rotavirus Strain BAP-2

<400> SEQUENCE: 20

| ggcttttaaa agttctgttc cgagagagcg cgtgcggaaa gatggataaa cttaccgacc | 60 |
| tcaattacac attgagcgta atcactttaa tgaatagtac attgcatgca atattggaag | 120 |
| atccagggat ggcgtatttc ccatacatag catctgtgtt gactgtactg ttcacttttac | 180 |
| ataaagcatc aattccaaca atgaaaattg cgttaaaaac atctagatgt tcctacaaag | 240 |
| ttattaaata ttgcattgta accatatttta atacattgtt gaaattagct ggatataaag | 300 |
| aacaaataac tactaaagat gaaattgaaa gacagatgga cagagtagtc cgagaaatga | 360 |
| gacgtcagtt ggaaatgatt gataaattga caacacgtga aattgaacag gtagaactac | 420 |
| taagacgtat atacgacaga ctaacggtgc gaaagactga tgagatagat atgtcgaagg | 480 |
| agatcaatca gaaaaatata cggacgttag atgaatggga gatggaaaaa aatccatatg | 540 |
| aaccaagcga ggtgaccgca tcattgtgag aggttggact gccgtcgact gtccctggaa | 600 |
| gcggcggagt cctttacagt aagtcccatc ggacctgatg actggctgag aagccacagt | 660 |
| cagtcatatc gcgtgtggct caagccttaa tcccgcttaa ccaatccggt gagcgccgga | 720 |
| cgttaatgga aggaatggtc ttagtgtgac c | 751 |

<210> SEQ ID NO 21
<211> LENGTH: 751
<212> TYPE: DNA
<213> ORGANISM: Lapine Rotavirus Strain BAP (wildtype)

<400> SEQUENCE: 21

```
ggcttttaaa agttctgttc cgagagagcg cgtgcggaaa gatggataaa cttaccgacc    60
tcaattacac attgagcgta atcactttaa tgaatagtac attgcatgca atattggaag   120
atccagggat ggcgtatttc ccatacatag catctgtgtt gactgtactg ttcactttac   180
ataaagcatc aattccaaca atgaaaattg cgttaaaaac atctagatgt tcctacaaag   240
ttattaaata ttgcattgta accatattta atacattgtt gaaattagct ggatataaag   300
aacaaataac tactaaagat gaaattgaaa gcagatggga cagagtaatc cgagaaatga   360
gacgtcagtt ggaaatgatt gataaattga caactcgtga aattgaacag gtagaactac   420
taagaagaat atacgacaga ctaacggtac gtaagactga tgagatagat atgtcgaagg   480
aaatcaatca gaaaaatata cggacgttag atgaatggga aatgaaaaa atccatatg    540 aaccaagcga ggtgaccgca tcattgtgag aggttggact gccgtcgact gtccctggaa   600
gcggcggagt ccttcacagt aagtcccatc ggacctgatg actggctgag aagccacagt   660
cagtcatatc gcgtgtggct caagccttaa tcccgtttaa ccaatccggt gagcgccgga   720
cgttaatgga aggaatggtc ttagtgtgac c                                   751

<210> SEQ ID NO 22
<211> LENGTH: 750
<212> TYPE: DNA
<213> ORGANISM: Procine Rotavirus Strain A253

<400> SEQUENCE: 22
ggcttttaaa agttctatt cgagagagcg cgtgcggaaa gatggataag cttgcagacc    60
ttaattatac tttgagcgtt atcactttaa tgaatgatac actacactct ataattcaag   120
atccagggat ggcgtacttc ccatatattg catctgtact gactgtatta tttactctac   180
ataaggcatc aattcccaca atgaaaattg cgttaaaaac gtcaaagtgt tcgtacaaag   240
taattaagta ttgcatggtt acaatcatta atactcttct gaagttggct ggttacaagg   300
aacaggttac tactaaggac gaaattgaac aacagatgga tagaattgta aaagagatga   360
gacgtcaact ggaaatgatt gataaattga ctactcgtga aattgaacag gtagaattac   420
ttaaacgtat acacgataaa ttggtagtta gacctgtaga cgttatagac atgtcgaaag   480
aatttaacca gaaaaatatt agaacgctag acgaatggga aagtgggaaa atccatacg    540 aaccctcgga agttactgcg tctatgtgag aggttgagtt gccgtcgtct gtcttcggaa   600
gcggcggaac tcttcaccgc aagccccatt ggacacgatg gtttactgac aaaccccagt   660
caatcatttc gcgtgtagca catccctaat cccgaataac caatccagcg aatgttggac   720
gttaatggaa ggaatggtct taatgtgacc                                    750

<210> SEQ ID NO 23
<211> LENGTH: 750
<212> TYPE: DNA
<213> ORGANISM: Porcine Rotavirus Strain A131

<400> SEQUENCE: 23
ggcttttaaa agttctgttt cgagagagcg cgtgcggaaa gatggataag cttgcagacc    60
ttaattacac tttgagcgtt attactttaa tgaatgacac actacattct attattcaag   120
atccagggat ggcgatcttc ccatatatag catctgtact gactgtatta tttactctac   180
ataaggcatc aatacccaca atgaaaattg cgttaaaaac gtcaaagtgt tcgtataaag   240
taataaagta ctgcattgtt acaattatca atactcttct gaaattggct ggttacaagg   300
```

-continued

```
aacaggttac tacaaaggat gaaattgaac aacagatgga cagaatcatt aaagagatga    360
gacgtcaact ggaaatgata gataagttga ctactcgtga aattgaacag gtagaattac    420
ttaagcgtat tcatgataag ttggttgtaa ggccagtaga cgttattgac atgtcgaaag    480
aatttaatca gaagaatata cgaacgcttg acgaatggga agtggaaaa aatccatacg    540 aaccgtcgga agtaactgca tctatgtgag aggttgagtt accctcgtct gtatttggga    600
gcggcgggac tcttcatcgc aaaccacatt ggacacgatg gtttactgac aaaccccagt    660
caatcatatc gcgtgtagca cagccataat cccgtataac aaatcctgcg aatgttggac    720
gttaatggaa ggaatggtct taatgtgacc                                     750
```

<210> SEQ ID NO 24
<211> LENGTH: 750
<212> TYPE: DNA
<213> ORGANISM: Porcine Rotavirus Strain A411

<400> SEQUENCE: 24

```
ggcttttaaa agttctgttc cgagagagcg cgtgcggaaa gatggataag cttgacgatc     60
ttaattatac tttgagcgtc atcactttaa tgaatgacac actacattct ataattcaag    120
atccaggaat ggcgtacttc ccatacatag catctgtact gactgtttta tttactctac    180
ataaggcatc aattcccaca atgaaaattg cgttaagaac gtcaaagtgt tcgtataaag    240
taataaaata ctgcattgtt acaattttta atactcttct gaaattggct ggttacaaag    300
aacaggttac tactaaagac gaaattgaac aacagatgga cagaattatc aaagagatga    360
gacgtcaact ggaaatgatt gacaaattga ctactcgtga aattgaacag gtagaattac    420
ttaaacgtat tcacgataaa ctggttgcaa ggtcagttga cgttatagac atgtcgaaag    480
aatttaatca gaaaatata agaacgctag atgaatggga agtggaaaa aatccctacg    540 aaccgtcgga agtaactgca tctatgtgag aggttgagtt gccgtcatca gtctttggga    600
gcggcggaac tcttcatcgc aagccccatt ggacccgatg gttgactgag aagccacagt    660
caatcatttc tcgtgtagca cagccctaat cccgattaac caatccagcg aatgttggac    720
gttaatggaa ggaatggtct taatgtgacc                                     750
```

<210> SEQ ID NO 25
<211> LENGTH: 675
<212> TYPE: DNA
<213> ORGANISM: Porcine Rotavirus Strain A34

<400> SEQUENCE: 25

```
gatggataag cttgccgacc tcaactacac attgagtgta atcactttaa tgaatgatac     60
gttacactct attattcaag atccaggaat ggcgtatttt ccatatatcg catctgttct    120
aactgtttta tttactctac ataaagcatc aattccaacg atgaaaatag cattaagaac    180
gtcaaaatgt tcatacaaag taattaaata ttgtatggtt acgatcatta atactcttct    240
aaagttggct ggttataaag aacaggttac taccaaggat gaaatcgaac aacagatgga    300
cagaattgtt aaagagatga gacgtcaact ggagatgatt gacaaattga caactcgtga    360
aattgaacag gtcgaattac ttaagcgtat acatgataaa ttagttacta gaccagttga    420
tgctatagac atgtcgaaag aatttaatca gaagaatatc agaacgctag atgaatggga    480
aagcggaaaa aatccatatg aaccatcaga agtgactgca tctatgtgag aggttgagtt    540
gccgtcgtct gtcttcggaa gcggcggaac tcttcaccgc aagccccatt ggacctgatg    600
gttgactgag aagccacagt caatcatatc gcgtgtggct cagccttaat cccgtttaac    660
```

-continued caatccagcg aatgt 675

<210> SEQ ID NO 26
<211> LENGTH: 751
<212> TYPE: DNA
<213> ORGANISM: Equine Rotavirus Strain H-2

<400> SEQUENCE: 26
ggcttttaaa agttctgttc cgagagagcg cgtgcggaaa gatggataag cttaccgacc 60
tcaactatac attgaatgtg atcactttat tgaacagtac attgcataca atattggagg 120
atccagggat ggcgtacttt ccttacattg catctgtcct aacagtttta ttcacattac 180
acaaagcgtc gattccaacg atgaaaattg ccttaagaac atcaaaatgt tcgtataaag 240
tgataaagta ttgtattgta acaattttca atacgctact aaagttagca ggctataaag 300
aacagattac tactaaagat gaaatagaaa aacaaatgga tagagtagtt aaagaaatga 360
gacgtcattt agagatgatt gataaattga ctacacgtga aattgaacaa gtagaattac 420
ttaaacgtat ttatgataaa ctgatgatac gggcaacaga cgaaatagat atgacgaaag 480
aaatcaatca aaagaacgtg aaaacgctag aagaatggga aaatggaaag aatccttatg 540
aatcaaaaga agtgactgca gcaatgtaag aggttgagct gccgtcgact atcttcggaa 600
gcggcggagt tctttacagt aagctccatc agacctgatg gctggctgag aagccacagt 660
cagccatatc gcgtgtggct caagccttaa tcccgtttaa ccaatccggt cagtaccgga 720
cgttaatgga aggagtggtc ttagtgtgaa g 751

<210> SEQ ID NO 27
<211> LENGTH: 751
<212> TYPE: DNA
<213> ORGANISM: Equine Rotavirus Strain FI-23

<400> SEQUENCE: 27
ggcttttaaa agttctgttc cgagagagcg cgtgcggaaa gatggataag cttaccgacc 60
ttaattatac attgaatgta attactctat tgaacagtac attgcataca attttagagg 120
atccagggat ggcgtatttc ccttacattg catctgtact aacagtatta ttcacattac 180
acaaagcgtc gattccaacg atgaagattg ccttaagaac atcaaaatgt tcgtacaagg 240
tgattaagta ttgtatagtt acaattttca atacgctact aaagttagca ggctataagg 300
aacagattac tactaaggac gaaatagaaa aacaaatgga tagagttgtt aaagaaatga 360
ggcgtcacct agagatgata gataagttga ctacacgtga aatagagcaa gttgaattac 420
ttaaacgtat atacgataag ctgatggcac gagcaacaga tgaaattgat atgactaaag 480
aaataaatca gaagaacgtg aaaacgttag aagaatggga aaatggaaag aatccttacg 540
aatcaaaacg aatgactgca gcaatgtaag aggttgaact gccgtcgact atctttggaa 600
gcgggggggt actatatagt aagctccatc agacctaata gctggctgag aagccacagt 660
cagcaattta aaaagtggct caagccttaa ttcccttcaa ccaatccggt cagtaccgga 720
cgttaatgga aggagtggtc ttagtgtgaa g 751

<210> SEQ ID NO 28
<211> LENGTH: 751
<212> TYPE: DNA
<213> ORGANISM: Equine Rotavirus Strain FI-14

<400> SEQUENCE: 28

```
ggcttttaaa agttctgttc cgagagagcg cgtgcggaaa gatggataaa ctaaccgacc      60
tcaactatac attgaacgta atcactttaa ttaacagcac attgcataca atttagagg      120
atcccggaat ggcgtatttc ccttacattg catctgtatt aacagtatta ttcacattac     180
acaaggcatc gataccaacg atgaagatag ccttgaaaac atcaaagtgt tcgtataaag    240
tagtaaaata ctgtatagtt acaatttta  atacgctact aaaattagca ggctacaaag    300
aacaaataac tactaaagat gaaattgaga agcaaatgga cagagtaatt aaagaaatga    360
gacgtcattt agagatgata gacaagttga caactcgtga gatagagcaa gttgaactac   420
ttaagcgtat atacgataag ctaatgattc gggctacgga cgaaattgat atgtcgaaag   480
aaattaacca aaagaacgta agaacgttag aagaatggga aaacggaaag aatccttatg   540
aatcaaaaga gttactgca  gcaatgtaag aggttgagct gccgtcgact atcttcggaa    600
gcggcggagt attttacagt aagctccacc aaacctgatg gctggcagaa aaaccccatt   660
cagcaatttc gcgtgtggct cataacttaa ttccgttcaa tcactccggt cagtaccgga   720
cgttaatgga aggagtggtc ttagtgtgaa g                                   751

<210> SEQ ID NO 29
<211> LENGTH: 751
<212> TYPE: DNA
<213> ORGANISM: Bovine Rotavirus Strain BRV033

<400> SEQUENCE: 29
ggctttaaaa agttctgttc cgagagagtg tgtgcgggaa gatggagaag cttaccgacc    60
tcaactacac atcgagtgtt atcactctaa tgaacaacac attgcatacg attcttgagg   120
accccggaat ggcgtacttc ccatacattg catctgtcct aacagttttg tttacgttgc   180
acaaggcatc tatacctaca atgaagatag cactgaaaac gtccaagtgt tcatacaaag  240
tagtaaaata ctgtatagta acgatattca atacgttgtt gaaattggca ggttacaaag  300
aacagataac tactaaagat gagatagaaa agcaaatgga cagggttgtt aaagagatga  360
gacgtcagtt tgaaatgatt gataagttga ctacacgtga aatagagcag gtagagttgc  420
taaagcgcat acacgacaag ttgatggttc gagcaacaga tgagattgat atgacgaagg  480
aaataaacca aaagaacgta agaacgctag aagaatggga aaatggaaaa aatccttatg  540
aacccaagga ggtgactgca gcgatgtaag aggttgagct gccctcgact gtcttcggaa   600
gcggcggagt tcttcacagt aagccacatc ggacatgatg acttactgaa aagcccagt   660
cagtcatttc ccgagtggct taagccttaa tccccttcaa ccattcaggt cagcaccgga  720
cgttaatgga gggaacggtc ttaatgtgac a                                  751

<210> SEQ ID NO 30
<211> LENGTH: 751
<212> TYPE: DNA
<213> ORGANISM: Bovine Rotavirus Strain B223

<400> SEQUENCE: 30
ggctttaaaa agttctgttc cgagagagtg tgtgcgggaa gatggaaaag ctaaccgacc    60
tcaactatac attgagtgtt atcactctaa tgaactccac attgcatacg attcttgagg   120
accccgggat ggcgtacttc ccatatattg catcagtttt aacagtatta ttcacgttgc   180
acaaggcatc tatacccaca atgaagattg ctctaaagac gtccaagtgt tcatacaaag  240
tagtaaaata ttgcattgtt acgattttca atacgttgtt gaaattggct gggtacaaag  300
aacagataac tactaaagat gagatagaga acagatgga  aagggtagta aaggaaatga  360
```

```
gacgtcactt caaaatgata gacaaattga caactcgtga aattgagcag gtaggattgc      420
taaagcgcat tcacgacaag ttggatatac gggctgttga tgaaatagac atgacgaaag      480
aaattaacca gaaaaacgtt agaacgctag aagaatggga gtgggaaaa aatccctatg       540 aacccaaaga agttactgct gcaatgtaag aggttgagct accttcgaca gtattcggaa      600 gcggggggt actacacagt aagcctcaac ggttatgttg actaactgag aaacctcaat       660
cagtcatttc cagagttttt taagccttaa tccccttcaa ccattcaggt cagcaccgga      720
cgttaatgga aggaacggtc ttaatgtgac a                                    751

<210> SEQ ID NO 31
<211> LENGTH: 750
<212> TYPE: DNA
<213> ORGANISM: Canine Rotavirus Strain CU-1

<400> SEQUENCE: 31
ggcttttaaa agttctgttc cgagaaagcg catgcggaaa gatggagaag cttgcagacc       60
tcaactatac cctgagtgta atcacgctaa tgatgatac tttgcacact attatggagg       120
atcccggaat ggcatacttc ccatatattg catctgttct aactgtacta tttacattac      180
ataaggcatc aatcccaacc atgaaaatcg cacttaaaac atcaagatgt tcatacaagg      240
ttatcaagta ctgcatagta tcagtattta acactctatt gaagttggct ggatacaaag      300
agcagataac tactaaagat gaaatagaaa acaaatgga cagagttgtt aaagaaatga       360
ggcgtcagct ggaaatgatt gataaactaa ccacaaggga gatagaacag gttgaacttc      420
ttaaacgaat acacgatatg ttaattgcaa agcccgtaga caagatagat atgtcgcaag      480
agttcaacca aaagcatttc aaaacactaa acgagtgggc agagggtgaa aatccatacg      540
aaccgagaga agtaactgca tctttatgag aggttgaact gccgtcttcg gtatgcggga      600
gcggaggagt aataaacaga aaatctcatc gaacttgatg aatggtagag aaacctcatt      660
cagtaatttc gcgggtgact tagtcttatt cacgttttac cattccagcc agtgctggac      720
gttaatggaa ggaatggtct taatgtgacc                                      750

<210> SEQ ID NO 32
<211> LENGTH: 750
<212> TYPE: DNA
<213> ORGANISM: Porcine Rotavirus A

<400> SEQUENCE: 32
ggcttttaaa agttctgttc cgagagagcg cgtgcggaaa gatggataag cttgccgacc       60
tcaattacac attgagcgta atcactttaa tgatgacac actacactct attattcaag       120
atccaggaat ggcgtatttt ccatatattg catctgttct gactgttta tttactctac        180 ataaagcatc aattccaaca atgaaaatag cgttaaaaac gtcaaagtgt tcgtacaaag      240
taattaaata ttgcatggtt acaatcatta atactcttct gaagttggct ggttataaag      300
aacaggttac tactaaggat gaaattgaac aacagatgga cagaattatt aaagagatga      360
gacgtcaact ggaaatgatt gacaaattga cgactcgtga aattgaacag gttgaattac      420
ttaaacgtat acatgacaaa ttagctgcta gatcagttga cgctatagat atgtcgaaag      480
aatttaatca gaaaaatatt cgaacgctag atgaatggga aagtggaaaa aatccatatg      540
aaccgtcgga agtaactgcg tctatgtgag aggttgagtt gccgtcgtct gtcttcggaa      600
gcggcggaac tcttcaccgc aagccccatt ggacccgatg gttgactgag aagccacagt      660
```

-continued

| | |
|---|---|
| caatcatatc gcgtgtggct cagccttaat cccgtttaac caatccagcg aatgttggac | 720 |
| gttaatggaa ggaatggtct taatgtgacc | 750 |

<210> SEQ ID NO 33
<211> LENGTH: 528
<212> TYPE: DNA
<213> ORGANISM: Simian 11 Rotavirus (strain SA 11)

<400> SEQUENCE: 33

| | |
|---|---|
| atggaaaagc ttaccgacct caattataca ttgagtgtaa tcactctaat gaacaataca | 60 |
| ttgcacacaa tacttgagga tccaggaatg gcgtattttc cttatatagc atctgtctta | 120 |
| acagttttgt ttgcgctaca taagcatcc attccaacaa tgaaaattgc attgaaaacg | 180 |
| tcaaaatgtt catataaagt ggtgaaatat tgtattgtaa caatttttaa tacgttgtta | 240 |
| aaattggcag gttataaaga gcagataact actaaagatg agatagaaaa gcaaatggac | 300 |
| agagtagtca agaaaatgag acgccagcta gaaatgattg acaaattgac tacacgtgaa | 360 |
| attgaacaag tagagttgct taaacgcatt tacgataaat tgacggtgca aacgacaggc | 420 |
| gaaatagata tgacaaaaga gatcaatcaa aaaaacgtga gaacgctaga agaatgggaa | 480 |
| agtggaaaaa atccttatga accaagagaa gtgactgcag caatgtaa | 528 |

<210> SEQ ID NO 34
<211> LENGTH: 1356
<212> TYPE: DNA
<213> ORGANISM: Rotavirus subgroup 1 (VP6)
<220> FEATURE:
<221> NAME/KEY: misc_feature
<222> LOCATION: (1340)..(1356)
<223> OTHER INFORMATION: unknown

<400> SEQUENCE: 34

| | |
|---|---|
| ggcttttaaa cgaagtcttc aacatggatg tcctgtactc attgtcaaaa actcttaaag | 60 |
| acgccagaga caagatcgtt gaaggcacat tatactccaa tgtaagtgat ctaattcaac | 120 |
| agtttaatca aatgataatt actatgaatg gaaatgaatt tcaaactgga ggaattggca | 180 |
| acttacccat tagaaattgg aattttgatt ttggcctact tggaactact ctactaaact | 240 |
| tagatgctaa ttacgttgaa actgcacgta atacaattga ttattttgtc gattttgtgg | 300 |
| ataatgtatg catggatgag atggttaggg aatcacaaag aaatggaatc gcaccgcaat | 360 |
| cagactcact cagaaaactg tcaggcatta aatttaaaag aataaatttt gacaattcat | 420 |
| cagagtatat tgaaaattgg aatctgcaga atagaagaca gagaacaggt ttcacattcc | 480 |
| acaagccgaa catctttcct tattcagcat catttacact aaaccgatcg caaccagctc | 540 |
| atgataattt aatgggtaca atgtggttaa atgcaggatc agaaattcag gttgctggat | 600 |
| ttgattattc atgtgctatt aacgctccag ctaatacaca acaatttgaa catattgtac | 660 |
| agctccggag agtactaact actgctacga taactctttt accagacgca gaaagattta | 720 |
| gttttccaag agtgattaat tcagctgacg gagcaactac atggtatttt aatccagtga | 780 |
| ttcttaggcc aaataacgtt gaagtagagt ttctgttgaa tgggcaaata ataaacactt | 840 |
| atcaagcaag atttggaaca ataatagcta gaattttga tactattaga ttgtcattcc | 900 |
| agctaatgag accaccaaat atgacaccaa cagtagctgc actattccca aatgcacaac | 960 |
| catttgaaca tcatgctacg gtaggcctaa cactaagaat tgagtctgca gtgtgtgaat | 1020 |
| cagtactagc tgatgcgagc gaaacaatgc tagctaatgt aacgtctgtt aggcaggaat | 1080 |
| acgcaatacc agttggacca gtatttccac caggcatgaa ttggactgat ctaatcacta | 1140 |

```
attactcacc atctagggag gataatttgc agcgtgtgtt tacagtggct tccattagaa    1200
gcatgctaat taaatgagga ccaagctaac tacttggtat ccgaacttta taagcatgta    1260
gctatgtcaa gctatttgaa cttttgtaagt aaggatgtat ttatacattc gctacacaaa    1320
gtaatcactt caatgatgtn nnnnnnnnnn nnnnnn                              1356
```

<210> SEQ ID NO 35
<211> LENGTH: 1356
<212> TYPE: DNA
<213> ORGANISM: Rotavirus subgroup 2

<400> SEQUENCE: 35

```
ggctttaaaa cgaagtcttc gacatggagg ttctgtactc actgtcaaaa actcttaaag      60
atgctaggga caaaattgtt gaaggtacat tatattctaa tgttagcgat cttattcagc     120
aattcaatca aatgatagta actatgaatg gaaatgattt tcagactgga ggaattggta     180
atttacctgt tagaaattgg actttcgatt ttggtctatt aggtacaaca cttttgaact     240
tggatgctaa ttatgttgag aatgcaagaa ctataattga atattttatt gactttattg     300
ataatgtatg tatggatgaa atggcaagag aatctcaaag aaatggagta gcgccacaat     360
ctgaagcgtt gagaaagtta gcgggaatta aatttaagag aataaatttc gataattcat     420
cagaatacat agaaaattgg aacttacaaa atagaagaca gcgcaccgga tttgtttttc     480
ataaacctaa catatttcca tactcagctt catttactct aaatagatct caaccaatgc     540
atgataattt aatgggaacc atgtggctta atgctggatc agaaattcaa gtggctggat     600
ttgactactc atgcgccata aatgcaccag cgaacataca gcaatttgaa catatcgtcc     660
agcttaggcg cgcactgact acagctacta taactttatt acctgatgca gagagattta     720
gttttccaag agtaattaat tcagctgatg gcgcgactac atggttcttt aatccagtta     780
ttctaagacc aaacaatgta gaggtagaat ttttgttgaa tggacaaatt attaatacat     840
atcaggctag atttggtact atcatcgcaa gaaattttga tgcaattcgt ttattatttc     900
agttgatgcg tccacctaat atgacaccag ctgttaatgc actgtttcca caagcacaac     960
cttttcagca ccatgcaaca gttggactta cattacgtat tgaatctgcg gtttgtgaat    1020
cagtgcttgc ggacgcaaat gaaactctgt tagcaaatgt gaccgcggtg cgtcaagaat    1080
atgccatacc agttggaccg gtatttccac caggcatgaa ttggactgaa ttaattacta    1140
actattcgcc atctagagaa gataacttgc aacgcgtttt cacggtagct tccattagaa    1200
gcatgttgat taagtgagga ccagactaag catctggtat ccaatcttag ttagcatgta    1260
gctacatcaa gtcattcaga ctcttcaagt aaggacatga tttcatgttc gctacgtaga    1320
gtaactgtct gaatgatgta gtgagaggat gtgacc                               1356
```

<210> SEQ ID NO 36
<211> LENGTH: 2717
<212> TYPE: DNA
<213> ORGANISM: Bovine rotavirus (VP2)

<400> SEQUENCE: 36

```
ggctattaaa ggctcaatgg cgtacaggaa gcgcggagct aaacgtgaaa acttaccaca      60
acaaaatgaa cgtctgcaag aaaaagaaat tgaaaaagat gtggatgtaa ctatggagaa     120
taaaaataac aatagaaagc agcaattatc tgataaagta ctatcacaaa agaggaaat      180 aataactgat gcacaagatg atattaaaat agctggtgag attaaaaaat catcaaaaga     240
```

-continued

```
agagtcaaaa cagttgctcg aaatattaaa aacgaaagaa gaccatcaga aagaaataca    300
gtatgaaatt ctacaaaaaa cgataccgac ttttgaatca aaagaatcaa ttttgaaaaa    360
attagaagat ataagaccgg agcaagctaa gaagcaaatg aaattgttta gaatatttga    420
accaaaacaa ttaccaatct atcgagcaaa tggtgagaaa gaattgagaa atagatggta    480
ttggaaattg aaaaaggata cgctgccaga tggagattat gatgtacgag aatatttctt    540
aaatttatat gatcagatcc tgatagaaat gccagattat ttgctactga agatatggc    600 tgtagaaaat aaaaactcta gagatgctgg taaagttgta gattctgaaa cggcaaatat    660
ttgtgatgct atatttcaag atgaagagac agagggagtt gtcagaagat tcattgcaga    720
tatgagacaa caggttcagg ctgatagaaa tattgtcaat tatccatcaa ttttacatcc    780
aattgatcac gcatttaatg aatattttct aaatcatcaa ttagtcgaac cactaaataa    840
tgaaatcatt tttaattata taccagaaag aataaggaat gatgttaact atattttgaa    900
tatggatatg aatttgccat caacagcaag atatattaga ccaaatttat gcaagataga    960
actaaattta catgataatt ttgaatcatt atgggacaca ataactacat caattatat   1020 actagccaga tcagttgtgc ctgatttgaa ggaaaaagaa ttagtttcaa ctgaagctca   1080
gatacagaaa atgtctcaag atttgcaact tgaagcttta acgatacaat ctgaaacgca   1140
gtttcttgct ggcataaatt cacaagcagc aaatgattgt tttaaaacat tgatagcagc   1200
tatgttaagc cagcgtacaa tgtcattaga ttttgtaacc acgaattata tgtcacttat   1260
atctggtatg tggctattga ccgttatacc aaatgatatg tttcttcgtg aatcattagt   1320
cgcatgcgaa ttggccataa taaatactat agtttatcca gcatttggaa tgcaaagaat   1380
gcattataga aatggtgatc cccagactcc gtttcaaata gcagaacagc aaatacaaaa   1440
ttttcaagta gctaattggt tacatttat taataataat agatttaggc aagttgttat   1500
tgatggagtg ttaaatcaaa cacttaacga taatattagg aatggacaag ttattaatca   1560
gttaatggaa gcattaatgc agctatctag acaacaattt ccgactatgc cagttgatta   1620
taaaagatca atccaaagag gaatattact attatctaac agattaggtc agttagttga   1680
tttaacaaga ttagtatcat ataattatga aactctaatg gcttgtgtaa ctatgaatat   1740
gcaacatgtt caaactctca ctaccgaaaa attacaatta acttctgtca catctttatg   1800
tatgttaatt ggaaatacta cagtaattcc aagtccacaa acattatttc actattataa   1860
cataaatgta aattttcatt caaattaaa cgaacgaatt aacgacgcag tggctatcat   1920
tacggctgct aatagactaa acttatatca gaaaaaaatg aaatcaatag ttgaggattt   1980
tttgaaaaga ttgcaaattt ttgatgtacc acgagtacca gatgaccaaa tgtacaggtt   2040
gagagataga cttaggttat taccagttga aagacgaaga cttgatatat ttaatttaat   2100
attaatgaat atggagcaga tcgaacgagc ttcagataaa attgctcaag gagtaataat   2160
tgcttataga gatatgcaac tagaaagaga tgagatgtat ggatatgtca acattgctag   2220
aaatctcgat ggatatcaac aaattaacct agaggagttg atgagaactg gagactatgg   2280
gcaaattact aaatatgttat taaacaatca gcctgtagct ttagtagggg cattaccatt   2340
tgtgacggat tcttcagtta tatcactcat tgcaaaatta gatgctacag ttttgctca   2400 aatagttaaa cttagaaaag tggacacttt aaaaccaata ttgtataaga taattctga   2460 ttctaatgat ttctacttag ttgcaaatta tgattggata ccaacttcaa ccacaaaagt   2520
ctataaacaa gtaccacaac cttttgattt cagagcgtca atgcatatgt taacgtctaa   2580
tttgactttt acagtttatt ctgatttatt atctttcgtt tctgcagaca cggttgaacc   2640
```

```
cattaacgca gttgcttttg acaatatgcg cattatgaac gaactgtaaa cgccaacccc    2700
actgtggaga tatgacc                                                   2717

<210> SEQ ID NO 37
<211> LENGTH: 2690
<212> TYPE: DNA
<213> ORGANISM: Simian rotavirus SA11 clone 3 (VP2)

<400> SEQUENCE: 37
ggctattaaa ggctcaatgg cgtatcgaaa acgtggagcg cgtcgtgaga cgaatctaaa      60
acaagatgaa cgaatgcaag aaaaagaaga tagcaagaac attaataatg acagtcctaa     120
atcacaatta tcagaaagag tattatctaa gaaagaagag ataattacag ataatcaaga     180
agaagttaag atatctgatg aggtaaaaaa atctaataaa gaagaatcga aacagttgtt     240
agaagtactt aaaacaaaag aggaacatca aaaagaagtt cagtatgaaa tattacaaaa     300
aactatccct acatttgaac caaaagagtc aatactcaaa aaattagaag acataaaacc     360
agaacaagca agaaacaaa ctaaactgtt tcgaatattt gaaccgaaac aattgcctat     420
ttatagagct aatggagaaa gagagcttcg taatagatgg tattggaaat tgaaacgaga     480
tactcttcct gatggagatt atgatgttag agagtatttt ttaaatttat atgatcaagt     540
attaatggaa atgccggatt atctattact taaagatatg gctgtagaga ataaaaattc     600
aagggatgct ggcaaagtag ttgattctga acagccgca atatgcgatg ctattttca     660 agatgaagaa ccgaaggcag taagaagatt catagctgag atgagacaac gagttcaagc     720
tgatcgaaat gtagtcaatt atccatctat attgcatcca attgaccatg cgtttaacga     780
atacttctta caacatcagt tggtagaacc attaaataat gtatacattt tcaattacat     840
accagagaga ataagaaatg atgtcaacta tatattaaat atggacagga atttaccgtc     900
tactgctaga tatatcagac caaacttgct acaagatagg ttaaatttac atgataattt     960
tgagtcactc tgggatacta taactacatc taattatatt ttagcaagat ctgtggtgcc    1020
agacctaaaa gaattagtat ctactgaggc acaaatccag aaaatgtcac aagatttgca    1080
attggaagct ttgacaatac aatcagagac tcagtttta acaggtataa actcacaagc    1140
cgctaatgat tgttttaaaa ctttgattgc tgctatgttg agtcagagaa ccatgtcatt    1200
agatttcgta acgacaaatt acatgtcact tatttcaggc atgtggttac tcactgtgat    1260
tccaaatgat atgtttataa gagaatcatt agtagcatgt caactagcca ataaaatac    1320 cattgtttat ccggcattcg gaatgcaaag aatgcattat aggaatggtg atccacagac    1380
tccctttcaa attgcagagc aacagattca aaattttcag gtagctaatt ggttacattt    1440
tgttaattat aatcagttta gacaagtagt gattgatgga gtgttaaatc aagtcttgaa    1500
tgataatata agaaatggtc atgtagtcaa ccaattaatg gaagctctga tgcaattatc    1560
tagacaacag tttcccacaa tgccagttga ttataaaaga tctatacaga gaggaattt    1620 gctgctttct aacagacttg gtcagcttgt cgatttaaca agattgttat catacaatta    1680
tgagacatta atggcatgca taacaatgaa tatgcagcat gttcaaacat taacaactga    1740
aaaattgcaa ttaacatcag taacatcatt atgtatgcta attggaaatg ctacggttat    1800
accgagtccg caaacattgt cccattacta taatgtgaat gtcaattttc attcaaatta    1860
taatgaaaga attaatgacg cagttgcaat tataactgcg gcaaatagat taaatttata    1920
tcaaaagaaa atgaaatcaa tagttgagga ctttctgaaa agattacaga tatttgatgt    1980
```

-continued

| | |
|---|---|
| tgcgagagta ccagatgacc aaatgtatag attgagagat agattaagac tattaccagt | 2040 |
| tgaaataaga agattagata tttttaattt gatagcaatg aatatggaac agattgaacg | 2100 |
| tgcatcagat aaaattgcac aaggagttat aatagcatac cgagatatgc agttagaacg | 2160 |
| agatgagatg tatggttacg tcaatattgc cagaaacttg gacggatttc aacaaataaa | 2220 |
| tcttgaagaa ttgatgagat caggagatta tgctcaaatt actaacatgc tacttaataa | 2280 |
| tcaaccagta gctttagttg gagcgctacc atttataacg gattcatcag tgatttcgtt | 2340 |
| aatagctaaa ctagatgcaa ccgttttttgc acagattgtc aaacttagaa aggtcgacac | 2400 |
| gttaaaaccc atcctatata agataaattc agattctaat gacttttatt tggtggctaa | 2460 |
| ttatgattgg attcctacat ctactacaaa agtgtataaa caagttccac aacaatttga | 2520 |
| ttttagagcg tcaatgcata tgttaacgtc taacctaaca tttaccgtat attcagattt | 2580 |
| gcttgcgttc gtttcagctg atactgttga accaattaat gctgttgctt ttgataatat | 2640 |
| gcgcatcatg aacgaactgt aaacgccaac cccattgtgg agatatgacc | 2690 |

<210> SEQ ID NO 38
<211> LENGTH: 1356
<212> TYPE: DNA
<213> ORGANISM: Simian rotavirus SA 11 clone 3 (VP6)

<400> SEQUENCE: 38

| | |
|---|---|
| ggcttttaaa cgaagtcttc aacatggatg tcctatactc tttgtcaaag actcttaaag | 60 |
| acgctagaga caaaattgtc gaaggcacat tgtattctaa cgtgagtgat ctaattcaac | 120 |
| aatttaatca atgataatt actatgaatg gaaatgaatt tcaaactgga ggaatcggta | 180 |
| atttgccaat tagaaactgg aattttaatt tcgggttact tggaacaact ttgctgaact | 240 |
| tagacgctaa ttatgttgaa acggcaagaa atacaattga ttatttcgtg gattttgtag | 300 |
| acaatgtatg catggatgag atggttagag aatcacaaag gaacggaatt gcacctcaat | 360 |
| cagactcgct aagaaagctg tcagccatta aattcaaaag aataaatttt gataattcgt | 420 |
| cggaatacat agaaaactgg aatttgcaaa atagaagaca gaggacaggt ttcactttc | 480 |
| ataaaccaaa catttttcct tattcagcat catttacact aaatagatca caacccgctc | 540 |
| atgataattt gatgggcaca atgtggttaa acgcaggatc ggaaattcaa gtcgctggat | 600 |
| ttgactactc atgtgctatt aacgcaccag ccaatataca acaatttgag catattgtgc | 660 |
| cactccgaag agtgttaact acagctacga taactcttct accagacgcg gaaaggttta | 720 |
| gttttccaag agtgatcaat tcagctgacg gggcaactac atggttttc aacccagtga | 780 |
| ttctcaggcc gaataacgtt gaagtggagt ttcatattgaa tggacagata ataaacactt | 840 |
| atcaagcaag atttggaact atcgtagcta gaaattttga tactattaga ctatcattcc | 900 |
| agttaatgag accaccaaac atgacaccag cagtagcagt actattcccg aatgcacagc | 960 |
| cattcgaaca tcatgcaaca gtgggattga cacttagaat tgagtctgca gtttgtgagt | 1020 |
| ctgtactcgc cgatgcaagt gaaactctat tagcaaatgt aacatccgtt aggcaagagt | 1080 |
| acgcaatacc agttggacca gtctttccac caggtatgaa ctggactgat ttaatcacca | 1140 |
| attattcacc gtctagggag gacaaattgc aacgcgtatt tacagtggct tccattagaa | 1200 |
| gcatgctcat taaatgagga ccaagctaac aacttggtat ccaactttgg tgagtatgta | 1260 |
| gctatatcaa gctgtttgaa ctctgtaagt aaggatgcgt atacgcattc gctacactga | 1320 |
| gtaatcactc tgatggtata gtgagaggat gtgacc | 1356 |

-continued

```
<210> SEQ ID NO 39
<211> LENGTH: 788
<212> TYPE: DNA
<213> ORGANISM: Rotavirus vp2 94-881

<400> SEQUENCE: 39
caagaacatt aataatgaca gtcctaaatc acaattatca gaaagagtat tatctaagaa      60
agaagagata attacagata atcaagaaga agttaagata tctgatgagg taaaaaaatc     120
taataaagaa gaatcgaaac agttgttaga agtacttaaa acaaaagagg aacatcaaaa     180
agaagttcag tatgaaatat tacaaaaaac tatccctaca tttgaaccaa aagagtcaat     240
actcaaaaaa ttagaagaca taaaaccaga acaagcaaag aaacaaacta aactgtttcg     300
aatatttgaa ccgaaacaat tgcctattta tagagctaat ggagaaagag agcttcgtaa     360
tagatggtat tggaaattga aacgagatac tcttcctgat ggagattatg atgttagaga     420 gtattttta aatttatatg atcaagtatt aatggaaatg ccggattatc tattacttaa     480
agatatggct gtagagaata aaaattcaag ggatgctggc aaagtagttg attctgaaac     540
agccgcaata tgcgatgcta tttttcaaga tgaagaaccg aaggcagtaa gaagattcat     600
agctgagatg agacaacgag ttcaagctga tcgaaatgta gtcaattatc catctatatt     660
gcatccaatt gaccatgcgt ttaacgaata cttcttacaa catcagttgg tagaaccatt     720
aaataatgta tacattttca attacatacc agagagaata agaaatgatg tcaactatat     780
attaaata                                                              788
```